(12) United States Patent
Moore et al.

(10) Patent No.: US 11,987,809 B2
(45) Date of Patent: May 21, 2024

(54) METHODS FOR THE TREATMENT OF CORNEAL DYSTROPHIES

(71) Applicant: Avellino Lab USA, Inc., Menlo Park, CA (US)

(72) Inventors: Tara Moore, Ballyclare (GB); Andrew Nesbit, Coleraine (GB); Gene Lee, Burlingame, CA (US); Sun-young Cho, Seoul (KR); Larry DeDionisio, Oakland (CA)

(73) Assignee: Avellino Lab USA, Inc., Menlo Park, CA (US)

( * ) Notice: Subject to any disclaimer, the term of this patent is extended or adjusted under 35 U.S.C. 154(b) by 1148 days.

(21) Appl. No.: 15/977,565

(22) Filed: May 11, 2018

(65) Prior Publication Data

US 2019/0085288 A1 Mar. 21, 2019

Related U.S. Application Data

(63) Continuation of application No. PCT/US2016/061893, filed on Nov. 14, 2016.

(60) Provisional application No. 62/255,310, filed on Nov. 13, 2015.

(51) Int. Cl.

| | |
|---|---|
| *C12N 5/079* | (2010.01) |
| *A61K 35/30* | (2015.01) |
| *A61L 27/36* | (2006.01) |
| *A61L 27/54* | (2006.01) |
| *A61P 27/02* | (2006.01) |
| *C12N 9/22* | (2006.01) |
| *C12N 15/113* | (2010.01) |
| *C12N 15/85* | (2006.01) |
| *C12Q 1/68* | (2018.01) |
| *C12Q 1/6883* | (2018.01) |

(52) U.S. Cl.
CPC ............ *C12N 5/0621* (2013.01); *A61K 35/30* (2013.01); *A61P 27/02* (2018.01); *C12N 9/22* (2013.01); *C12N 15/113* (2013.01); *C12N 15/85* (2013.01); *C12Q 1/68* (2013.01); *C12Q 1/6883* (2013.01); *A61L 27/3604* (2013.01); *A61L 27/3666* (2013.01); *A61L 27/3695* (2013.01); *A61L 27/54* (2013.01); *C12N 2510/00* (2013.01); *C12N 2533/92* (2013.01); *C12Q 2600/156* (2013.01)

(58) Field of Classification Search
CPC ........ C12N 9/22; C12N 5/0621; C12N 15/85; C12N 2310/20
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,210,015 A | 5/1993 | Gelfand et al. |
| 5,487,972 A | 1/1996 | Gelfand et al. |
| 5,925,517 A | 7/1999 | Tyagi et al. |
| 6,018,713 A | 1/2000 | Coli et al. |
| 6,103,476 A | 8/2000 | Tyagi et al. |
| 6,117,635 A | 9/2000 | Nazarenko et al. |
| 6,171,112 B1 | 1/2001 | Clark et al. |
| 6,174,670 B1 | 12/2001 | Wittwer et al. |
| 6,326,145 B1 | 12/2001 | Whitcombe et al. |
| 6,331,276 B1 | 12/2001 | Takei et al. |
| 8,697,359 B1 | 4/2014 | Zhang |
| 2002/0001812 A1 | 1/2002 | Smith et al. |
| 2003/0176650 A1 | 9/2003 | Grosse et al. |
| 2003/0204418 A1 | 10/2003 | Ley |
| 2003/0211500 A1 | 11/2003 | Woosley |
| 2004/0217345 A1 | 11/2004 | Boland et al. |
| 2004/0263853 A1 | 12/2004 | Hill et al. |
| 2005/0019757 A1 | 1/2005 | Stolarchuk |
| 2006/0038990 A1 | 2/2006 | Habib et al. |
| 2006/0057604 A1 | 3/2006 | Chen et al. |
| 2006/0066249 A1 | 3/2006 | Wark et al. |
| 2007/0254296 A1 | 11/2007 | Jiang et al. |
| 2007/0274895 A1 | 11/2007 | Jesih et al. |
| 2008/0113344 A1 | 5/2008 | Wirtz et al. |
| 2008/0174775 A1 | 7/2008 | Moskovits et al. |

(Continued)

FOREIGN PATENT DOCUMENTS

| | | |
|---|---|---|
| CN | 101144812 A | 3/2008 |
| CN | 101374850 A | 2/2009 |

(Continued)

OTHER PUBLICATIONS

Ran F et al.("In vivo genome editing using *Staphylococcus aureus* Cas9" Nature 520, 186-191 (2015)). (Year: 2015).*

Vakharia et al.(Hereditary Corneal Stromal Dystrophies: Correlation of TGFB1 Gene Mutations to Surgical Outcomes; Investigative Ophthalmology & Visual Science May 2005, vol. 46, No. 13, abstract 4941, published May 2005). (Year: 2005).*

Jeffry D. Sander et al., CRISPR-Cas systems for editing, regulating and targeting genomes , Nature Biotechnology, vol. 32, No. 4, Mar. 2, 2014, pp. 347-355, 24 pgs.

J. Gehl, "Electroporation: theory and methods, perspectives for drug delivery, gene therapy and research", Acta Physiol. Scand. 177:437-447 (2003), accepted Dec. 23, 2002 Correspondence: J. Gehl, Department of Oncology 54B1, Herlev Hospital in University of Copenhagen, Herlev Ringvej 75, 2730 Herlev, Denmark, 11 pgs.

(Continued)

*Primary Examiner* — Neil P Hammell
*Assistant Examiner* — Morgan T Lindgren Baltzell
(74) *Attorney, Agent, or Firm* — Morgan, Lewis & Bockius LLP

(57) ABSTRACT

Methods and compositions for the treatment of a corneal dystrophy in a subject in need thereof are provided. In one aspect, the method includes the step of obtaining a plurality of stem cells comprising a nucleic acid mutation in a corneal dystrophy target nucleic acid from the subject and manipulating the nucleic acid mutation in one or more stem cells of the plurality of stem cells to correct the nucleic acid mutation, thereby forming one or more manipulated stem cells. The manipulated stem cells are isolated and then transplanted into the subject. In some embodiments, the nucleic acid mutation is manipulated using CRISPR system.

20 Claims, 24 Drawing Sheets

Specification includes a Sequence Listing.

(56) References Cited

U.S. PATENT DOCUMENTS

| | | |
|---|---|---|
| 2008/0267946 A1 | 10/2008 | Kim et al. |
| 2009/0073447 A1 | 3/2009 | Dahint et al. |
| 2009/0305394 A1 | 12/2009 | Lee et al. |
| 2010/0190158 A1 | 7/2010 | Peitz et al. |
| 2011/0053794 A1 | 3/2011 | Zhang |
| 2012/0077200 A1 | 3/2012 | Lee et al. |
| 2012/0231537 A1 | 9/2012 | Templeton et al. |
| 2013/0302811 A1 | 11/2013 | Lee et al. |
| 2014/0093913 A1 | 4/2014 | Cost et al. |
| 2014/0179006 A1* | 6/2014 | Zhang .......... C12N 15/907 435/462 |
| 2014/0179770 A1 | 6/2014 | Zhang et al. |
| 2014/0170753 A1 | 7/2014 | Zhang |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang |
| 2014/0227787 A1 | 8/2014 | Zhang |
| 2014/0234972 A1 | 8/2014 | Zhang |
| 2014/0080216 A1 | 9/2014 | Cost et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0242664 A1 | 10/2014 | Zhang et al. |
| 2014/0310830 A1 | 10/2014 | Zhang et al. |
| 2014/0242699 A1 | 11/2014 | Zhang |
| 2014/0335620 A1 | 11/2014 | Zhang et al. |
| 2014/0242700 A1 | 12/2014 | Zhang et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0044772 A1* | 2/2015 | Zhao .......... C12N 9/22 435/462 |
| 2015/0056705 A1 | 2/2015 | Conway et al. |
| 2015/0073041 A1 | 3/2015 | Saltzman et al. |
| 2015/0079681 A1 | 3/2015 | Zhang |
| 2015/0184139 A1 | 7/2015 | Zhang et al. |
| 2015/0203872 A1 | 7/2015 | Zhang |
| 2015/0225801 A1* | 8/2015 | Cai .......... C12Q 1/6888 506/9 |
| 2015/0232882 A1 | 8/2015 | Zhang et al. |
| 2016/0168592 A1 | 6/2016 | Church et al. |
| 2016/0340661 A1* | 11/2016 | Cong .......... A61K 9/0048 |
| 2017/0051276 A1 | 2/2017 | May et al. |
| 2017/0233698 A1* | 8/2017 | Zhang .......... A61P 31/00 424/93.7 |
| 2019/0055552 A1 | 2/2019 | Davidson et al. |
| 2019/0185850 A1 | 6/2019 | Moore |
| 2020/0190587 A1 | 6/2020 | Moore |
| 2021/0032612 A1 | 2/2021 | Moore |
| 2021/0222171 A1 | 7/2021 | Moore |
| 2022/0056440 A1 | 2/2022 | Moore |

FOREIGN PATENT DOCUMENTS

| | | |
|---|---|---|
| CN | 102459593 A | 5/2012 |
| CN | 106282383 A | 1/2017 |
| EP | 1715326 A1 | 4/2005 |
| EP | 1964606 | 2/2008 |
| EP | 2 019 309 A2 | 7/2008 |
| EP | 2420574 A1 | 2/2012 |
| EP | 2975117 A1 | 1/2016 |
| EP | 16865232 | 6/2019 |
| JP | 2006-250668 A | 9/2006 |
| JP | 2009-045057 A | 3/2009 |
| JP | 2009-523442 A | 6/2009 |
| JP | 2012-523831 A | 11/2012 |
| JP | 2018-520149 A | 7/2018 |
| JP | 2019524149 A | 9/2019 |
| KR | 10-2007-0076532 A | 7/2007 |
| KR | 2013-0027281 A | 3/2013 |
| WO | WO 00/58509 A2 | 10/2000 |
| WO | WO 2005/015198 A1 | 2/2005 |
| WO | WO 2005/040756 A2 | 5/2005 |
| WO | WO 2005/114298 A2 | 12/2005 |
| WO | WO 2007/002567 A2 | 1/2007 |
| WO | WO 2007/083928 A1 | 7/2007 |
| WO | WO 2008/089280 A2 | 7/2008 |
| WO | WO 2012/044121 A2 | 4/2012 |
| WO | WO 2014/130518 | 8/2014 |
| WO | 2015/089462 A1 | 12/2014 |
| WO | WO 2015/089462 A1 | 12/2014 |
| WO | WO 2015/073978 A2 | 5/2015 |
| WO | WO2016049024 A2 | 3/2016 |
| WO | WO 2017/004616 A1 | 1/2017 |
| WO | WO 2014/142038 A1 | 2/2017 |
| WO | WO 2017/062983 A1 | 4/2017 |
| WO | WO 2017/118598 A1 | 7/2017 |
| WO | WO 2018/027078 A1 | 2/2018 |
| WO | WO 2018/039145 A1 | 3/2018 |
| WO | WO 2018/098480 A1 | 5/2018 |
| WO | WO 2019/046540 A1 | 3/2019 |
| WO | WO 2019/165322 A1 | 8/2019 |
| WO | WO 2020/046861 A1 | 3/2020 |

OTHER PUBLICATIONS

Neiwoehner et al., "Evolution of CRISPR RNA recognition and processing by Cas6 endonucleases", Nucleic Acids Res. 42:1341-1353 (2014), Department of Molecular and Cell Biology, University of California, Berkeley, California 94720, USA, Howard Hughes Medical Institute, University of California, Berkeley, California 94720, USA, Department of Chemistry, University of California, Berkeley, California 94720, USA and Physical Biosciences Division, Lawrence Berkeley National Laboratory, Berkeley, California 94720, USA, Published online Oct. 22, 2013, 13 pgs.

Moore, Restriction Requirement, U.S. Appl. No. 16/326,908, dated Dec. 27, 2022, 8 pgs.

Han et al., "Pathogenesis and treatments of TGFBI corneal dystrophies", Elsevier, Progress in Retinal and Eye Research, Accepted Nov. 16, 2015, Available online Nov. 28, 2015, 22 pgs.

Moore, Restriction Requirement, U.S. Appl. No. 16/609,039, dated Jan. 12, 2022, 8 pgs.

Moore, Non-Final Office Action, U.S. Appl. No. 16/609,039, dated May 18, 2022, 23 pgs.

Moore, Final Office Action, U.S. Appl. No. 16/609,039, dated Jan. 24, 2023, 6 pgs.

Ford, M. E. et al. "Conceptualizing and Categorizing Race and Ethnicity in Health Services Research", Health Services Research, vol. 40, pp. 1658-1675 (Year: 2005), 18 pgs.

Mersha, T.B. et al., "The social, economic, political and genetic value of race and ethnicity in 2020", Human Genomics, vol. 14:37, pp. 1-5 (Year: 2020), 5 pgs.

The 1000 Genomes Project Consortium, A global reference for human genetic variation, Nature, vol. 526, pp. 68-74 and supplemental pp. 1-13 (Year: 2015), 20 pgs.

Winker, M.A.; "Race and Ethnicity in Medical Research: Requirements Meet Reality", J. Law, Medicine & Ethics, vol. 34, pp. 520-525 Year: 2006), 7 pgs.

Rs55821405, dbSNP database, downloaded from www.ncbi.nlrmnih.gov/snp/?terrn=rs55821405 on May 11, 2022 (Year: 2022), 2 pgs.

Rs779010935, dbSNP database, downloaded from www.ncbi.nlrmnih.gov/snp/?terrn=rs779010935 on May 11, 2022 (Year: 2022), 1 pg.

Rs115156902, dbSNP database, released Apr. 9, 2021, downloaded from www.ncbi.nlrmnih.gov/snp/?terrn=rs115156902 on May 11, 2022 (Year: 2022), 7 pgs.

Rs199786966, dbSNP database, downloaded from www.ncbi.nlrmnih.gov/snp/?terrn=rs199786966 on May 13, 2022 (Year: 2022), 1 pg.

Rs80358202, dbSNP database, Released 90 Apr. 2021, downloaded from www.ncbi.nlm.nih.gov/snp/?terrn=rs80358202 on May 13, 2022 (Year: 2022), 9 pgs.

Aldave, A.J. et al., Keratoconus is not associated with Mutations in COL8A1 and COL8A2, Cornea, vol. 26, pp. 963-965, No. 8, Sep. 2007, 3 pgs.

(56) References Cited

OTHER PUBLICATIONS

Orlov et al; "Complexity: an internet resource for analysis of DNA sequence complexity", Nucleic Acids Research, vol. 32, Issue suppl_2, Jul. 1, 2004, pp. W628-W633, Published: Jul. 1, 2004, 6 pgs. https://doi.org/10.1093/nar/gkh466.
Avellino Lab U.S.A, Inc., JP2019558671, Notice of Reasons for Refusal, dated Nov. 1, 2022, 12 pgs.
Sambrook et al., "Molecular Cloning: A Laboratory Manual", Cold Spring Harbor Laboratory Press 1989, 2272 pgs.
Courtney et al., "A Review of Personalised Molecular Medicine for the Treatment of Corneal Disorders," International Journal of Ophthalmology and Eye Disease, S: 7-18 (2015).
Zhang et al., "Isolation and Transplantation of Corneal Endothelial Cell-Like Cells Derived from In-Vitro Differentiated Human Embryonic Stem Cells," Stem Cells and Development, 23: 1340-1354 (2014).
Byrne et al., "Genome Editing in Human Stem Cells," Methods in Enzymology, 546: 1-16 (2014).
Courtney et al., "CRISPR/Cas9 DNA Cleavage at SNP-Derived PAM Enables Both in vitro and in vivo KRT Mutation-Specific Targeting," Gene Therapy, 23:108-112 (2015).
Ouyang et al., "Ocular Stem Cell Research from Basic Science to Clinical Application: A Report from Zhongshan Ophthalmic Center Ocular Stem Cell Symposium," International Journal of Molecular Sciences, 1-15 (2016).
International Search Report issued in corresponding International Patent Application No. PCT/US2016/061893 dated Feb. 21, 2017.
Written Opinion issued in corresponding International Patent Application No. PCT/US2016/061893 dated Feb. 21, 2017.
Yukako Taketani et al., "Repair of the TGFBI gene in human corneal keratocytes derived from a granular corneal dystrophy patient via CRISPR/Cas9-induced homology-directed repair", Scientific Reports, vol. 7, No. 1, Dec. 1, 2017.
Intention to Grant, Communication under Rule 71(3) Epc, Application No. 16865232.9, dated Apr. 22, 2021, 171 pgs.
Avellino Lab USA, Inc., et al., The Extended European Search Report, Application No. 16865232.9, dated Jun. 6, 2019, 8 pgs.
Avellino Lab USA, Inc., et al., EPO Comm, article 94 (3) EPC, Application No. 16865232.9, Jan. 30, 2020, 4 pgs.
Notice of Reasons for Refusal, Japanese Patent Application No. 2018-545108, dated Nov. 4, 2020, 5 pgs.
Notice of Reasons for Refusal, Japanese Patent Application No. 2018-545108, dated Mar. 9, 2021, 3 pgs.
International Journal of Ophthalmology & Eye Science (IJOES), 2015 S. 2:002, 7-18 pgs. August.
Courtney CRISPR/Cas9 DNA Cleavage at SNP-Derived PAM Enables Both in Vitro and in vivo KRT12 Mutation-Specific Targeting, 2015, 108-112 pgs.
Avellino Lab USA, Inc, European Extended Search Report, Application No. 17844228.1, dated Feb. 28, 2020, 7 pgs.
Avellino Lab Usa, Inc., EPO Comm, article 94 (3) EPC, Application No. 17844228.1, Feb. 18, 2021, 6 pgs.
Avellino, International Search Report and Written Opinion, PCT/US2017/047861, dated Dec. 29, 2017, 13 pgs.
Avellino, International Preliminary Report on Patentability, PCT/US2017/047861, dated Feb. 26, 2019, 8 pgs.
Avellino Lab USA, Inc., Extended European Search Report, Application No., 18790019.6, dated Feb. 3, 2021, 6 pgs.
Ariela Gordon-Shaag et al., "The Genetic and Environmental Factors for Keratoconus", Biomed Research International, vol. 2015, Jan. 1, 2015, 1-19 pgs.
Karolak Justyna A et al., "Genomic strategies to understand causes of keratoconus", MGG—Molecular Genetics and Genomics, Springer, Berlin, DE, vol. 292, No. 2, Dec. 28, 2016, 251-269, pgs.
Yi Lu et al., "Genome-wide association analyses identify multiple loci associated with central corneal thickness and keratoconus", Nature Genetics, vol. 45, No. 2, Jan. 6, 2013, 155-163 pgs.
Office Action, IL Application, Application No. 153738, dated Aug. 20, 2020, 2 pgs.

International Search Report/Written Opinion, PCT/US2018/029836, dated Jun. 27, 2018, 10 pgs.
Bykhovskaya et al., "Variation in the Lysl Oxidase (LOX) Gene is Associated with Keratoconus in Family-Based and Case-Control Studies," Investigative Opthalmology & Visual Science, 53 (7): 4152-4157 (2012).
Wang et al., "Association of Interleukin-I Gene Single Nucleotide Polymorphisms with Keratoconus in Chinese Han Population," Current Eye Research, 41 (5):630-635 (2016).
Li et al., "Two-Stage Genome-Wide Linkage Scan in Keratoconus Sib Pair Families,", Investigative Ophthalmology and Visual Science, 47: 3791-3795 (2006).
Avellino, International Preliminary Report on Patentability, PCT/US2018/029836, dated Oct. 29, 2019, 8 pgs.
Shin et al., "Permananet Inactivation of Huntington's Disease Mutation by Personalized Allele-Specific CRISPR/Cas9," Human Molecular Genetics, 25 (20): 4566-4576 (2016).
Moore, International Search Report / Written Opinion, PCT/US2019/019313, dated Jul. 30, 2019, 8 pgs.
Moore, International Preliminary Report on Patentability, PCT/US2019/019313, dated Aug. 27, 2020, 6 pgs.
Hsu PD, Lander ES, Zhang F. Development and applications of CRISPR-Cas9 for genome engineering. Cell 2014; 157: 1262-1278.
Shalem O, Sanjana NE, Hartenian E, Shi X, Scott DA, Mikkelsen TS et al. Genome-scale Crispr-Cas9 knockout screening in human cells. Science 2014; 343: 84-87.
Wang T, Wei JJ, Sabatini DM, Lander ES. Genetic screens in human cells using the CRISPR-Cas9 system. Science 2014; 343: 80-84.
Weisenfeld NI, Kumar V, Shah P, Church DM, Jaffe DB. Direct determination of diploid genome sequences. Genome research. 2017; 27(5):757-767.
Ann Ran et al. Double Nicking by RNA-Guided CRISPR Cas9 for Enhanced Genome Editing Specificity, Sep. 12, 2013, 10 pgs.
Kleinstiver et al, High-Fidelity CRISPR-Cas9 Variants with Undetectable Genome-Wide Off Targets, Jan. 28, 2016, 24 pgs.
Slaymaker et al., Rationally Engineered Cas9, Nucleases with Improved Specificity, 2016, 10 pgs.
Weiss et al., IC3D Classification of Corneal Dystrophies—Edition 2, 2015, 43 pgs.
Avellino_International Search Report and Written Opinion, PCT/US2019/048240, dated Dec. 5, 2019, 9 pgs.
Avellino, International Preliminary Report on Patentability, PCT/US2019/048240, dated Mar. 2, 2021, 6 pgs.
International Search Report and Written Opinion, PCT/IB2020/054298, dated Jul. 27, 2020, 11 pgs.
Jun Wan Shin et al.: "Permanent Inactivation of Huntington's Disease Mutation by Personalized Allele-Specific CRISPR/Cas9", Human Molecular Genetics, Sep. 15, 2016 (Sep. 15, 2016), p. ddw286, XP 055403489, ISSN: 0964-6906, DOI: 10.1093/hmg/ddw286, figures 2-7; table 2.
Kathleen A. Christie et al.: "Towards Personalized Allele-Specific CRISPR Gene Editing to Treat Autosomal Dominant Disorders", Scientific Reports, vol. 7, No. 1, Nov. 23, 2017 (Nov. 23, 2017), XP055573393, DOI: 10.1038/s41598-017-16279-4.
Office Action, JP 2019-510339, dated Aug. 3, 2021, 8 pgs.
Notice of Preliminary Rejection, KR Application No. 9-5-2021-063205612, dated Aug. 9, 2021, 6 pgs.
Afshari, N., et al., "Survey of Patients With Granular, Lattice, Avellino, and Reis-Buecklers Corneal Dystrophies for Mutations in the BIGH3 and Gelsolin Genes", Arch Ophthalmol, Jan. 2001, pp. 16-22, vol. 119.
Armelao, L, et al., 'Innovative metal oxide-based substrates for DNA Microarrays', Inorganica Chimica Acta, vol. 361, No. 12-13, pp. 3603-3608 (Apr. 10, 2008).
Avellino Co. Ltd., Certificate of Patent, JP 2012-505796, May 1, 2015, 2 pgs.
Avellino Co. Ltd., European Search Report, EP 14186678.0, dated Feb. 18, 2015, 5 pgs.
Avellino Co. Ltd., Examination Report, IN 7514/CHENP/2011, dated Oct. 15, 2014, 2 pgs.
Avellino Co. Ltd., First Examination Report, IN 7514/CHENP/2011, dated Aug. 7, 2014, 1 pg.

(56) References Cited

OTHER PUBLICATIONS

Avellino Co. Ltd., Letters Patent, CN200980159748.3, Apr. 8, 2015, 2 pgs.
Avellino Co. Ltd., Notice of Reasons for Rejection, JP 2012-505796, dated Nov. 11, 2014, 7 pqs.
Avellino Co. Ltd., Notice of Reasons for Rejection, JP 2012-505796, dated Oct. 29, 2013, 3 pgs.
Avellino Co. Ltd., Notice of Reasons for Rejection, JP 2013-531500, dated Oct. 21, 2014, 5 pgs.
Avellino Co. Ltd., Notice of Reasons for Rejection, JP 2014-000571, dated Mar. 10, 2015, 6 pgs.
Avellino Co. Ltd., Notice of Reasons for Rejection, JP 2014-000571, dated Oct. 6, 2015, 7 pgs.
Avellino Co. Ltd., Certificate of Patent, JP 2014-000571, Apr. 1, 2016, 5 pgs.
Avellino Co., Ltd. Decision of Rejection, JP2013-531500, dated Aug. 21, 2015, 11 pgs.
Avellino Co., Certificate of Patent, JP2013-531500, Jan. 13, 2017, 3 pgs.
Avellino Co. Ltd., Office Action, BR-PI0924016-0, dated Sep. 12, 2018, 3 pgs. (No English Translation Available).
Avellino Co. Ltd., Notification of the Office Rejection, CN 200980159748.3, dated Aug. 6, 2014, 4 pgs.
Avellino Co. Ltd., Notification of Grant, CN201180056997.7, dated Jul. 16, 2015, 5 pgs.
Avellino Co. Ltd., The First Office Action, CN 200980159748.3, dated Aug. 31, 2012, 4 pgs.
Avellino Co. Ltd., The First Office Action, CN 201180056997.7, dated Dec. 22, 2014, 4 pgs.
Avellino Co. Ltd., The Second Office Action, CN 200980159748.3, dated Jul. 11, 2013, 5 pgs.
Avellino Co. Ltd., The Third Office Action, CN 200980159748.3, dated Mar. 24, 2014, 5 pgs.
Avellino Co. Ltd., First Office Action, CN201480072417.7, dated Feb. 27, 2019, 7 pgs.
Avellino Co. Ltd., Office Action, CN201510121642.1, dated Aug. 12, 2016, 8 pgs.
Avellino Co. Ltd., 2nd Office Action, CN201510121642.1, dated Jun. 28, 2017, 7 pgs.
Avellino Co. Ltd., Patent Examination Report No. 1, AU2009344501, dated Sep. 24, 2012, 3 pgs.
Avellino Co. Ltd., Patent Examination Rpt—No. 3-AU2009344501, dated Nov. 25, 2013, 4 pgs.
Avellino Co. Ltd., Decision to Grant, EP09843403.8, dated Feb. 10, 2014, 1 pg.
Avellino Co. Ltd., Patent Certificate, EP09843403-8, Oct. 29, 2014, 1 pg.
Avellino Co. Ltd., Communication Pursuant to Rules 161(2) and 162, EP16865232.9, dated Jun. 20, 2018, 3 pgs.
Avellino Co. Ltd., Office Action, IDW-00201103762, dated Jul. 6, 2017, 3 pgs.
Avellino Co. Ltd., Certificate of Patent for Indonesian Application No. IDW-00201103762, Apr. 12, 2018, 2 pgs.
Avellino Co. Ltd., Invitation to Respond to Written Opinion, SG201107572.8, dated Jan. 29, 2014, 12 pgs.
Avellino Co. Ltd., Certificate of Patent, ZA2011/07967, Aug. 28, 2013, 1 pg.
Avellino Co. Ltd.,Decision of Grant, RU2011146553, dated Jul. 23, 2014, 2 pgs.
Avellino Co. Ltd., Letters Patent, RU2011146553, Dec. 17, 2014, 1 pg.
Avellino Co. Ltd., The First Office Action, CN201080047181.3, dated Jul. 15, 2013, 1 pg.
Avellino Co. Ltd., Certificate of Patent, JP2012525483, Jan. 10, 2014, 5 pgs.
Avellino Co. Ltd., First office Action, IL215845, dated Jul. 10, 2013, 4 pgs.
Avellino Co. Ltd., Further Office Action, IL215845, dated Mar. 25, 2014, 4 pgs.
Avellino Co. Ltd., Office Action, KR2015-7029290, dated Mar. 12, 2019, pgs.
Avellino Lab, Extended European Search Report, EP14762603.0, dated Jul. 14, 2016, 11 pgs.
Avellino Lab, Communication Pursuant to Rules 161(2) and 162, EP14862501.5, dated Jul. 21, 2016, 2 pgs.
Avellino Lab, Communication Pursuant to Rules 70(2) and 70a(2), EP14862501.5, dated Aug. 8, 2017, 1 pg.
Avellino Lab, Extended European Search Report, EP14862501.5, dated Jul. 21, 2017, 24 pgs.
Avellino Lab, Communication Pursuant to Article 94(3), EP14862501.5, dated Jul. 16, 2018, 6 pgs.
Avellino Lab, Communication Pursuant to Rules 70(2) and 70a(2), EP14762603.0, dated Aug. 2, 2016, 12 pgs.
Avellino Lab, Communication Pursuant to Article 94(3), EP14762603.0, dated Sep. 18, 2017, 6 pgs.
Avellino Lab, Decision to Grant, EP14762603.0, dated Nov. 2, 2018, 2 pgs.
Avellino Lab, Formality Office Action JP2016531678, dated Mar. 29, 2017, 3 pgs.
Avellino Lab, Notice of Reasons for Rejection, JP2016531678, dated Oct. 16, 2018, 4 pgs.
Avellino Lab Usa Inc., International Search Report and Written Opinion, PCT/US2014/029466, dated Jul. 14, 2014, 11 pgs.
Avellino Lab Usa Inc., International Preliminary Report on Patentability, PCT/US2014/029466, dated Sep. 15, 2015, 7 pgs.
Avellino Lab Usa Inc., International Search Report and Written-Opinion, PCT/US2014/065975, dated May 18, 2015, 19 pgs.
Avellino Lab Usa Inc., International Preliminary Report on Patentability, PCT/US2014/065975, dated May 17, 2016, 12 pgs.
Avellino Lab Usa Inc., International Search Report and Written Opinion, PCT/US2016/061893, dated Feb. 21, 2017, 10 pgs.
Avellino Lab Usa Inc., International Preliminary Report on Patentability, PCT/US2016/061893, dated May 15, 2018, 6 pgs.
Beer et al., On-Chip, Real-Time, Single-Copy Polymerase Chain Reaction in Picoliter Droplets, 2007, Analytical Chemistry 79 (22): 8471, 5 pgs.
Biotechnology Journal, 2006, vol. 6, No. 5, pp. 621-624.
Byrne et al., Genome Editing in Human Stem Cells, Methods in Enzymology, 2014, vol. 546, pp. 1-16.
Korea Advanced Institute of Science and Technology et al., Invitation Pursuant to Rule 62a(1) EPC, EP10810154.4, Sep. 11, 2015, 2 pgs.
Korea Advanced Institute of Science and Technology et al., Extended European Search Report, EP10810154.4, dated Jan. 18, 2016, 9 pgs.
Korea Advanced Institute of Science and Technology et al., Communication Pursuant Article 94(3), EP10810154.4, dated Nov. 6, 2017, 5 pgs.
Chakravarthi, TGFBI Gene Mutations Causing Lattice and Granular Corneal Dystrophies in Indian Patients, Investigative Ophthalmology & Visual Science, Jan. 2005, vol. 46, No. 1, 5 pgs.
Cao W. et al., "Comparison of Methods for DNA Extraction from Paraffin-Embedded Tissues and Buccal Cells," Cancer Detection and Prevention, Elsevier Science, NL, vol. 27, No. 5, Jan. 1, 2003, 8 pgs.
Chao-Shern, Office Action, U.S. Appl. No. 14/788,572, dated Dec. 16, 2016, 14 pgs.
Chao-Shern, Notice of Allowance, U.S. Appl. No. 14/788,572, dated Aug. 28, 2017, 7 pgs.
Chao-Shern, Office Action, U.S. Appl. No. 15/154,895, dated Apr. 30, 2018, 14 pgs.
Chao-Shern, Final Office Action, U.S. Appl. No. 15/154,895, dated Oct. 12, 2018, 11 pgs.
Courtney, et al., "A Review of Personalised Molecular Medicinie for the Treatment of Cornel Disorders," International Journal of Ophthalmology and Eye Disease, Aug. 27, 2015, vol. S, No. 2, pp. 7-18.
Courtney, et al., CRISPR/Cas9 DNA Cleavage at SNP-Derived PAM Enables Both in vitro and in vivo KRT12 Mutation-Specific Targeting, Gene Therapy, Aug. 20, 2015, vol. 23, No. 1, pp. 108-112.
Database Genbank, Dec. 10, 1997, Database accession No. AF035627, 2 pgs.

(56) References Cited

OTHER PUBLICATIONS

Database Genbank, Apr. 5, 2009, Database accession No. NM000358, xx pgs.

Dias et al., "Development of a real-time PCR assay for detection of *Mytilus* species alleles: Application to a sampling survey in Scotland," Journal of Experimental Marine Biology and Ecology, Amsterdam, NL, vol. 367, No. 2, Dec. 15, 2008, 6 pgs.

Dolmetsch, A., et al., "Combined granular-lattice corneal dystrophy (Avellino) in a patient with no known Italian ancestry", Can. J. Ophthalmol, Accepted for publication Sep. 15, 1995, pp. 2931, vol. 31, No. 1.

Fujiki et al., "Six different mutations of TGFBI (betaig-h3, keratoepithelin) gene found in Japanese corneak dystrophies," Cornea: The Journal of Cornea and External DIS, Lippincott Williams & Wilkins, US, vol. 19, No. 6, Nov. 1, 2000, 4 pgs.

Endo T et al., "Label-Free Detectionof Peptide Nucleic Acid-DNA Hybridization Using Localized Surface Plasmon Resonance Based Optical Biosensor," Analytical Chemisty, American Chemical Society, US, vol. 77, No. 21, 9 pgs.

GenBank Accession No. AF035627, "*Homo sapiens* mutant kerato epithelin (BIGH3) Gene, exon 4, partial cds," [retrieved on-line: http://www.ncbi.nlm.nih.gov/nuccore/AF035627.1, retrieval date, Sep. 7, 2013], published date Dec. 1997, Skonier et al., 1 pg.

Grove, D.S., "Quantitative Real-Time Polymerase Chain Reaction for the Core Facility Using TaqMan and the Perkin-Elmer/Applied Biosystems Division 7700 Sequence Detector," Journal of Biomolecular Techniques, Mar. 1999, vol. 10, pp. 11-16.

Halfon, P., et al., "Detection of IL28B SNP DNA from Buccal Epithelial Cells, Small Amounts of Serum and Dried Blood Spots," Mar. 2012, Plos One, vol. 7, Issue 3, Article No. e33000, pp. 1-6.

Han, "Clinical Findings and Treatments of Granular Corneal Dystrophy Type 2 (Avellino Corneal Dystrophy): a Review of the Literature," Eye & Contact Lens, vol. 36, No. 5, Sep. 2010, 4 pgs.

Holland, E., et al., "Avellino corneal dystrophy. Clinical manifestations and natural history", Ophthalmology, pp. 15641568, vol. 99, No. 10.

Huerva et al., "Role of BIGH3 R124H mutation in the diagnosis of Avellino corneal dystrophy," European Journal of Ophthalmology, May 2008, vol. 18, No. 3, pp. 345-350, 6 pgs.

Jun, R., et al., "Avellino Corneal Dystrophy After Lasik", Ophthalmology, © 2004, pp. 463-468, vol. 111.

Kennedy, S., et al., "Combined granular lattice dystrophy (Avellino corneal dystrophy)", Br. J. Ophthalmol, Accepted for publication Jan. 19, er1996, pp. 489-490, vol. 80.

Kephart, D., "Rapid Isolation of Genomic DNA from Small Quantities of Human Tissue," 1999, Profiles in DNA, vol. 2, No. 3, pp. 7-9.

Kim, Jeong Wan et. al., 'Anesthetic experience for patients with malignant gyperthermia susceptibility determined by molecular genetic test', J Korean Ophthalmol Soc vol. 49, No. 9, 2008, pp. 1431-1436.

Lee, Final Office Action, U.S. Appl. No. 13/264,784, dated May 7, 2014, 26 pgs.

Lee, Final Office Action, U.S. Appl. No. 13/391,167, dated May 18, 2015, 16 pgs.

Lee, Notice of Allowance, U.S. Appl. No. 13/391,167, dated Jul. 27, 2015, 9 pgs.

Lee, Office Action, U.S. Appl. No. 13/264,784, dated Sep. 12, 2013, 14 pgs.

Lee, Office Action, U.S. Appl. No. 13/391,167, dated Dec. 29, 2014, 9 pgs.

Lee, Office Action, U.S. Appl. No. 13/876,603, dated Apr. 13, 2015, 11 pgs.

Lee, Final Office Action, U.S. Appl. No. 13/876,603, dated Nov. 6, 2015, 14 pgs.

Lee, Office Action, U.S. Appl. No. 13/876,603, dated Nov. 3, 2016, 12 pgs.

Lee, Notice of Allowance, U.S. Appl. No. 13/876,603, dated Nov. 22, 2017, 9 pgs.

Lee, Office Action, U.S. Appl. No. 14/454,669, dated May 4, 2016, 12 pgs.

Lee, Final Office Action, U.S. Appl. No. 14/454,669, dated Feb. 22, 2017, 14 pgs.

Lee, Notice of Allowance, U.S. Appl. No. 14/454,669, dated Dec. 1, 2017, 8 pgs.

Lee, Office Action, U.S. Appl. No. 14/472,325, dated Dec. 19, 2016, 18 pgs.

Li et al., "Multicolor Real-Time PCR Genotyping of ABO System Using Displacing Probes," Journal of Forensic Sciences, vol. 55, No. 1, Dec. 2, 2009, 6 pgs.

Lounsbury Jenny et al., "Enhanced Recovery of Spermatozoa and Comprehensive Lysis of Epithelial Cells from Sexual Assault Samples Having a Low Cell Counts for Aged Up to One Year," Forensic Science International: Genetics, vol. 8, No. 1, Jan. 2014, 6 pgs.

Miller, S., et al., "A Simple Salting Out Procedure for Extracting DNA from Human Nucleated Cells," Nucleic Acids Research, 1998, p. 1215, vol. 16, No. 3, Accepted for publication Jan. 19, 1996, 2 pgs.

Morbini Patrizia et al., "Oral HPV Infection and Persistence in Patients with Head and Neck Cancer," Oral Surgery, Oral Medicine, Oral Pathology and Oral Radiology, vol. 116, No. 4, Oct. 2013, 11 pgs.

Munier et al., "BIGH3 mutation spectrum in corneal dystrophies," Investigative Ophthalmology & Visual Science—IOVS, Association for Research in Vision and Ophthalmology, US., vol. 43, No. 4, Apr. 1, 2002, 6 pgs.

Neuhaus, T., et al., "Reliability of Non-Invasively Acquired Human Genomic DNA as a Substrate for Real-Time PCR-Assisted Analysis of Genetic Polymorphisms," Archives of Toxicology, vol. 78, No. 7, Jul. 1, 2004, 7 pgs.

New England Biolabs Catalog (1996-1997), pp. 111, (Year 1996).

NCBI, "*Homo Sapiens* Transforming Growth Factor, Beta-Induced, 68kDa (TGFBI), Mrna," NCBI Reference Sequence NM_900358.2, release 107, Mar. 13, 2015, 6 pgs.

Ouyang et al., Ocular Stem Cell Research from Basic Science to Clinical Application, A Repot from Zhongshan Ophthalmic Center Ocular Stem Cell Symposium, International Journal of Molecular Sciences, Mar. 22, 2016, pp. 1-15.

Paliwal et al., Heterozygous Change T>G in the Sequence of Exon 12 of TGFBI Gene Seen in a Patienet with Corneal Dystrophy, Genbank, GQ368823.1, National Center for Biotechnology Information, Genbank, Jul. 28, 2009. 6 pgs.

Richards, et al., Multiplex PCR Amplification from the CFTR Gene Using DNA Prepared from Buccal Brushes/Swabs, 1993, Human Molecular Genetics 2 (2): 159-163, 5 pgs.

Romero, P. et al., 'Anticipation in familial lattice corneal dystrophy type I with R124C mutation in the TGFBI {BIGH3) gene', Molecular Vision vol. 14, May 7, 2008, pp. 829-835.

Stewart, Heterogeneity in Granular Corneal Dystrophy: Identification of Three Causative Mutations in the TGFBI (BIGH3) Gene—Lessons for Corneal Amyloidogenesis, Human Mutation 14:126-132 (1999), 8 pgs.

Strum, J.C. et al., 'Tissue expression profiling using real-time PCR', Curr Protoc Pharmacol Nov. 2002;Chapter 6:Unit 6.9. DOI: 10.1002/0471141755.PH0609S18.

Walker et al., Collection of Genomic DNA by Buccal Swabs for Polymerase Chain Reaction-Based Biomaker Assays, 1999, Environmental Health Perspectives 107 (7): 517, 4 pgs.

Wittwer, Carl T. , et al., "Real-Time Multiplex PCR Assays," 2001, Department of Pathology, University of Utah, School of Medicine, Salt Lake City, Utah 84132, 13 pgs.

Yoo et al., "Detection of the Most Common Corneal Dystrophies Caused by BIGH3 Gene Point Mutations Usig a Multispot Gold-Capped Nanoparticle Array Chip," Anal. Chem. 2010, American Chemical Society, Published on Web Jan. 21, 2010, pp. 1349-1357.

Yoo, So Young et al., 'Development of a DNA chip for the diagnosis of the most common corneal dystrophies caused by mutations in the high 3 gene', Br J Ophthalmol vol. 91, Jan. 10, 2007, pp. 722-727.

Yoshida, S., et al., 'An analysis of BIGH3 mutations in patients with corneal dystrophies in the Kyushu district of Japan', Jpn J Ophthalmol. Jul.-Aug. 2002;46(4):469-71.

(56) References Cited

OTHER PUBLICATIONS

Yoshida, S., et al., "Rapid genotyping for most common TGFI mutations with real-time polymerase chain reaction," Human Genetics, Springer, Berlin, DE, vol. 116, No. 6, May 1, 2005, 7 pgs.

Zhang, et al., Isolation and Transplantation of Corneal Endothelial Cell-Like Cells Derived from In-Vitro-Differentiated Human Embryonic Stem Cells, Stem Cells and Development, Feb. 5, 2014, vol. 23, No. 12, pp. 1340-1354.

Zheng, Y. B., et al., 'Surface plasmons of metal nanostructure arrays: from nanoengineering to active plasmonics', Journal of the Association for Laboratory Automation, vol. 13, No. 4, pp. 215-226 (Jul. 9, 2008).

Avellino Lab USA, Inc., International Preliminary Report on Patentability, PCT/US2017/047861, dated Dec. 29, 2017, 8 pgs.

Avellino Lab USA, Inc., PCT/US2017/047861, International Search Report/Written Opinion, dated Dec. 29, 2017, 13 pgs.

Moore, Non-Final Office Action, U.S. Appl. No. 16/326,908, Mar. 31, 2023, 34 pgs.

Kleinstiver et al., Engineered CRISPR-Cas9 nucleases with altered PAM specificities. Nature (2015), 523: 481-485 (Year: 2015), 17 pgs.

Plasmid #48139, Sequence Analyser: pSpCas9(BB)-2A-Puro (PX459), https://www.addgene.org/48139/ [retrieved Mar. 23, 2023] (Year: 2023), 25 pgs.

Usui et al., "To Protect Corneal Transparency Against Diseases," The 119th Annual Meeting of the Japanese Ophthalmological Society Council nomination lecture III (2015), 120, 3, 246 (Year: 2015), 45 pgs.

Homo sapiens transforming growth factor beta induced (TGFBI), RefSeqGene on chromosome 5, [retrieved Mar. 23, 2023], published May 2020 and sequence derived from AC004503.1 and AC005219.1, which were published Jul. 2016 (Year: 2016), 13 pgs. https://www.ncbi.nlm.nih.gov/ nuccore/255652922.

BLAST alignment tools, 12 pgs. https://blast.ncbi.nlm.nih.gov/Blast.cgi (Year: 2023).

Lee et al., Tgfbi Deficiency Leads to a Reduction in Skeletal Size and Degradation of the Bone Matrix. Calcif Tissue Int (2015), 96: 56-64 (Year: 2015), 9 pgs.

dbsnp, Short Genetic Variations Database, [retrieved Mar. 24, 2023]; variations submitted Aug. 21, 2014 (Year: 2014), 4 pgs. https://www.ncbi.nlm.nih.gov/snp/rs374380455.

dbsnp, Short Genetic Variations Database, [retrieved Mar. 24, 2023]; variations submitted Aug. 21, 2014 (Year: 2014), 5 pgs. https://www.ncbi.nlm.nih.gov/snp/rs550826371.

Moore, Final Office Action, U.S. Appl. No. 16/326,908, Jul. 28, 2023, 22 pgs.

Moore, Non-Final Office Action, U.S. Appl. No. 17/520,517, May 30, 2023, 22 pgs.

Fagerlund et al., "The Cpf1 CRISPR-Cas Protein Expands Genome-Editing Tools", Genome Biology 16.1, Article No. 251, Nov. 2015, 3 pgs.

Ng et al., "Whole Genome Sequencing", Genetic Variation: Methods and Protocols, vol. 628, Jan. 2010, 12 pg.

Moore, Restriction/Election Requirement, U.S. Appl. No. 16/971,712, Nov. 2, 2023, 10 pgs.

dbSNP, Short Genetic Variations Database https://www.ncbi.nlm.nih.gov/snp/rs756462 and /snp/rs764567, https://www.ncbi.nlm.nih.gov/projects/SNP/snp_ss.cgi?subsnp_id=ss1317348609, and Id=ss1317348180#freq [retrieved Jul. 21, 2023]; variations submitted Aug. 21, 2014 (Year: 2014), 14 pgs.

DeDionisio, Non-Final Office Action, U.S. Appl. No. 16/609,039, Mar. 20, 2023, 8 pgs.

Kathryn P. Burdon et al., "Association of Polymorphisms in the Hepatocyte Growth Factor Gene Promoter with Keratoconus", Cornea, Investigative Ophthalmology & Visual Science Oct. 2011, vol. 52, 8514-8519. doi:https://doi.org/10.1167/iovs.11-8261, 6 pgs.

Using Whole-Genome Amplified (WGA) DNA Samples in the GoldenGate Genotyping Assay, Illumina, Technical Note "SNP Genotyping", 1-3 pp. (Year: 2010), 3 pgs.

\* cited by examiner

Spy Cas9 sgRNA sequence
NNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGCUUUUUU (SEQ ID NO: 1)
wherein the "NNNNNNNNNNNNNNNNNNNN" represents the guide sequence (crRNA) in sgRNA, and
"GUUUUAGAGCUAGAAAUAGCAAGUUAAAAUAAGGCUAGUCCGUUAUCAACUUGAAAAAGUGGCACCGAGUCGGUGCUUUUUU" (SEQ ID NO: 2) is an exemplary tracrRNA or sgRNA scaffold sequence.
The number of N does not represent the actual number of nucleotides in the guide sequence.

Spy Cas9 nucleotide sequence
atggactataaggaccacgacggagactacaaggatcatgatattgattacaaagacgatgacgataagatggccccaaagaagaagcggaagg
tcggtatccacggagtcccagcagccgacaagaagtacagcatcggcctggacatcggcaccaactctgtgggctgggccgtgatcaccgacg
agtacaaggtgcccagcaagaaattcaaggtgctgggcaacaccgaccggcacagcatcaagaagaacctgatcggagccctgctgttcgaca
gcggcgaaacagccgaggccacccggctgaagagaaccgccagaagaagatacaccagacggaagaaccggatctgctatctgcaagagat
cttcagcaacgagatggccaaggtggacgacagcttcttccacagactggaagagtccttcctggtggaagaggataagaagcacgagcggcac
cccatcttcggcaacatcgtggacgaggtggcctaccacgagaagtaccccaccatctaccacctgagaaagaaactggtggacagcaccgaca
aggccgacctgcggctgatctatctggccctggcccacatgatcaagttccggggccacttcctgatcgagggcgacctgaaccccgacaacag
cgacgtggacaagctgttcatccagctggtgcagacctacaaccagctgttcgaggaaaaccccatcaacgccagcggcgtggacgccaaggc
catcctgtctgccagactgagcaagagcagacggctggaaaatctgatcgcccagctgcccggcgagaagaagaatggcctgttcggaaacctg
attgccctgagcctgggcctgaccccaacttcaagagcaacttcgacctggccgaggatgccaaactgcagctgagcaaggacacctacgacg
acgacctggacaacctgctggcccagatcggcgaccagtacgccgacctgtttctggccgccaagaacctgtccgacgccatcctgctgagcga
catcctgagagtgaacaccgagatcaccaaggcccccctgagcgcctctatgatcaagagatacgacgagcaccaccaggacctgaccctgctg
aaagctctcgtgcggcagcagctgcctgagaagtacaaagagattttcttcgaccagagcaagaacggctacgccggctacattgacggcggag
ccagccaggaagagttctacaagttcatcaagcccatcctggaaaagatggacggcaccgaggaactgctcgtgaagctgaacagagaggacct
gctgcggaagcagcggaccttcgacaacggcagcatccccaccagatccacctgggagagctgcacgccattctgcggcggcaggaagattt
ttacccattcctgaaggacaaccgggaaaagatcgagaagatcctgaccttccgcatccctactacgtgggccctctggccaggggaaacagca
gattcgcctggatgaccagaaagagcgaggaaaccatcacccctggaacttcgaggaagtggtggacaagggcgcttccgcccagagcttcat
cgagcggatgaccaacttcgataagaacctgcccaacgagaaggtgctgcccaagcacagcctgctgtacgagtacttcaccgtgta

Figure 11 (continued)

taacgagctgaccaaagtgaaatacgtgaccgagggaatgagaaagcccgccttcctgagcggcgagcagaaaaaggccatcgtggacctgct
gttcaagaccaaccggaaagtgaccgtgaagcagctgaaagaggactacttcaagaaaatcgagtgcttcgactccgtggaaatctccggcgtgg
aagatcggttcaacgcctccctgggcacataccacgatctgctgaaaattatcaaggacaaggacttcctggacaatgaggaaaacgaggacattc
tggaagatatcgtgctgaccctgacactgtttgaggacagagagatgatcgaggaacggctgaaaacctatgcccacctgttcgacgacaaagtg
atgaagcagctgaagcggcggagatacaccggctggggcaggctgagccggaagctgatcaacggcatccgggacaagcagtccggcaaga
caatcctggatttcctgaagtccgacggcttcgccaacagaaacttcatgcagctgatccacgacgacagcctgacctttaaagaggacatccaga
aagcccaggtgtccggccagggcgatagcctgcacgagcacattgccaatctggccggcagccccgccattaagaagggcatcctgcagacag
tgaaggtggtggacgagctcgtgaaagtgatgggccggcacaagcccgagaacatcgtgatcgaaatggccagagagaaccagaccacccag
aagggacagaagaacagccgcgagagaatgaagcggatcgaagagggcatcaaagagctgggcagccagatcctgaaagaacaccccgtg
gaaaacacccagctgcagaacgagaagctgtacctgtactacctgcagaatgggcgggatatgtacgtggaccaggaactggacatcaaccgg
ctgtccgactacgatgtggaccatatcgtgcctcagagctttctgaaggacgactccatcgacaacaaggtgctgaccagaagcgacaagaaccg
gggcaagagcgacaacgtgcccctccgaagaggtcgtgaagaagatgaagaactactggcggcagctgctgaacgccaagctgattacccaga
gaaagttcgacaatctgaccaaggccgagagaggcggcctgagcgaactggataaggccggcttcatcaagagacagctggtggaaacccgg
cagatcacaaagcacgtggcacagatcctggactcccgatgaacactaagtacgacgagaatgacaagctgatccgggaagtgaaagtgatca
ccctgaagtccaagctggtgtccgatttccggaaggatttccagttttacaaagtgcgcgagatcaacaactaccaccacgcccacgacgcctacct
gaacgccgtcgtgggaaccgccctgatcaaaaagtaccctaagctggaaagcgagttcgtgtacggcgactacaaggtgtacgacgtgcggaa
gatgatcgccaagagcgagcaggaaatcggcaaggctaccgccaagtacttcttctacagcaacatcatgaacttttcaagaccgagattaccct
ggccaacggcgagatccggaagcggcctctgatcgagacaaacggcgaaaccggggagatcgtgtgggataagggccgggatttgccaccg
tgcggaaagtgctgagcatgccccaagtgaatatcgtgaaaaagaccgaggtgcagacaggcggcttcagcaaagagtctatcctgcccaagag
gaacagcgataagctgatcgccagaaagaaggactgggaccctaagaagtacggcggcttcgacagccccaccgtggcctattctgtgctggtg
gtggccaaagtggaaaagggcaagtccaagaaactgaagagtgtgaaagagctgctggggatcaccatcatggaaagaagcagcttcgagaag
aatcccatcgactttctggaagccaagggctacaaagaagtgaaaaaggacctgatcatcaagctgcctaagtactccctgttcgagctggaaaac
ggccggaagagaatgctggcctctgccggcgaactgcagaagggaaacgaactggccctgccctccaaatatgtgaacttcctgtacctggcca
gccactatgagaagctgaagggctcccccgaggataatgagcagaaacagctgtttgtggaacagcacaagcactacctggacgagatcatcga
gcagatcagcgagttctccaagagagtgatcctggccgacgctaa (SEQ ID NO: 3)

Spy Cas9 amino acid sequence
MDYKDHDGDYKDHDIDYKDDDDKMAPKKKRKVGIHGVPAADKKYSIGLDIGTNSVGWAV
ITDEYKVPSKKFKVLGNTDRHSIKKNLIGALLFDSGETAEATRLKRTARRRYTRRKNRICYLQ
EIFSNEMAKVDDSFFHRLEESFLVEEDKKHERHPIFGNIVDEVAYHEKYPTIYHLRKKLVDST
DKADLRLIYLALAHMIKFRGHFLIEGDLNPDNSDVDKLFIQLVQTYNQLFEENPINASGVDAK
AILSARLSKSRRLENLIAQLPGEKKNGLFGNLIALSLGLTPNFKSNFDLAEDAKLQLSKDTYD
DDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNEL
TKVKYVTEGMRKPAFLSGEQKKAIVDLLFKTNRKVTVKQLKEDYFKKIECFDSVEISGVEDR
FNASLGTYHDLLKIIKDKDFLDNE

Figure 11 (continued)

ENEDILEDIVLTLTLFEDREMIEERLKTYAHLFDDKVMKQLKRRRYTGWGRLSRKLINGIRD
KQSGKTILDFLKSDGFANRNFMQLIHDDSLTFKEDIQKAQVSGQGDSLHEHIANLAGSPAIKK
GILQTVKVVDELVKVMGRHKPENIVIEMARENQTTQKGQKNSRERMKRIEEGIKELGSQILK
EHPVENTQLQNEKLYLYYLQNGRDMYVDQELDINRLSDYDVDHIVPQSFLKDDSIDNKVLT
RSDKNRGKSDNVPSEEVVKKMKNYWRQLLNAKLITQRKFDNLTKAERGGLSELDKAGFIKR
QLVETRQITKHVAQILDSRMNTKYDENDKLIREVKVITLKSKLVSDFRKDFQFYKVREINNY
HHAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTGG
FSKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELALP
SKYVNFLYLASHYEKLKGSPEDNEQKQLFVEQHKHYLDEIIEQISEFSKRVILADANLDKVLS
AYNKHRDKPIREQAENIIHLFTLTNLGAPAAFKYFDTTIDRKRYTSTKEVLDATLIHQSITGLY
ETRIDLSQLGGDKRPAATKKAGQAKKKK (SEQ ID NO: 4)

Sau Cas9 sgRNA

GNNNNNNNNNNNNNNNNNNNNNGUUUUAGUACUCUGGAAACAGAAUCUACUAAAACA
AGGCAAAUGCCGUGUUUAUCUCGUCAACUUGUUGGCGAAGAUUUUUUU (SEQ ID NO: 5)

wherein the "NNNNNNNNNNNNNNNNNNNNN" represents the guide sequence (crRNA) in sgRNA, and
"GUUUUAGUACUCUGGAAACAGAAUCUACUAAAACAAGGCAAAUGCCGUGUUUAUCU
CGUCAACUUGUUGGCGAAGAUUUUUUU" (SEQ ID NO: 6) is an exemplary tracrRNA or sgRNA scaffold sequence.

Sau Cas9 nucleotide sequence

ATGGCCCCAAAGAAGAAGCGGAAGGTCGGTATCCACGGAGTCCCAGCAGCCAAGCGGAACTACA
TCCTGGGCCTGGACATCGGCATCACCAGCGTGGGCTACGGCATCATCGACTACGAGACACGGGA
CGTGATCGATGCCGGCGTGCGGCTGTTCAAAGAGGCCAACGTGGAAAACAACGAGGGCAGGCGG
AGCAAGAGAGGCGCCAGAAGGCTGAAGCGGCGGAGGCGGCATAGAATCCAGAGAGTGAAGAAG
CTGCTGTTCGACTACAACCTGCTGACCGACCACAGCGAGCTGAGCGGCATCAACCCCTACGAGGC
CAGAGTGAAGGGCCTGAGCCAGAAGCTGAGCGAGGAAGAGTTCTCTGCCGCCCTGCTGCACCTG
GCCAAGAGAAGAGGCGTGCACAACGTGAACGAGGTGGAAGAGGACACCGGCAACGAGCTGTCC
ACCAAAGAGCAGATCAGCCGGAACAGCAAGGCCCTGGAAGAGAAATACGTGGCCGAACTGCAG
CTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCT
TCATCGACACCTACATCGACCTGCTGGAAACCCGGCGGACCTACTATGAGGGACCTGGCGAGGG
CAGCCCCTTCGGCTGGAAGGACATCAAAGAATGGTACGAGATGCTGATGGGCCACTGCACCTAC
TTCCCCGAGGAACTGCGGAGCGTGAAGTACGCCTACAACGCCGACCTGTACAACGCCCTGAACG
ACCTGAACAATCTCGTGA

Figure 11 (continued)

TCACCAGGGACGAGAACGAGAAGCTGGAATATTACGAGAAGTTCCAGATCATCGAGAACGTGTT
CAAGCAGAAGAAGAAGCCCACCCTGAAGCAGATCGCCAAAGAAATCCTCGTGAACGAAGAGGA
TATTAAGGGCTACAGAGTGACCAGCACCGGCAAGCCCGAGTTCACCAACCTGAAGGTGTACCAC
GACATCAAGGACATTACCGCCCGGAAAGAGATTATTGAGAACGCCGAGCTGCTGGATCAGATTG
CCAAGATCCTGACCATCTACCAGAGCAGCGAGGACATCCAGGAAGAACTGACCAATCTGAACTC
CGAGCTGACCCAGGAAGAGATCGAGCAGATCTCTAATCTGAAGGGCTATACCGGCACCCACAAC
CTGAGCCTGAAGGCCATCAACCTGATCCTGGACGAGCTGTGGCACACCAACGACAACCAGATCG
CTATCTTCAACCGGCTGAAGCTGGTGCCCAAGAAGGTGGACCTGTCCCAGCAGAAAGAGATCCC
CACCACCCTGGTGGACGACTTCATCCTGAGCCCCGTCGTGAAGAGAAGCTTCATCCAGAGCATCA
AAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACC
AACGAGCGGATCGAGGAAATCATCCGGACCACCGGCAAAGAGAACGCCAAGTACCTGATCGAG
AAGATCAAGCTGCACGACATGCAGGAAGGCAAGTGCCTGTACAGCCTGGAAGCCATCCCTCTGG
AAGATCTGCTGAACAACCCCTTCAACTATGAGGTGGACCACATCATCCCCAGAAGCGTGTCCTTC
GACAACAGCTTCAACAACAAGGTGCTCGTGAAGCAGGAAGAAAACAGCAAGAAGGGCAACCGG
ACCCCATTCCAGTACCTGAGCAGCAGCGACAGCAAGATCAGCTACGAAACCTTCAAGAAGCACA
TCCTGAATCTGGCCAAGGGCAAGGGCAGAATCAGCAAGACCAAGAAAGAGTATCTGCTGGAAGA
ACGGGACATCAACAGGTTCTCCGTGCAGAAAGACTTCATCAACCGGAACCTGGTGGATACCAGA
TACGCCACCAGAGGCCTGATGAACCTGCTGCGGAGCTACTTCAGAGTGAACAACCTGGACGTGA
AAGTGAAGTCCATCAATGGCGGCTTCACCAGCTTTCTGCGGCGGAAGTGGAAGTTTAAGAAAGA
GCGGAACAAGGGGTACAAGCACCACGCCGAGGACGCCCTGATCATTGCCAACGCCGATTTCATC
TTCAAAGAGTGGAAGAAACTGGACAAGGCCAAAAAAGTGATGGAAAACCAGATGTTCGAGGAA
AAGCAGGCCGAGAGCATGCCCGAGATCGAAACCGAGCAGGAGTACAAAGAGATCTTCATCACCC
CCCACCAGATCAAGCACATTAAGGACTTCAAGGACTACAAGTACAGCCACCGGGTGGACAAGAA
GCCTAATAGAGAGCTGATTAACGACACCCTGTACTCCACCCGGAAGGACGACAAGGGCAACACC
CTGATCGTGAACAATCTGAACGGCCTGTACGACAAGGACAATGACAAGCTGAAAAAGCTGATCA
ACAAGAGCCCCGAAAAGCTGCTGATGTACCACCACGACCCCCAGACCTACCAGAAACTGAAGCT
GATTATGGAACAGTACGGCGACGAGAAGAATCCCCTGTACAAGTACTACGAGGAAACCGGGAAC
TACCTGACCAAGTACTCCAAAAAGGACAACGGCCCCGTGATCAAGAAGATTAAGTATTACGGCA
ACAAACTGAACGCCCATCTGGACATCACCGACGACTACCCCAACAGCAGAAACAAGGTCGTGAA
GCTGTCCCTGAAGCCCTACAGATTCGACGTGTACCTGGACAATGGCGTGTACAAGTTCGTGACCG
TGAAGAATCTGGATGTGATCAAAAAAGAAAACTACTACGAAGTGAATAGCAAGTGCTATGAGGA
AGCTAAGAAGCTGAAGAAGATCAGCAACCAGGCCGAGTTTATCGCCTCCTTCTACAACAACGAT
CTGATCAAGATCAACGGCGAGCTGTATAGAGTGATCGGCGTGAACAACGACCTGCTGAACCGGA
TCGAAGTGAACATGATCGACATCACCTACCGCGAGTACCTGGAAAACATGAACGACAAGAGGCC
CCCCAGGATCATTAAGACAATCGCCTCCAAGACCCAGAGCATTAAGAAGTACAGCACAGACATT
CTGGGCAACCTGTATGAAGTGAAATCTAAGAAGCACCCTCAGATCATCAAAAAGGGCAAAGGC
CGGCGGCCACGAAAAGGCCGGCCAGGCAAAAAGAAAAAGggatccTACCCATACGATGTTCCAG
ATTACGCTTACCCATACGATGTTCCAGATTACGCTTACCCATACGATGTTCCAGATTACGCTtaa
(SEQ ID NO: 7)

Figure 11 (continued)

Sau Cas9 amino acid sequence

MAPKKKRKVGIHGVPAAKRNYILGLDIGITSVGYGIIDYETRDVIDAGVRLFKEANVENNEG
RRSKRGARRLKRRRRHRIQRVKKLLFDYNLLTDHSELSGINPYEARVKGLSQKLSEEEFSAA
LLHLAKRRGVHNVNEVEEDTGNELSTKEQISRNSKALEEKYVAELQLERLKKDGEVRGSINR
FKTSDYVKEAKQLLKVQKAYHQLDQSFIDTYIDLLETRRTYYEGPGEGSPFGWKDIKEWYE
MLMGHCTYFPEELRSVKYAYNADLYNALNDLNNLVITRDENEKLEYYEKFQIIENVFKQKK
KPTLKQIAKEILVNEEDIKGYRVTSTGKPEFTNLKVYHDIKDITARKEIIENAELLDQIAKILTI
YQSSEDIQEELTNLNSELTQEEIEQISNLKGYTGTHNLSLKAINLILDELWHTNDNQIAIFNRLK
LVPKKVDLSQQKEIPTTLVDDFILSPVVKRSFIQSIKVINAIIKKYGLPNDIIIELAREKNSKDAQ
KMINEMQKRNRQTNERIEEIIRTTGKENAKYLIEKIKLHDMQEGKCLYSLEAIPLEDLLNNPF
NYEVDHIIPRSVSFDNSFNNKVLVKQEENSKKGNRTPFQYLSSSDSKISYETFKKHILNLAKG
KGRISKTKKEYLLEERDINRFSVQKDFINRNLVDTRYATRGLMNLLRSYFRVNNLDVKVKSI
NGGFTSFLRRKWKFKKERNKGYKHHAEDALIIANADFIFKEWKKLDKAKKVMENQMFEEK
QAESMPEIETEQEYKEIFITPHQIKHIKDFKDYKYSHRVDKKPNRELINDTLYSTRKDDKGNT
LIVNNLNGLYDKDNDKLKKLINKSPEKLLMYHHDPQTYQKLKLIMEQYGDEKNPLYKYYEE
TGNYLTKYSKKDNGPVIKKIKYYGNKLNAHLDITDDYPNSRNKVVKLSLKPYRFDVYLDNG
VYKFVTVKNLDVIKKENYYEVNSKCYEEAKKLKKISNQAEFIASFYNNDLIKINGELYRVIGV
NNDLLNRIEVNMIDITYREYLENMNDKRPPRIIKTIASKTQSIKKYSTDILGNLYEVKSKKHPQ
IIKKGKRPAATKKAGQAKKKKGSYPYDVPDYAYPYDVPDYAYPYDVPDYA (SEQ ID NO: 8)

METHODS FOR THE TREATMENT OF CORNEAL DYSTROPHIES

SEQUENCE LISTING

The instant application contains a Sequence Listing which has been submitted electronically in ASCII format and is hereby incorporated by reference in its entirety. Said ASCII copy, created on Sep. 7, 2021, is named 070315-50091-US_SL .txt and is 43,026 bytes in size.

TECHNICAL FIELD

The present disclosure generally relates to methods for the treatment of corneal dystrophies. In particular, the present disclosure relates to methods for the treatment of corneal dystrophies associated with a genetic mutation.

BACKGROUND

Corneal dystrophies are a group of hereditary disorders in the outer layer of the eye (cornea). For example, the corneal dystrophy may be characterized by bilateral abnormal deposition of substances in the cornea, the transparent front part of the eye. Corneal dystrophies include, but are not limited to the following four IC3D categories of corneal dystrophies (see, e.g., Weiss et al., Cornea 34(2): 117-59 (2015)): epithelial and subepithelial dystrophies, epithelial-stromal TGFβI dystrophies, stromal dystrophies and endothelial dystrophies. The corneal dystrophy may be caused by a mutation located in Transforming growth factor, beta-induced (TGFβI), keratin 3 (KRT3), keratin 12 (KRT12), GSN, or UbiA prenyltransferase domain containing 1 (UBIAD1).

For example, a subset of such corneal dystrophies, epithelial-stromal corneal dystrophies, is known to be associated with mutations in transforming growth factor beta induced (TGFβI) gene. The TGFβI gene encodes an arginyl-glycyl-aspartic acid (RGD) containing protein that binds to type I, II and IV collagens. The RGD motif is found in many extracellular matrix proteins modulating cell adhesion and serves as a ligand recognition sequence for several integrins. In some cases, epithelial-stromal corneal dystrophies are distinguished from each other and are divided into subtypes on the basis of the clinical appearance of the opacities, clinical features of the disease, and on histopathological staining properties of the deposits. Without being bound by any particular theory of operation, it is believed that specific mutations in the TGFβI gene account for the specific phenotypes associated with such corneal dystrophies and that the corneal opacities that account for the clinical features of the different phenotypes result from the deposition of all or part of the mutated encoded TGFβI protein. Avellino corneal dystrophy, also known as granular corneal dystrophy type II, is a form of an epithelial-stromal corneal dystrophy, characterized by irregular-shaped, well-demarcated granular deposits in the superficial central corneal stroma and progressive visual impairment. Heterozygous patients suffering from Avellino corneal dystrophy have increasing loss in vision with age that becomes severe in the later years in life. Homozygous patients, in contrast, have severe to complete loss of vision by six years of age.

Keratoconus (KTCN) is the most common corneal ectatic disorder with approximately 6-23.5% of subjects carrying a positive family history (Wheeler, J., Hauser, M. A., Afshari, N. A., Allingham, R. R., Liu, Y., *Reproductive Sys Sexual Disord* 2012; S: 6). The reported prevalence of KTCN ranges from 8.8 to 54.4 per 100,000. variation in prevalence is partly due to the different criteria used to diagnose the disease. (Wheeler, J., Hauser, M. A., Afshari, N. A., Allingham, R. R., Liu, Y., *Reproductive Sys Sexual Disord* 2012; S: 6; and Nowak, D., Gajecka, M., *Middle East Afr J Ophthalmol* 2011; 18(1): 2-6). Many studies exist within the literature that attempt to define the genetic causes of KTCN. These studies have uncovered numerous possible genetic variants or single nucleotide polymorphisms (SNPs) that are believed to contribute to the etiology of the disease depending on the experimental parameters. During the course of keratoconus the central or paracentral cornea undergoes progressive thinning and steepening causing irregular astigmatism. The hereditary pattern is neither prominent nor predictable, but positive family histories have been reported. The incidence of keratoconus is often reported to be 1 in 2000 people. Keratoconus can show the following pathologic findings, including, fragmentation of Bowman's layer, thinning of stroma and overlying epithelium, folds or breaks in Descemet's membrane, and variable amounts of diffuse corneal scarring.

Early stages of corneal dystrophies are treated initially with hypertonic eye drops and ointments to reduce the corneal edema and may offer symptomatic improvement prior to surgical intervention. Suboptimal vision caused by corneal dystrophy usually requires surgical intervention in the form of corneal transplantation. However, the shortage in the availability of donor corneal tissues limits the use of the surgical intervention. In addition, recurrence of the disease in the donor graft, however, may occur following corneal transplantation. Other complications that may arise following a corneal transplantation include, for example, scarring, cataract formation, leakage of fluid from the transplant incision, infection and vision problems. Accordingly, alternative methods for the treatment of corneal dystrophies are needed.

SUMMARY

Provided herein are compositions, methods and systems for the treatment of a corneal dystrophy in a subject in need thereof. In certain embodiments, the corneal dystrophy is granular corneal dystrophy type II. In other embodiments, the corneal dystrophy is keratoconus. In some embodiments, the corneal dystrophy is associated with single-nucleotide polymorphism (SNP), for example, in TGFBI, KRT3, KRT12, GSN, and/or UBIAD1 gene.

In one aspect, provided herein is a method of preventing, ameliorating, or treating corneal dystrophy in a subject in need thereof.

In some embodiments, the method includes manipulating a nucleic acid mutation in a corneal dystrophy target nucleic acid in a stem cell from the subject to correct the nucleic acid mutation, thereby forming a manipulated stem cell; and transplanting the manipulated stem cell into the subject. In additional embodiments, the method further comprises culturing the manipulated stem cell prior to transplanting, thereby forming a plurality of manipulated stem cells, and the transplanting comprises transplanting the plurality of manipulated stem cells. In further embodiments, the method includes manipulating the nucleic acid mutation in a plurality of stem cells from the subject to correct the nucleic acid mutation, thereby forming one or more manipulated stem cells; isolating the one or more manipulated stem cells; and transplanting the one or more manipulated stem cells. In yet further embodiments, the method comprises culturing the one or more manipulated stem cells prior to transplanting, thereby forming a plurality of manipulated stem cells, and the transplanting comprises transplanting the plurality of manipulated stem cells. In some embodiments, the method further comprises obtaining from the subject stem cells that include the nucleic acid mutation in a corneal dystrophy target nucleic acid.

In some embodiments, the method includes the steps of a) obtaining a plurality of stem cells comprising a nucleic acid mutation in a corneal dystrophy target nucleic acid from the subject; b) manipulating the nucleic acid mutation in one or more stem cells of the plurality of stem cells to correct the nucleic acid mutation, thereby forming one or more manipulated stem cells; c) isolating the one or more manipulated stem cells; and d) transplanting the one or more manipulated stem cells into the subject. In some embodiments, the corneal dystrophy target nucleic acid is a TGFβI target nucleic acid. In other embodiments, the corneal dystrophy target nucleic acid is a COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1 target nucleic acid.

In some embodiments, the culturing is performed after manipulating.

In some embodiments, the nucleic acid mutation is manipulated by introducing a set of nucleic acid manipulation reagents into the isolated plurality of stem cells, whereby the nucleic acid manipulation reagents correct the nucleic acid mutation in one or more of the plurality of stem cells. In further embodiments, the nucleic acid manipulation reagents are introduced into the plurality of stem cells using electroporation, transfection or viral delivery.

In certain embodiments and in accordance with any of the above, the nucleic acid mutation encodes for an amino acid substitution of arginine 124, arginine 555, or histidine 666 in a TGFβI polypeptide. In some embodiments, the nucleic acid mutation encodes for an amino acid substitution selection from R124C, R124H, R124L, R555W, R555Q, and H626P.

In some embodiments, the nucleic acid mutation encodes for amino acid substitution Q1334H in COL4A1. In some embodiments, the nucleic acid mutation encodes for amino acid substitution G683A in COL4A2. In some embodiments, the nucleic acid mutation encodes for amino acid substitution P718S in COL4A2. In some embodiments, the nucleic acid mutation encodes for amino acid substitution R517K in COL4A2. In some embodiments, the nucleic acid mutation encodes for amino acid substitution D326Y in COL4A3. In some embodiments, the nucleic acid mutation encodes for amino acid substitution H451R in COL4A3. In some embodiments, the nucleic acid mutation encodes for amino acid substitution V1327M in COL4A4. In some embodiments, the nucleic acid mutation encodes for amino acid substitution R158Q in LOX. In some embodiments, the nucleic acid mutation encodes for amino acid substitution A1046T in AKAP13. In some embodiments, the nucleic acid mutation encodes for amino acid substitution G624V in AKAP13. In some embodiments, the nucleic acid mutation encodes for amino acid substitution G2358R in ZNF469. In some embodiments, the nucleic acid mutation encodes for amino acid substitution S158F in SLC29A3. In some embodiments, the nucleic acid mutation encodes for amino acid substitution P4493S in MUC5AC. In some embodiments, the nucleic acid mutation encodes for amino acid substitution P370S in CROCC.

In some embodiments, the nucleic acid mutation corresponds to reference SNP cluster identifier rs3742207 (e.g., SNP identified by rs3742207 in the National Center for Biotechnology Information's dbSNP database). In some embodiments, the nucleic acid mutation corresponds to reference SNP cluster identifier rs3803230. In some embodiments, the nucleic acid mutation corresponds to reference SNP cluster identifier rs9583500. In some embodiments, the nucleic acid mutation corresponds to reference SNP cluster identifier rs7990383. In some embodiments, the nucleic acid mutation corresponds to reference SNP cluster identifier rs55703767. In some embodiments, the nucleic acid mutation corresponds to reference SNP cluster identifier rs11677877. In some embodiments, the nucleic acid mutation corresponds to reference SNP cluster identifier rs2229813. In some embodiments, the nucleic acid mutation corresponds to reference SNP cluster identifier rs1800449. In some embodiments, the nucleic acid mutation corresponds to reference SNP cluster identifier rs1053411. In some embodiments, the nucleic acid mutation corresponds to reference SNP cluster identifier rs2116780. In some embodiments, the nucleic acid mutation corresponds to reference SNP cluster identifier rs3749350. In some embodiments, the nucleic acid mutation corresponds to reference SNP cluster identifier rs2286194. In some embodiments, the nucleic acid mutation corresponds to reference SNP cluster identifier rs12536657. In some embodiments, the nucleic acid mutation corresponds to reference SNP cluster identifier rs2614668. In some embodiments, the nucleic acid mutation corresponds to reference SNP cluster identifier rs745191. In some embodiments, the nucleic acid mutation corresponds to reference SNP cluster identifier rs12598474. In some embodiments, the nucleic acid mutation corresponds to reference SNP cluster identifier rs10932976. In some embodiments, the nucleic acid mutation corresponds to reference SNP cluster identifier rs5908678. In some embodiments, the nucleic acid mutation corresponds to reference SNP cluster identifier rs35803438. In some embodiments, the nucleic acid mutation corresponds to reference SNP cluster identifier rs132728. In some embodiments, the nucleic acid mutation corresponds to reference SNP cluster identifier rs132729. In some embodiments, the nucleic acid mutation corresponds to reference SNP cluster identifier rs132730 In some embodiments, the nucleic acid mutation corresponds to reference SNP cluster identifier rs859063. In some embodiments, the nucleic acid mutation corresponds to reference SNP cluster identifier rs2893276. In some embodiments, the nucleic acid mutation corresponds to reference SNP cluster identifier rs6687749. In some embodiments, the nucleic acid mutation corresponds to reference SNP cluster identifier rs13189855. In some embodiments, the nucleic acid mutation corresponds to reference SNP cluster identifier rs6876514. In some embodiments, the nucleic acid mutation corresponds to reference SNP cluster identifier rs6876515. In some embodiments, the nucleic acid mutation corresponds to reference SNP cluster identifier rs13361701. In some embodiments, the nucleic acid mutation corresponds to reference SNP cluster identifier rs883764. In some embodiments, the nucleic acid mutation corresponds to reference SNP cluster identifier rs780667. In some embodiments, the nucleic acid mutation corresponds to reference SNP cluster identifier rs780668. In some embodiments, the nucleic acid mutation corresponds to reference SNP cluster identifier rs13166148. In some embodiments, the nucleic acid mutation corresponds to reference SNP cluster identifier rs10941287. In some embodiments, the nucleic acid mutation corresponds to reference SNP cluster identifier rs7907270. In some embodiments, the nucleic acid mutation corresponds to reference SNP cluster identifier rs200922784. In some embodiments, the nucleic acid mutation corresponds to reference SNP cluster identifier rs9435793. In some embodiments, the nucleic acid mutation corresponds to reference SNP cluster identifier rs116300974. In some embodiments, the nucleic acid mutation corresponds to reference SNP cluster identifier rs2233696.

In some embodiments and in accordance with any of the above, the stem cell is obtained from an autologous or homologous donor. In some embodiments, the method includes obtaining stem cells comprising the nucleic acid mutation in a corneal dystrophy target nucleic acid from the subject.

In certain embodiments and in accordance with any of the above, the plurality of stem cells are limbal epithelial stem cells, oral mucosal epithelial stem cells, dental stem cells, hair follicle stem cells, mesenchymal stem cells, umbilical cord lining stem cells, or embryonic stem cells. In certain embodiments, the cells of the plurality of stem cells are limbal epithelial stem cells.

In some embodiments, the set of nucleic acid manipulation reagents comprise a zinc finger nuclease, a transcription activator-like effector nuclease (TALENs), a reengineered homing nuclease, a RNA interference (RNAi) reagent, or Clustered Regularly Interspaced Short Palindromic Repeats (CRISPR)/nuclease system reagents.

In particular embodiments, the nucleic acid manipulation reagents are Clustered Regularly Interspaced Short Palindromic Repeats (CRISPR)/nuclease system reagents that include: a) a guide RNA nucleic acid that hybridizes with the corneal dystrophy target nucleic acid within a DNA molecule of the plurality of stem cells; and b) a nuclease nucleic acid encoding a nuclease. In such embodiments, the guide RNA targets (e.g., hybridizes with) the target nucleic acid and the nuclease cleaves the DNA molecule. In some embodiments, the CRISPR/nuclease system reagents further include c) a repair nucleic acid comprising a wild type version of the corneal dystrophy target nucleic acid or fragment thereof. In such embodiments, the guide RNA hybridizes with the target nucleic acid and the nuclease cleaves the DNA molecule thereby creating a target nucleic acid cleavage site, whereby the repair nucleic acid is capable of homologously recombining with the corneal dystrophy target nucleic acid after the creation of the target nucleic acid cleavage site. In some embodiments, the guide RNA and/or repair nucleic acid comprises a detectable label. In particular embodiments, the detectable label is a nucleic acid barcode or fluorescent barcode label. In some embodiments, the corneal dystrophy target nucleic acid is a TGFβI target nucleic acid. In other embodiments, the corneal dystrophy target nucleic acid is COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1 target nucleic acid. In some embodiments, two or more of COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1 target nucleic acids are manipulated. In some embodiments, the TGFβI target nucleic acid and one or more target nucleic acids selected from the group consisting of COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, and PLP1 target nucleic acids are manipulated.

In some embodiments, the CRISPR/nuclease system reagents further comprise one or more agents that increase frequency of homologous recombination in the plurality of stem cells by repressing genes involved in non-homologous end joining (NHEJ) pathway. In certain embodiments, the nuclease is a Cas9 nuclease.

In exemplary embodiments and in accordance with any of the above, the corneal dystrophy occurs following laser eye surgery.

In further embodiments and in accordance with any of the above, the method further includes establishing a stable cell line from the isolated one or more manipulated stem cells.

In some embodiments, the method further includes repeating d) transplanting the one or more manipulated stem cells into the subject at one or more predetermined frequencies (e.g., weekly, monthly, quarterly, biannually, annually, etc.).

In a second aspect, provided herein is a kit for the treatment of corneal dystrophy in a subject in need thereof. The kit includes: a guide RNA nucleic acid that hybridizes with a corneal dystrophy target nucleic acid; and a nuclease nucleic acid encoding a nuclease. In some embodiments, the kit also includes a repair nucleic acid comprising a wild type version of the corneal dystrophy target nucleic acid or fragment thereof.

BRIEF DESCRIPTION OF THE DRAWINGS

For a better understanding of the aforementioned implementations of the subject systems and methods as well as additional implementations thereof, reference should be made to the Description of Implementations below, in conjunction with the following drawings in which like reference numerals refer to corresponding parts throughout the figures.

FIG. 2 is a chart showing exemplary mutations that can be repaired using the subject methods provided herein.

FIG. 8A discloses SEQ ID NOS 25-28, respectively, in order of appearance. FIG. 8B discloses SEQ ID NOS 29-32, respectively, in order of appearance. FIG. 8C discloses SEQ ID NOS 33 36, respectively, in order of appearance FIG. 9A discloses SEQ ID NOS 37-38, FIG. 9B discloses SEQ ID NOS 37 and 39, FIG. 9C discloses SEQ ID NOS 40-41, FIG. 9D discloses SEQ ID NOS 40 and 42, FIG. 9E discloses SEQ ID NOS 43-44, and FIG. 9F discloses SEQ ID NOS 43 and 45, respectively, in order of appearance.

FIG. 11 illustrates exemplary sgRNA sequence, nucleotide and amino acid sequences of Cas9 nuclease from *Streptococcus pyogenes* (Spy) and *Staphylococcus aureus* (Sau).

DETAILED DESCRIPTION

I. Introduction

Corneal dystrophies are a group of hereditary disorders characterized by bilateral abnormal deposition of substances in the cornea, the transparent front part of the eye. A subset of such corneal dystrophies, epithelial-stromal corneal dystrophies, is known to be associated with mutations in transforming growth factor beta induced (TGFβI) gene. The TGFβI gene encodes an RGD-containing protein that binds to type I, II and IV collagens.

In some cases, epithelial-stromal corneal dystrophies distinguished from each other and are divided into subtypes on the basis of the clinical appearance of the opacities, clinical features of the disease, and on histopathological staining properties of the deposits. Without being bound by any particular theory of operation it is believed that specific mutations in the TGFβI gene account for the specific phenotypes associated with such corneal dystrophies and that the corneal opacities that account for the clinical features of the different phenotypes result from the deposition of all or part of the mutated encoded TGFβI protein.

Stem cell-based therapy for tissue repair and regeneration provides promising treatments for a number of ocular disorders, include corneal dystrophies. Stem cells are capable of self-renewal and differentiation to generate a variety of mature cell lineages. Transplantation of such cells can be utilized as a clinical tool for reconstituting a target tissue (e.g., corneal tissue), thereby restoring physiological and anatomic functionality.

Advances in the development of nucleic acid manipulation reagents have allowed for simple and efficient manipulation of nucleic acids (e.g., DNA and RNA) in stem cells. The development of CRISPR reagents have provide DNA-encoded, RNA mediated, DNA- or RNA-targeting sequence specific targeting. CRISPR systems can be used, for example, for the precise insertion of donor DNA into a target cell genome. Such nucleic acid manipulation reagents have enabled researchers to precisely manipulate specific genomic elements.

The present disclosure is based at least in part on the discovery of methods for the treatment of ocular diseases using a stem cell based approach. In particular embodiments, stem cells isolated from a subject undergoing a treatment for an ocular dystrophy are obtained and genetically modified using CRISPR system reagents to correct a mutant allele associated with the ocular disease.

Figure 1:
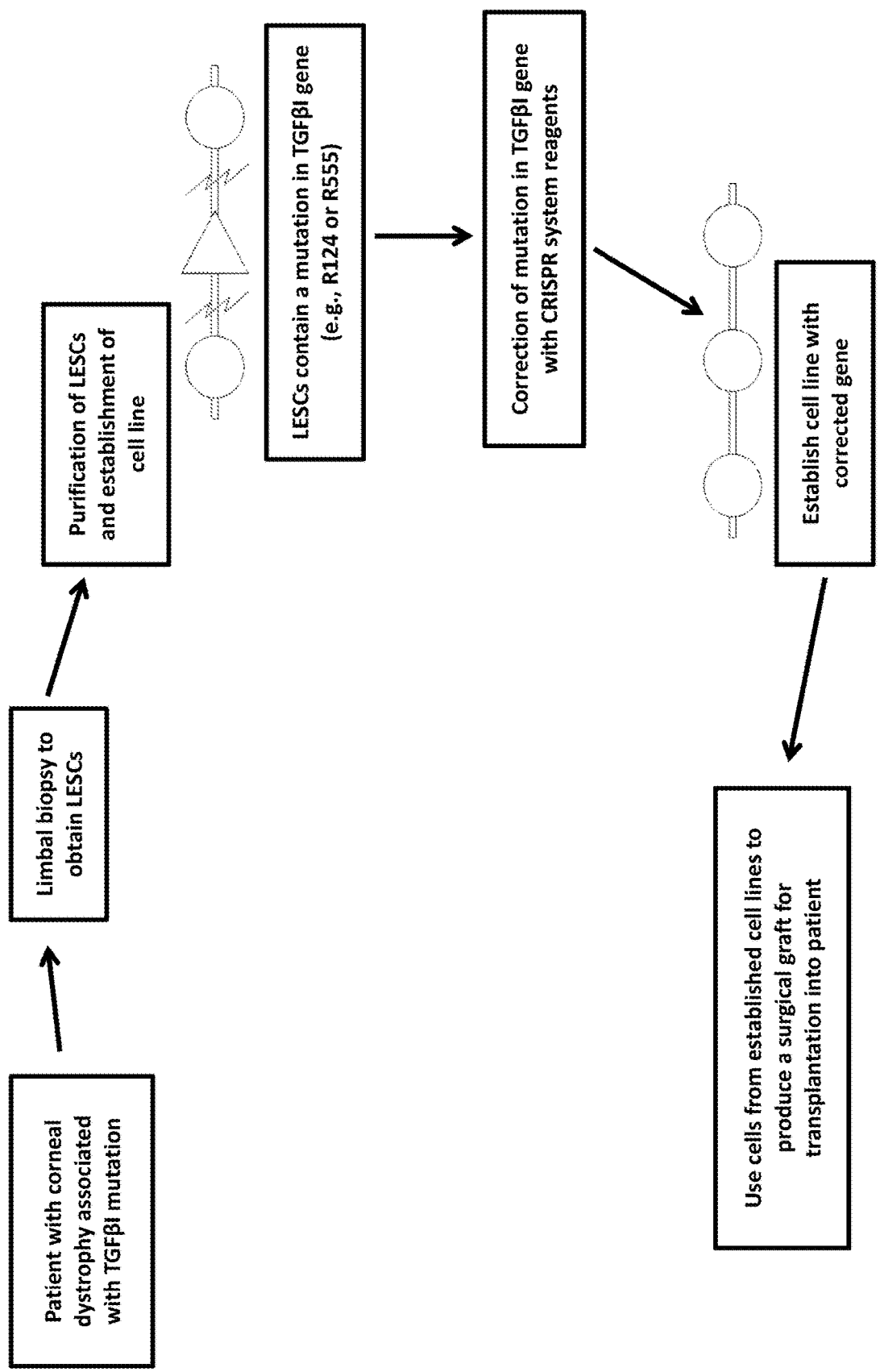
FIG. 1 is a diagram showing a schematic of one particular embodiment of the subject methods described herein.

In one aspect, provided herein is a method for the treatment of a corneal dystrophy (e.g., FIG. 1). The method, for example, includes manipulating a nucleic acid mutation in a corneal dystrophy target nucleic acid in a stem cell from the subject to correct the nucleic acid mutation, thereby forming a manipulated stem cell; and transplanting the manipulated stem cell into the subject. In some embodiments, the method may include the steps of obtaining a plurality of stem cells that include nucleic acid mutation in a target corneal dystrophy nucleic acid from the subject; b) manipulating the nucleic acid mutation in one or more stem cells of the plurality of stem cells to correct the nucleic acid mutation, thereby forming one or more manipulated stem cells; c) isolating the one or more manipulated stem cells; and d) transplanting the one or more manipulated stem cells into the subject. Features of the subject method are discussed further in detail below.

II. Corneal Dystrophies

The methods provided herein are for the treatment of one or more corneal dystrophies in a subjects in need thereof. Subjects that can be treated with the methods include, but are not limited to, mammalian subjects such as a mouse, rat, dog, baboon, pig or human. In some embodiments, the subject is a human. The methods can be used to treat subjects at least 1 year, 2 years, 3 years, 5 years, 10 years, 15 years, 20 years, 25 years, 30 years, 35 years, 40 years, 45 years, 50 years, 55 years, 60 years, 65 years, 70 years, 75 years, 80 years, 85 years, 90 years, 95 years or 100 years of age.

As used herein, a "corneal dystrophy" refers to any one of a group of hereditary disorders in the outer layer of the eye (cornea). For example, the corneal dystrophy may be characterized by bilateral abnormal deposition of substances in the cornea. Corneal dystrophies include, but are not limited to the following four IC3D categories of corneal dystrophies (see, e.g., Weiss et al., Cornea 34(2): 117-59 (2015)): epithelial and subepithelial dystrophies, epithelial-stromal TGFβI dystrophies, stromal dystrophies and endothelial dystrophies. In some embodiments, the corneal dystrophy is selected from the group consisting of Epithelial basement membrane dystrophy (EBMD), Meesmann corneal dystrophy (MECD), Thiel-Behnke corneal dystrophy (TBCD), Lattice corneal dystrophy (LCD), Granular corneal dystrophy (GCD), and Schnyder corneal dystrophy (SCD). In additional embodiments, the corneal dystrophy herein excludes MECD.

In additional embodiments, the corneal dystrophy is caused by one or more mutations, such as SNP, for example, including those located in a gene selected from the group consisting of Transforming growth factor, beta-induced (TGFBI), keratin 3 (KRT3), keratin 12 (KRT12), GSN, and UbiA prenyltransferase domain containing 1 (UBIAD1). In further embodiments, the SNP site results in encoding a mutant amino acid in a mutant protein as shown herein. In further embodiments, a mutant sequence comprising the SNP site encodes a mutant protein selected from the group consisting of (i) mutant TGFBI proteins comprising a mutation corresponding to Leu509Arg, Arg666Ser, Gly623Asp, Arg555Gln, Arg124Cys, Val505Asp, Ile522Asn, Leu569Arg, His572Arg, Arg496Trp, Pro501Thr, Arg514Pro, Phe515Leu, Leu518Pro, Leu518Arg, Leu527Arg, Thr538Pro, Thr538Arg, Val539Asp, Phe540del, Phe540Ser, Asn544Ser, Ala546Thr, Ala546Asp, Phe547Ser, Pro551Gln, Leu558Pro, His572del, Gly594Val, Val613del, Val613Gly, Met619Lys, Ala620Asp, Asn622His, Asn622Lys, Asn622Lys, Gly623Arg, Gly623Asp, Val624 Val625del, Val624Met, Val625Asp, His626Arg, His626Pro, Val627SerfsX44, Thr629_Asn630insAsnValPro, Val631Asp, Arg666Ser, Arg555Trp, Arg124Ser, Asp123delins, Arg124His, Arg124Leu, Leu509Pro, Leu103_Ser104del, Val113Ile, Asp123His, Arg124Leu, and/or Thr125_Glu126del in TGFBI, for example, of Protein Accession No. Q15582; (ii) mutant KRT3 proteins comprising a mutation corresponding to Glu498Val, Arg503Pro, and/or Glu509Lys in Keratin 3 protein, for example, of Protein Accession No. P12035 or NP 476429.2; (iii) mutant KRT12 proteins with Met129Thr, Met129Val, Gln130Pro, Leu132Pro, Leu132Va, Leu132His, Asn133Lys, Arg135Gly, Arg135Ile, Arg135Thr, Arg135Ser, Ala137Pro, Leu140Arg, Val143Leu, Va1143Leu, Lle391Leu399dup, Ile426Val, Ile 426Ser, Tyr429Asp, Tyr429Cys, Arg430Pro, and/or Leu433Arg in KRT12, for example, of Protein Accession No. Q99456.1 or NP 000214.1; (iv) mutant GSN proteins with Asp214Tyr in GSN, for example, of Protein Accession No. P06396; and (v) mutant UBIAD1 proteins comprising a mutation corresponding to Ala97Thr, Gly98Ser, Asn102Ser, Asp112Asn, Asp112Gly, Asp118Gly, Arg119Gly, Leu121Val, Leu121Phe, Val122Glu, Val122Gly, Ser171Pro, Tyr174Cys, Thr175Ile, Gly177Arg, Lys181Arg, Gly186Arg, Leu188His, Asn232Ser, Asn233His, Asp236Glu, and/or Asp240Asn in UBIAD1, for example, of Protein Accession No. Q9Y5Z9. For example, a mutant sequence comprising the SNP site encodes at least a part of mutant TGFBI protein mutated by replacing Leu with Arg at amino acid position corresponding to the amino acid position 509 of Protein Accession No. Q15582. In case, a mutation at the SNP site may be responsible for encoding the mutant amino acid at amino acid position corresponding to the amino acid position 509 of Protein Accession No. Q15582. As used herein, a mutation "corresponding to" a particular mutation in a human protein may include a mutation in a different species that occur at the corresponding site of the particular mutation of the human protein. Also as used herein, when a mutant protein is described to include a particular mutant, for example, of Leu509Arg, such a mutant protein may comprise any mutation that occurs at a mutant site corresponding to the particular mutant in a relevant human protein, for example, in TGFBI protein of Protein Accession No. Q15582 as described herein.

In some embodiments, the mutant described herein excludes any mutant in KRT12 protein. In some embodiments, the mutant described herein excludes a mutation corresponding to Leu132Pro in KRT12, for example, of Protein Accession No. Q99456.1. In further embodiments, the SNP described herein excludes any SNP that occurs in KRT12 gene. In yet further embodiments, the SNP described herein excludes any SNP that results in the Leu132Pro mutation in KRT12 protein. The SNP may further exclude the SNP at a PAM site (AAG>AGG) that results in the Leu132Pro mutation in KRT12 protein.

Epithelial-stromal corneal dystrophies include Reis-Bucklers corneal dystrophy, Thiel-Behnke corneal dystrophy, lattice corneal dystrophy type 1, granular corneal dystrophy type 1, and granular corneal dystrophy type 2. Stromal corneal dystrophies include macular corneal dystrophy, Schnyder corneal dystrophy, congenital stromal corneal dystrophy, posterior amorphous corneal dystrophy, central cloudy dystrophy of Francois, and pre-Descemet corneal dystrophy. In some embodiments, the methods are for the treatment of an epithelial-stromal corneal dystrophy. In some embodiments, the corneal dystrophy is Reis-Bucklers corneal dystrophy. In certain embodiments, the corneal dystrophy is Thiel-Behnke corneal dystrophy. In certain embodiments, the corneal dystrophy is lattice corneal dystrophy type 1. In certain embodiments, the corneal dystrophy is granular corneal dystrophy type 1. In certain embodiments, the corneal dystrophy is granular corneal dystrophy type 2. Epithelial-stromal dystrophies are caused by mutations in TGFβI. As used herein "Transforming growth factor, beta-induced," "TGFBI," "TGFβI," "BIGH3," "CDB1," "CDG2," "CDG1," "CSD," "CSD1," "CSD2," "CSD3," "EBMD," and "LCD1" all refer to an RGD-containing protein that binds to type I, II, and IV collagens (Accession Numbers: NM_00358 and MP 000349 (human) and NM_009369 and MP 033395 (mouse)). In humans, TGFβI is encoded by the TGFBI gene, locus 5q31. The RGD motif is found in many extracellular matrix proteins modulating cell adhesion and serves as a ligand recognition sequence for several integrins. TGFβI is induced by transforming growth factor-beta and acts to inhibit cell adhesion. In epithelial-stromal dystrophies, mutations in the TGFBI gene, the TGFβI structure is abnormal and accumulation of the insoluble mutant TGFβI or its proteolytic fragment occurs in the cornea.

In other embodiments, the subject has granular corneal dystrophy type II. As used herein, "granular corneal dystrophy type II," "Avellino corneal dystrophy," "granular corneal dystrophy type 2" and "combined granular-lattice corneal dystrophy" all refer to an autosomal dominant form of granular corneal dystrophy that is caused by a mutation in the TGFBI gene, local on chromosome 5q31. In some cases, granular corneal dystrophy type II is characterized by irregular-shaped well-demarcated granular deposits in the superficial central corneal stroma, and progressive visual impairment. Heterozygous patients suffering from granular corneal dystrophy type II have increasing loss in vision with age, becoming severe in the later years of life. Lesions appear within the first decade of life and may be evident by 3 years of age. Onset of granular corneal dystrophy type II is generally earlier in homozygous patients and may accompany mild corneal erosions. Visual acuity usually remains good until late in the course of the condition. Opacities are initially small superficial whitish dots. Subsequently, ring or stellate-shaped stromal opacities develop. Final-stage opacities are more superficial and translucent, and may coalesce in the anterior stroma.

In some embodiments, the subject has keratoconus. Keratoconus (KTCN) is the most common corneal ectatic disorder with approximately 6-23.5% of subjects carrying a positive family history (Wheeler, J., Hauser, M. A., Afshari, N. A., Allingham, R. R., Liu, Y., *Reproductive Sys Sexual Disord* 2012; S: 6). The reported prevalence of KTCN ranges from 8.8 to 54.4 per 100,000. variation in prevalence is partly due to the different criteria used to diagnose the disease. (Wheeler, J., Hauser, M. A., Afshari, N. A., Allingham, R. R., Liu, Y., *Reproductive Sys Sexual Disord* 2012; S: 6; and Nowak, D., Gajecka, M., *Middle East Afr J Ophthalmol* 2011; 18(1): 2-6). Many studies exist within the literature that attempt to define the genetic causes of KTCN. These studies have uncovered numerous possible genetic variants or SNPs that are believed to contribute to the etiology of the disease depending on the experimental parameters.

Previously, it was discovered that heterozygous individuals were highly susceptible to accelerating loss of vision following LASIK laser eye surgery. Notably, two years after surgery increased opacity of the cornea was observed in these patients with increasing aggressiveness, eventually resulting in complete loss of vision (Jun, R. M. et al., *Opthalmology,* 111:463, 2004). Previously, eye surgery has been performed with an expectation that LASIK or Excimer Laser surgery would get rid of vision blurriness of a patient suffering from corneal dystrophy. For a hypothetical number of three hundred thousand cases of LASIK surgery, 300 people would have lost their vision, based on 1/1000 of minimum estimation of heterozygous patients suffering from granular corneal dystrophy type II. Patients who have undergone LASIK surgery are mainly in their 20's and 30's carrying out productive activities. In addition, after approval of LASIK surgery in year 2000 in USA, African American patients suffering from granular corneal dystrophy type II who underwent LASIK surgery have been found to lose eye sight, which infers that plenty of similar cases might be occurring throughout the world.

In some embodiments, the subject having granular corneal dystrophy type II is homozygous for a mutation in TGFβI. In other embodiments, the subject having granular corneal dystrophy type II is heterozygous for a mutation in TGFβI. In some embodiments, the subject has a mutation that encodes for a substitution of arginine 124, arginine 555, or histidine 626 in a TGFβI polypeptide. In particular embodiments, the nucleic acid mutation encodes for an amino acid substitution selection from R124C, R124H, R124L, R555W, R555Q, and H626P.

In certain embodiments, the subject undergoing treatment has granular corneal dystrophy type I and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has granular corneal dystrophy type I and is at least 5, 10, 15, 20, 25, 30, 35, 40, 45, 50, 55, 65, 70, 75, 80, 85, 90, 95, or 100 years old.

In certain embodiments, the subject undergoing treatment has granular corneal dystrophy type II and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has granular corneal dystrophy type II and is at least 5, 10, 15, 20, 25, 30, 35, 40, 45, 50, 55, 65, 70, 75, 80, 85, 90, 95, or 100 years old.

In certain embodiments, the subject undergoing treatment has lattice corneal dystrophy type 1 and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has lattice corneal dystrophy type 1 and is at least 5, 10, 15, 20, 25, 30, 35, 40, 45, 50, 55, 65, 70, 75, 80, 85, 90, 95, or 100 years old.

In certain embodiments, the subject undergoing treatment has Reis-Bucklers corneal dystrophy and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has Reis-Bucklers corneal dystrophy and is at least 5, 10, 15, 20, 25, 30, 35, 40, 45, 50, 55, 65, 70, 75, 80, 85, 90, 95, or 100 years old.

In certain embodiments, the subject undergoing treatment has Thiel-Behnke corneal dystrophy and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has Thiel-Behnke corneal dystrophy and is at least 5, 10, 15, 20, 25, 30, 35, 40, 45, 50, 55, 65, 70, 75, 80, 85, 90, 95, or 100 years old.

In some embodiments, the subject has keratoconus and is homozygous for a mutation in one of the following corneal target nucleic acids: COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1. In other embodiments, the subject has keratoconus and is heterozygous for a mutation in one of the following corneal target nucleic acids: COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1.

In some embodiments, the subject has a nucleic acid mutation that encodes for amino acid substitution Q1334H in COL4A1. In some embodiments, the subject has a nucleic acid mutation that encodes for amino acid substitution G683A in COL4A2. In some embodiments, the subject has a nucleic acid mutation that encodes for amino acid substitution P718S in COL4A2. In some embodiments, the subject has a nucleic acid mutation that encodes for amino acid substitution R517K in COL4A2. In some embodiments, the subject has a nucleic acid mutation that encodes for amino acid substitution D326Y in COL4A3. In some embodiments, the subject has a nucleic acid mutation that encodes for amino acid substitution H451R in COL4A3. In some embodiments, the subject has a nucleic acid mutation that encodes for amino acid substitution V1327M in COL4A4. In some embodiments, the subject has a nucleic acid mutation that encodes for amino acid substitution R158Q in LOX. In some embodiments, the subject has a nucleic acid mutation that encodes for amino acid substitution A1046T in AKAP13. In some embodiments, the subject has a nucleic acid mutation that encodes for amino acid substitution G624V in AKAP13. In some embodiments, the subject has a nucleic acid mutation that encodes for amino acid substitution G2358R in ZNF469. In some embodiments, the subject has a nucleic acid mutation that encodes for amino acid substitution S158F in SLC29A3. In some embodiments, the subject has a nucleic acid mutation that encodes for amino acid substitution P4493S in MUC5AC. In some embodiments, the subject has a nucleic acid mutation that encodes for amino acid substitution P370S in CROCC.

In some embodiments, the subject has a nucleic acid mutation that corresponds to reference SNP cluster identifier rs3742207 (e.g., SNP identified by rs3742207 in the National Center for Biotechnology Information's dbSNP database). In some embodiments, the subject has a nucleic acid mutation that corresponds to reference SNP cluster identifier rs3803230. In some embodiments, the subject has a nucleic acid mutation that corresponds to reference SNP cluster identifier rs9583500. In some embodiments, the subject has a nucleic acid mutation that corresponds to reference SNP cluster identifier rs7990383. In some embodiments, the subject has a nucleic acid mutation that corresponds to reference SNP cluster identifier rs55703767. In some embodiments, the subject has a nucleic acid mutation that corresponds to reference SNP cluster identifier rs11677877. In some embodiments, the subject has a nucleic acid mutation that corresponds to reference SNP cluster identifier rs2229813. In some embodiments, the subject has a nucleic acid mutation that corresponds to reference SNP cluster identifier rs1800449. In some embodiments, the subject has a nucleic acid mutation that corresponds to reference SNP cluster identifier rs1053411. In some embodiments, the subject has a nucleic acid mutation that corresponds to reference SNP cluster identifier rs2116780. In some embodiments, the subject has a nucleic acid mutation that corresponds to reference SNP cluster identifier rs3749350. In some embodiments, the subject has a nucleic acid mutation that corresponds to reference SNP cluster identifier rs2286194. In some embodiments, the subject has a nucleic acid mutation that corresponds to reference SNP cluster identifier rs12536657. In some embodiments, the subject has a nucleic acid mutation that corresponds to reference SNP cluster identifier rs2614668. In some embodiments, the subject has a nucleic acid mutation that corresponds to reference SNP cluster identifier rs745191. In some embodiments, the subject has a nucleic acid mutation that corresponds to reference SNP cluster identifier rs12598474. In some embodiments, the subject has a nucleic acid mutation that corresponds to reference SNP cluster identifier rs10932976. In some embodiments, the subject has a nucleic acid mutation that corresponds to reference SNP cluster identifier rs5908678. In some embodiments, the subject has a nucleic acid mutation that corresponds to reference SNP cluster identifier rs35803438. In some embodiments, the subject has a nucleic acid mutation that corresponds to reference SNP cluster identifier rs132728. In some embodiments, the subject has a nucleic acid mutation that corresponds to reference SNP cluster identifier rs132729. In some embodiments, the subject has a nucleic acid mutation that corresponds to reference SNP cluster identifier rs132730 In some embodiments, the subject has a nucleic acid mutation that corresponds to reference SNP cluster identifier rs859063. In some embodiments, the subject has a nucleic acid mutation that corresponds to reference SNP cluster identifier rs2893276. In some embodiments, the subject has a nucleic acid mutation that corresponds to reference SNP cluster identifier rs6687749. In some embodiments, the subject has a nucleic acid mutation that corresponds to reference SNP cluster identifier rs13189855. In some embodiments, the subject has a nucleic acid mutation that corresponds to reference SNP cluster identifier rs6876514. In some embodiments, the subject has a nucleic acid mutation that corresponds to reference SNP cluster identifier rs6876515. In some embodiments, the subject has a nucleic acid mutation that corresponds to reference SNP cluster identifier rs13361701. In some embodiments, the subject has a nucleic acid mutation that corresponds to reference SNP cluster identifier rs883764. In some embodiments, the subject has a nucleic acid mutation that corresponds to reference SNP cluster identifier rs780667. In some embodiments, the subject has a nucleic acid mutation that corresponds to reference SNP cluster identifier rs780668. In some embodiments, the subject has a nucleic acid mutation that corresponds to reference SNP cluster identifier rs13166148. In some embodiments, the subject has a nucleic acid mutation that corresponds to reference SNP cluster identifier rs10941287. In some embodiments, the subject has a nucleic acid mutation that corresponds to reference SNP cluster identifier rs7907270. In some embodiments, the subject has a nucleic acid mutation that corresponds to reference SNP cluster identifier rs200922784. In some embodiments, the subject has a nucleic acid mutation that corresponds to reference SNP cluster identifier rs9435793. In some embodiments, the subject has a nucleic acid mutation that corresponds to reference SNP cluster identifier rs116300974. In some embodiments, the subject has a nucleic acid mutation that corresponds to reference SNP cluster identifier rs2233696.

In certain embodiments, the subject undergoing treatment has keratoconus and is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 years old. In some embodiments, the subject undergoing treatment has keratoconus and is at least 5, 10, 15, 20, 25, 30, 35, 40, 45, 50, 55, 65, 70, 75, 80, 85, 90, 95, or 100 years old.

In certain embodiments, the subject undergoing the subject treatment has granular corneal dystrophy type II and has also undergone laser eye surgery. In some embodiments, the treatment is performed 6 months or less, 1 year or less, 1.5 years or less, 2 years or less, 2.5 years or less, 3 years or less, 3.5 years or less, 4 years or less, 4.5 years or less, 5 years or less, 5.5 years or less, 6 years or less, 6.5 years or less, 7 years or less, 7.5 years or less, 8 years or less, 8.5 years or less, 9 years or less, 9.5 years or less, 10 years or less, 15 years or less, 20 years or less 25 years or less, 30 years or less, 35 years or less, 40 years or less, 45 years or less, 50 years or less, 55 years or less, 60 years or less, 65 years or less, 70 years or less, 75 years or less, 80 years or less, 85 years or less, 90 years or less, 95 years or less or 100 years or less following laser eye surgery.

In some embodiments of the methods provided herein, therapy is used to provide a positive therapeutic response with respect to a disease or condition (e.g., a corneal dystrophy). By "positive therapeutic response" is intended an improvement in the disease or condition, and/or an improvement in the symptoms associated with the disease or condition. The therapeutic effects of the subject methods of treatment can be assessed using any suitable method. In certain embodiments, treatment is assessed by the reduction of protein deposition on the cornea of the subject after treatment as compare to a control (e.g., the amount of protein deposition prior to treatment). In some embodiments, the subject methods reduce the amount of corneal protein deposition in the subject by at least 5%, 10%, 15%, 20%, 25%, 30%, 35%, 40%, 45%, 50%, 55%, 60%, 65%, 70%, 75%, 80%, 85%, 90%, 95%, or 99% as compared to the cornea prior to undergoing treatment. Corneal opacity can also be used to assess the therapeutic effect using the subject methods. Further, in some embodiments, treatment is assessed by visual function. Assessment of visual function in the subject can be carried out using any suitable test known in the art including, but not limited to, assessments of uncorrected visual acuity (UCVA), best-corrected visual acuity (BCVA) and brightness acuity test (BAT). See, e.g., Awaad et al., Am J Ophthalmol. 145(4): 656-661 (2008) and Sharhan et al., Br J Ophthalmol 84:837-841 (2000), which are incorporated by reference in their entirety for all purposes, and particularly for all teachings relating to standards for assessing visual acuity. In certain embodiments, the subject's visual acuity improves by at least 5%, 10%, 15%, 20%, 25%, 30%, 35%, 40%, 45%, 50%, 55%, 60%, 65%, 70%, 75%, 80%, 85%, 90%, 95%, or 99% as compared prior to undergoing treatment.

In some embodiments, the subject is tested for one or more corneal dystrophies. In some embodiments, the subject is tested for a nucleic acid mutation, such as SNP, associated with corneal dystrophy described herein.

For example, the subject is tested for a nucleic acid mutation in a target TGFβI nucleic acid. In certain embodiments, the subject is tested for a nucleic acid mutation encoding for an amino acid substitution of arginine 124, arginine 555, or histidine 626 in a TGFβI polypeptide. In some embodiments, the nucleic acid mutation encodes for an amino acid substitution selection from R124C, R124H, R124L, R555W, R555Q, and H626P. For example, buccal cells of the subject are collected using a buccal swab. The collected buccal cells are analyzed for the presence of one or more nucleic acid mutations encoding for an amino acid substitution of arginine 124, arginine 555, or histidine 626 in a TGFβI polypeptide. In some embodiments, corneal dystrophy is detected, for example, through detection of Avellino corneal dystrophy-related single nucleotide polymorphisms (SNPs), such as those that result in R124 mutations in the TGFβI gene (including for example but not limited to an R124H mutation caused by a G to A transition at nucleotide 418 of TGFβI gene also referred to as a C(G/A)C SNP). In some embodiments, corneal dystrophy is detected for example through detection of granular corneal dystrophy-related SNPs, such as those that result in R555 mutations in the TGFβI gene (including for example but not limited to an R555W mutation caused by a C to T transition at nucleotide 1663 of TGFβI gene also referred to as a (C/T)GG SNP). In some embodiments, corneal dystrophy is detected for example through detection of lattice dystrophy-related SNPs, such as those that result in R124 and/or 626 mutations in the TGFβI gene (including for example but not limited to an R124C mutation caused by a C to T transition at nucleotide 417 of TGFβI gene also referred to as a (C/T)GC SNP or a H626P mutation caused by an A to C transition at nucleotide 1924 of TGFβI gene. In some embodiments, corneal dystrophy is detected for example through detection of Reis-Buckler corneal dystrophy-related SNPs, such as those that result in R124 mutations in the TGFβI gene (including for example but not limited to an R124L mutation caused by a G to T transition at nucleotide 418 of TGFβI gene also referred to as a C(G/T)C SNP). In some embodiments, corneal dystrophy is detected for example through detection of Thiel-Behnke corneal dystrophy-related SNPs, such as those that result in R555 mutations in the TGFβI gene (including for example but not limited to an R555Q mutation caused by a G to A transition at nucleotide 1664 of TGFβI gene also referred to as a C(G/A)G SNP). In some embodiments, the subject is tested for a nucleic acid mutation in a corneal dystrophy target nucleic acid associated with keratoconus. In certain embodiments, the corneal dystrophy target nucleic acid is COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1.

In some embodiments, the subject is tested for one or more corneal dystrophies prior to transplanting one or more manipulated stem cells into the subject.

III. Stem Cells

The subject methods include obtaining a plurality of stem cells. Any suitable stem cells can be used for the subject method, depending on the type of corneal dystrophy to be treated. In certain embodiments, the stem cell is obtained from an autologous, homologous or heterologous donor. When the stem cell is obtained from the heterologous donor, the stem cells of the heterologous donor and the subject to be treated are donor-recipient histocompatible. In certain embodiments, autologous stem cells are obtained from the subject in need of the treatment for corneal dystrophy. Obtained stem cells carry a mutation in a gene associated with the particular corneal dystrophy to be treated (e.g., stem cells having a mutation in a TGFBI gene of a subject having an epithelial-stromal dystrophy, as discussed above). Suitable stem cells include, but are not limited to, dental pulp stem cells, hair follicle stem cells, mesenchymal stem cells, umbilical cord lining stem cells, embryonic stem cells, oral mucosal epithelial stem cells and limbal epithelial stem cells.

In some embodiments, the plurality of stem cells includes limbal epithelial stem cells. Limbal epithelial stem cells (LESCs) are located in the limbal region of the cornea and are responsible for the maintenance and repair of the corneal surface. Without being bound by any particular theory of operation, it is believed that LESCs undergo asymmetric cell division producing a stem cell that remains in the stem cell niche to repopulate the stem cell pool, and a daughter early transient amplifying cell (eTAC). more differentiated eTAC is removed from the stem cell niche and is able to divide to further produce transient amplifying cells (TAC), eventually giving rise to terminally differentiated cells (DC). LESCs can be obtained, for example, by taking a biopsy from the subject's eye. See, e.g., Pellegrini et al., *Lancet* 349: 990-

993 (1997). LESCs obtained from limbal biopsies can be isolated and sorted for use in the subject methods using any suitable technique including, but not limited to, fluorescence activated cell sorting (FACS) and centrifugation techniques. LESCs can be sorted from biopsies using positive expression of stem cell associated markers and negative expression of differentiation markers. Positive stem cell markers include, but are not limited to, transcription factor p63, ABCG2, C/EBPδ and Bmi-1. Negative corneal specific markers include, but are not limited to, cytokeratin 3 (CK3), cytokeratin 12 (CK12), connexin 43, and involucrin. In some embodiments, the plurality of stem cells is positive for expression of p63, ABCG2 or combinations thereof. In certain embodiments, at least 65%, 70%, 75%, 80%. 85%, 86%. 88%. 89%, 90%, 91%, 92%, 93%, 94%, 95%, 96%, 97%, 98% or 99% of the cells in the plurality of stem cells express p63, ABCG2, C/EBPδ and Bmi-1 or combinations thereof. In some embodiments, the plurality of stem cells is negative for expression of CK3, CK12, connexin 43, involucrin or combinations thereof. In certain embodiments, at least 65%, 70%, 75%, 80%. 85%, 86%. 88%. 89%, 90%, 91%, 92%, 93%, 94%, 95%, 96%, 97%, 98% or 99% of the cells in the plurality of stem cells do not express CK12, connexin 43, involucrin or combinations thereof. Other markers useful for LESC are described, for example, in Takacs et al., *Cytometry A* 75: 54-66 (2009), which is incorporated by reference in its entirety for all purposes, and particularly for all teachings relating to LESC markers. Stem cell features such as cell size and high nuclear to cytoplasmic ratio can also be used to aid in the identification of LESCs.

In addition to LESCs, other stem cells isolated from the subject's cornea can also be used with the subject methods. Exemplary corneal stem cells include, but are not limited to, stromal stem cells, stromal fibroblast-like cells, stromal mesenchymal cells, neural crest derived corneal stem cells, and putative endothelial stem cells.

In some embodiments, the cells used with the methods described herein are stromal stem cells obtained from a subject's cornea. For example, stromal stem cells can be isolated using any suitable method including, but not limited to, those described in Funderburgh et al., *FASEB J* 19: 1371-1373 (2005); Yoshida et al., *Invest Ophtalmol Vis* Sci 46: 1653-1658 (2005); Du et al. *Stem Cells* 1266-1275 (2005); Dravida et al., *Brain Res Dev Brain Res* 160:239-251 (2005); and Polisetty et al. *Mol Vis* 14: 431-442 (2008), which are incorporated by reference in their entirety for all purposes, and particularly for all teaching relating to the isolation and culturing of various stromal stem cells.

Markers that are characteristic of these stromal stem cells include, but are not limited to, Bmi-1, Kit, Notch-1, Six2, Pax6, ABCG2, Spag10, and p62/OSIL. In some embodiments, at least 65%, 70%, 75%, 80%. 85%, 86%. 88%. 89%, 90%, 91% 92%, 93%, 94%, >95%, 96%, 97%, 98% or 99% of cells in the plurality of stem cells express Bmi-1, Kit, Notch-1, Six2, Pax6, ABCG2, Spag10, or p62/OSIL or combinations thereof. In certain embodiments, the stromal stem cells are positive for CD31, SSEA-4, CD73, CD105 and negative for CD34, CD45, CD123, CD133, CD14, CD106 and HLA-DR. In certain embodiments, at least 65%, 70%, 75%, 80%. 85%, 86%. 88%. 89%, 90%, 91% 92%, 93%, 94%, 95%, 96%, 97%, 98% or 99% of cells in the plurality of stem cells are positive for CD31, SSEA-4, CD73, CD105 and negative for CD34, CD45, CD123, CD133, CD14, CD106 and HLA-DR. In yet other embodiments, the stromal step cells are positive for CD105, CD106, CD54, CD166, CD90, CD29, CD71, Pax6 and negative for SSEA-1, Tra1-81, Tra1-61, CD31, CD45, CD11a, CD11c, CD14, CD138, Flk1, Flt1, and VE-cadherin. In certain embodiments, at least 65%, 70%, 75%, 80%. 85%, 86%. 88%. 89%, 90%, 91% 92%, 93%, 94%, 95%, 96%, 97%, 98% or 99% of cells in the plurality of stem cells are positive for CD105, CD106, CD54, CD166, CD90, CD29, CD71, Pax6 and negative for SSEA-1, Tra1-81, Tra1-61, CD31, CD45, CD11a, CD11c, CD14, CD138, Flk1, Flt1, and VE-cadherin.

In certain embodiments, the cells used with the subject methods are endothelial stem cells isolated from the subject's cornea. Methods of isolating such stem cells are described, for instance, in Engelmann et al., *Invest Ophthalmol Vis Sci* 29: 1656-1662 (1988), which is incorporated by reference in their entirety for all purposes, and particularly for all teachings relating to the isolating and culturing of corneal endothelial stem cells.

After isolation, the plurality of stem cells (e.g., LESCs) can be cultured using any suitable method to produce a stable cell line. The stem cells may be cultured before and/or after the manipulation of a nucleic acid mutation described herein. For instance, cultures can be maintained in the presence or absence of fibroblast cells (e.g., 3T3) as feeder cells. In other instances, human amniotic epithelial cells or human embryonic fibroblasts are used as feeder layers for cultures. Suitable techniques for the culturing of LESCs are further described in Takacs et al. *Cytometry A* 75: 54-66 (2009), Shortt et al., *Surv Opthalmol Vis Sci* 52: 483-502 (2007); and Cauchi et al. *Am J Ophthalmol* 146: 251-259 (2008), which are incorporated by reference in their entirety for all purposes, and particularly for all teachings relating to the culturing of LESCs.

IV. Nucleic Acid Manipulation Reagents

In one aspect, a nucleic acid mutation in a stem cell is manipulated to correct the nucleic acid mutation in a corneal dystrophy target nucleic acid. As used herein, a "corneal dystrophy target nucleic acid" refers to a nucleic acid that includes a mutation associated with one or more of the corneal dystrophies.

In some embodiments, the corneal dystrophy target nucleic acid is located in TGFBI, KRT3, KRT12, GSN, and UBIAD1 gene. In some embodiments, the corneal dystrophy target nucleic acid is associated with a SNP site resulting in encoding a mutant amino acid in a mutant protein as shown herein. In further embodiments, a mutant sequence comprising the SNP site encodes a mutant protein selected from the group consisting of (i) mutant TGFBI proteins comprising a mutation corresponding to Leu509Arg, Arg666Ser, Gly623Asp, Arg555Gln, Arg124Cys, Val505Asp, Ile522Asn, Leu569Arg, His572Arg, Arg496Trp, Pro501Thr, Arg514Pro, Phe515Leu, Leu518Pro, Leu518Arg, Leu527Arg, Thr538Pro, Thr538Arg, Val539Asp, Phe540del, Phe540Ser, Asn544Ser, Ala546Thr, Ala546Asp, Phe547Ser, Pro551Gln, Leu558Pro, His572del, Gly594Val, Val613del, Val613Gly, Met619Lys, Ala620Asp, Asn622His, Asn622Lys, Asn622Lys, Gly623Arg, Gly623Asp, Val624 Val625del, Val624Met, Val625Asp, His626Arg, His626Pro, Val627SerfsX44, Thr629_Asn630insAsnValPro, Val631Asp, Arg666Ser, Arg555Trp, Arg124Ser, Asp123delins, Arg124His, Arg124Leu, Leu509Pro, Leu103Ser104del, Val113Ile, Asp123His, Arg124Leu, and/or Thr125_Glu126del in TGFBI, for example, of Protein Accession No. Q15582; (ii) mutant KRT3 proteins comprising a mutation corresponding to Glu498Val, Arg503Pro, and/or Glu509Lys in Keratin 3 protein, for example, of Protein Accession No. P12035 or NP 476429.2; (iii) mutant KRT12 proteins with Met129Thr, Met129Val, Gln130Pro, Leu132Pro, Leu132Va, Leu132His, Asn133Lys, Arg135Gly, Arg135Ile, Arg135Thr, Arg135Ser, Ala137Pro, Leu140Arg, Val143Leu, Val143Leu, Lle391Leu399dup, Ile 426Val, Ile 426Ser, Tyr429Asp, Tyr429Cys, Arg430Pro, and/or Leu433Arg in KRT12, for example, of Protein Accession No. Q99456.1 or NP 000214.1; (iv) mutant GSN proteins with Asp214Tyr in GSN, for example, of Protein Accession No. P06396; and (v) mutant UBIAD1 proteins comprising a mutation corresponding to Ala97Thr, Gly98Ser, Asn102Ser, Asp112Asn, Asp112Gly, Asp118Gly, Arg119Gly, Leu121Val, Leu121Phe, Val122Glu, Val122Gly, Ser171Pro, Tyr174Cys, Thr175Ile, Gly177Arg, Lys181Arg, Gly186Arg, Leu188His, Asn232Ser, Asn233His, Asp236Glu, and/or Asp240Asn in UBIAD1, for example, of Protein Accession No. Q9Y5Z9.

Figure 2:
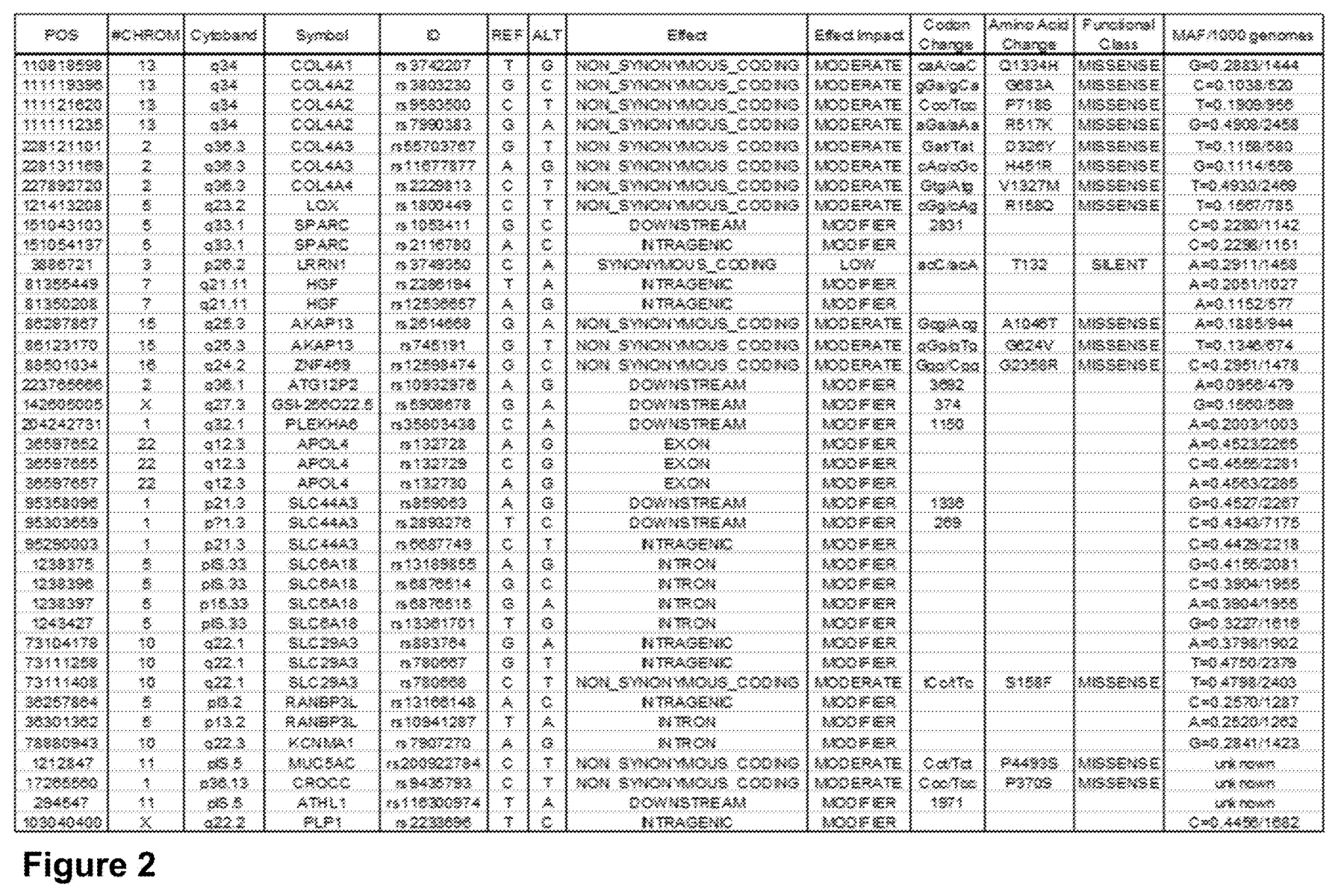

In certain embodiments, the corneal dystrophy target nucleic acid is associated with granular corneal dystrophy type II (e.g., TGFβI). In other embodiments, the corneal dystrophy target nucleic acid is associated with keratoconus. Without being bound by any particular theory of operation, it is believed that the mutations depicted in FIG. 2 are associated with keratoconus. In certain embodiments, the corneal dystrophy target nucleic acid includes one or more of the mutations depicted in FIG. 2.

Stem cells to be manipulated include individual isolated stem cells or stem cells from a stem cell line established from the isolated stem cells. Any suitable genetic manipulation method may be used to correct the nucleic acid mutation in the stem cells.

In certain embodiments, nucleic acid manipulation reagents are introduced into the stem cells. Such nucleic acid manipulation reagents subsequently correct the nucleic acid mutation in the stem cell to form manipulated stem cells. Nucleic acid manipulation reagents include, but are not limited to Zing-finger nucleases (ZFNs), transcription activator-like effector nucleases (TALENs) and Clustered Regularly Interspaced Short Palindromic Repeats (CRISPR) system reagents. See, e.g., Gaj et al., *Trends Biotechnol* 31(7): 397-405 (2013), which is incorporated by reference in its entirety for all purposes, and particularly for all teaching relating to nucleic acid manipulation reagents. Such reagents work by enabling efficient and precise modification of a target nucleic acid by inducing target DNA double-strand breaks (DSBs) that stimulate the cellular DNA repair mechanism, including error-prone non-homologous end joining (NHEJ) and/or homology directed repair (HDR) pathways. In the presence of a homology repair nucleic acid that contains a wild type allele of the nucleic acid mutation (e.g., a wild-type TGFBI or fragment thereof), the nicked target nucleic acid undergoes homologous recombination, thereby replacing the mutant allele with the wild type allele and correcting the nucleic acid mutation in the manipulated stem cell.

In some instances, the target nucleic acid manipulation reagents used with the subject methods provided herein include CRISPR system reagents. CRISPR system reagents used with the subject methods include, for example, a nucleic acid encoding a Type II nuclease (e.g., Cas9 nuclease or a Cpfl nuclease), a nucleic acid encoding a guide RNA (gRNA) and a repair nucleic acid that includes a wild type allele of the gene of interest or fragment thereof. The guide RNA includes a CRISPR RNA (crRNA) in combination with a trans-activating CRISPR RNA (tracrRNA). In some embodiments that utilize CRISPR system reagents, the crRNA and tracrRNA are included as separate reagents in lieu of a guide RNA.

In some embodiments, the repair nucleic acid is capable of undergoing homologous recombination by the HDR pathway at a region of a stem cell genome that includes a mutation associated with a corneal dystrophy as described herein (i.e., a "corneal dystrophy target nucleic acid"). In certain embodiments, the repair nucleic acid is able to homologously recombine with a target nucleic acid within the TGFBI, KRT3, KRT12, GSN, and UBIAD1 gene. In particular embodiments, the repair nucleotide molecule is able to homologously recombine with a nucleic acid in the TGFBI gene encoding a mutant amino acid described herein (e.g. Leu132Pro). In some embodiments, the at least one vector includes multiple repair nucleic acids. The repair nucleic acid may further include a label for identification and sorting of cells described herein containing the specific mutation. Exemplary labels that can be included with the repair nucleotide molecule include fluorescent labels and nucleic acid barcodes that are identifiable by length or sequence.

Nucleic acids encoding the Type II nuclease and guide RNA may each be operably linked to a regulatory element and may be included on a single vector or on different vectors. In some embodiments, the guide RNA and the Type II nuclease are included on the same vector. In some embodiments, the guide RNA and Type II nuclease are included on different vectors.

In some exemplary embodiments, the vectors that include the nucleic acids encoding the guide RNA and/or Type-II nuclease are capable of stable integration into the cellular genome of one or more cells of the plurality of stem cells. In some examples, the Type-II nuclease and guide RNA do not occur in nature together. Exemplary CRISPR system reagents and methods of use in the present invention are described in further detail, for example, in Shalem et al., *Nature Reviews Genetics* 16: 299-311 (2013); Zhang et al., Human Molecular Genetics 23(R1): R40-6 (2014); Zetsche et al. dx.doi.org/10.1016/j.ce11.2015.09.038 (2015) and Zhu et al. *Cell* 157: 1262-1278 (2014), which are herein incorporated by reference in their entirety for all purposes, and particularly for all teachings relating to CRISPR system reagents.

In the CRISPR system, a gRNA/Type II nuclease complex is recruited to a genomic target sequence by the base-pairing between the gRNA sequence and the complement to the target nucleic acid. The binding of the gRNA/Type II nuclease complex localizes the Type II nuclease to the genomic target sequence so that the Type II nuclease can cut both strands of DNA causing a Double Strand Break (DSB).

Repair of the DSB can occur through either (1) the Non-Homologous End Joining (NHEJ) DNA repair pathway or (2) the Homology Directed Repair (HDR) pathway. The NHEJ repair pathway often results in inserts/deletions (In-Dels) at the DSB site that can lead to frameshifts and/or premature stop codons, effectively disrupting the open reading frame (ORF) of the target nucleic acid, thereby decreasing the expression of the gene product encoded by the target nucleic acid. The HDR pathway requires the presence of a repair nucleic acid, which is used to fix the DSB. Specific nucleotide changes (e.g., a wild type allele) can be introduced into a targeted mutant gene by the use of HDR with a repair nucleic acid. The HDR pathway can be used, for example, to correct a mutation in a stem cell, where the mutation is linked to a corneal disorder described herein (e.g., TGFBI gene).

In some embodiments, the nucleic acid manipulation reagents include a repair nucleic acid. The repair nucleic acid introduces a specific allele (e.g., a wild-type allele) into the genome of one or more cells of the plurality of stem cells upon repair of a Type II nuclease induced DSB through the HDR pathway. In some embodiments, the repair nucleic acid is a single stranded DNA (ssDNA). In other embodiments, the repair nucleic acid is introduced into the cell as a plasmid vector. In some embodiments, the repair nucleic acid is 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 105, 105 to 110, 110 to 115, 115 to 120, 120 to 125, 125 to 130, 130 to 135, 135 to 140, 140 to 145, 145 to 150, 150 to 155, 155 to 160, 160 to 165, 165 to 170, 170 to 175, 175 to 180, 180 to 185, 185 to 190, 190 to 195, or 195 to 200 nucleotides in length. In some embodiments, the repair nucleic acid is 200 to 300, 300, to 400, 400 to 500, 500 to 600, 600 to 700, 700 to 800, 800 to 900, 900 to 1,000 nucleotides in length. In other embodiments, the repair nucleic acid is 1,000 to 2,000, 2,000 to 3,000, 3,000 to 4,000, 4,000 to 5,000, 5,000 to 6,000, 6,000 to 7,000, 7,000 to 8,000, 8,000 to 9,000, or 9,000 to 10,000 nucleotides in length. In some embodiments, the repair nucleic acid is capable of undergoing homologous recombination by the HDR pathway at a region of a stem cell genome that includes a mutation associated with a corneal dystrophy as described herein (i.e., a "corneal dystrophy target nucleic acid"). In certain embodiments, the repair nucleic acid is able to homologously recombine with a target nucleic acid within the TGFBI gene. In particular embodiments, the repair nucleic acid is able to homologously recombine with a nucleic acid in the TGFBI gene that encodes for arginine 124, arginine 555, or histidine 626 in a TGFβI polypeptide. In certain embodiments, the repair nucleic acid is able to homologously recombine with a nucleic acid in the TGFBI gene that encodes for an amino acid substitution selection from R124C, R124H, R124L, R555W, R555Q, and H626P. In some embodiments, the repair nucleic acid comprises a nucleic acid encoding for arginine 124 of a TGFβI polypeptide. For example, the repair nucleic acid is used to insert cytosine at nucleotide 417 of a TGFβI gene (e.g., to correct a C to T transition at nucleotide 417 of TGFβI gene), guanine at nucleotide 418 of a TGFβI gene (e.g., to correct a G to A or G to T transition at nucleotide 418 of TGFβI gene). In certain embodiments, the repair nucleic acid comprises a nucleic acid encoding for arginine 555 of a TGFβI polypeptide. For example, the repair nucleic acid is used to insert cytosine at nucleotide 1663 of TGFβI gene (e.g., to correct a C to T transition at nucleotide 1663 of TGFβI gene) and to insert guanine at nucleotide 1664 of a TGFβI gene (e.g., to correct a G to A transition at nucleotide 1663 of TGFβI gene). In certain embodiments, the repair nucleic acid comprises a nucleic acid encoding for histidine 626 of a TGFβI polypeptide. For example, the repair nucleic acid is used to insert adenine to nucleotide 1924 of a TGFβI gene (e.g., to correct an A to C transition at nucleotide 1924 of TGFβI gene). In yet other embodiments, the repair nucleic acid comprises a nucleic acid encoding for arginine 124, arginine 555, and histidine 626 of a TGFβI polypeptide.

In other embodiments, the repair nucleic acid is able to homologously recombine with a corneal dystrophy target nucleic acid is associated with keratoconus (e.g., a target nucleic acid that includes one or more of the mutations depicted in FIG. 2). In some embodiments, the corneal dystrophy target nucleic acid includes a mutation in COL4A1-4, LOX, SPARC, LRRN1, HGF, AKAP13, ZNF469, ATG12P2, GS1-256O22.5, PLEKHA6, APOL4, SLC44A3, SLC6A18, SLC29A3, RANBP3L, KCNMA1, MUC5AC, CROCC, ATHL1, or PLP1. In some embodiments, the corneal dystrophy target nucleic acid includes a mutation that corresponds to reference SNP cluster identifier rs3742207 (e.g., SNP identified by rs3742207 in the National Center for Biotechnology Information's dbSNP database). In some embodiments, the corneal dystrophy target nucleic acid includes a mutation that corresponds to reference SNP cluster identifier rs3803230. In some embodiments, the corneal dystrophy target nucleic acid includes a mutation that corresponds to reference SNP cluster identifier rs9583500. In some embodiments, the corneal dystrophy target nucleic acid includes a mutation that corresponds to reference SNP cluster identifier rs7990383. In some embodiments, the corneal dystrophy target nucleic acid includes a mutation that corresponds to reference SNP cluster identifier rs55703767. In some embodiments, the corneal dystrophy target nucleic acid includes a mutation that corresponds to reference SNP cluster identifier rs11677877. In some embodiments, the corneal dystrophy target nucleic acid includes a mutation that corresponds to reference SNP cluster identifier rs2229813. In some embodiments, the corneal dystrophy target nucleic acid includes a mutation that corresponds to reference SNP cluster identifier rs1800449. In some embodiments, the corneal dystrophy target nucleic acid includes a mutation that corresponds to reference SNP cluster identifier rs1053411. In some embodiments, the corneal dystrophy target nucleic acid includes a mutation that corresponds to reference SNP cluster identifier rs2116780. In some embodiments, the corneal dystrophy target nucleic acid includes a mutation that corresponds to reference SNP cluster identifier rs3749350. In some embodiments, the corneal dystrophy target nucleic acid includes a mutation that corresponds to reference SNP cluster identifier rs2286194. In some embodiments, the corneal dystrophy target nucleic acid includes a mutation that corresponds to reference SNP cluster identifier rs12536657. In some embodiments, the corneal dystrophy target nucleic acid includes a mutation that corresponds to reference SNP cluster identifier rs2614668. In some embodiments, the corneal dystrophy target nucleic acid includes a mutation that corresponds to reference SNP cluster identifier rs745191. In some embodiments, the corneal dystrophy target nucleic acid includes a mutation that corresponds to reference SNP cluster identifier rs12598474. In some embodiments, the corneal dystrophy target nucleic acid includes a mutation that corresponds to reference SNP cluster identifier rs10932976. In some embodiments, the corneal dystrophy target nucleic acid includes a mutation that corresponds to reference SNP cluster identifier rs5908678. In some embodiments, the corneal dystrophy target nucleic acid includes a mutation that corresponds to reference SNP cluster identifier rs35803438. In some embodiments, the corneal dystrophy target nucleic acid includes a mutation that corresponds to reference SNP cluster identifier rs132728. In some embodiments, the corneal dystrophy target nucleic acid includes a mutation that corresponds to reference SNP cluster identifier rs132729. In some embodiments, the corneal dystrophy target nucleic acid includes a mutation that corresponds to reference SNP cluster identifier rs132730 In some embodiments, the corneal dystrophy target nucleic acid includes a mutation that corresponds to reference SNP cluster identifier rs859063. In some embodiments, the corneal dystrophy target nucleic acid includes a mutation that corresponds to reference SNP cluster identifier rs2893276. In some embodiments, the corneal dystrophy target nucleic acid includes a mutation that corresponds to reference SNP cluster identifier rs6687749. In some embodiments, the corneal dystrophy target nucleic acid includes a mutation that corresponds to reference SNP cluster identifier rs13189855. In some embodiments, the corneal dystrophy target nucleic acid includes a mutation that corresponds to reference SNP cluster identifier rs6876514. In some embodiments, the corneal dystrophy target nucleic acid includes a mutation that corresponds to reference SNP cluster identifier rs6876515. In some embodiments, the corneal dystrophy target nucleic acid includes a mutation that corresponds to reference SNP cluster identifier rs13361701. In some embodiments, the corneal dystrophy target nucleic acid includes a mutation that corresponds to reference SNP cluster identifier rs883764. In some embodiments, the corneal dystrophy target nucleic acid includes a mutation that corresponds to reference SNP cluster identifier rs780667. In some embodiments, the corneal dystrophy target nucleic acid includes a mutation that corresponds to reference SNP cluster identifier rs780668. In some embodiments, the corneal dystrophy target nucleic acid includes a mutation that corresponds to reference SNP cluster identifier rs13166148. In some embodiments, the corneal dystrophy target nucleic acid includes a mutation that corresponds to reference SNP cluster identifier rs10941287. In some embodiments, the corneal dystrophy target nucleic acid includes a mutation that corresponds to reference SNP cluster identifier rs7907270. In some embodiments, the corneal dystrophy target nucleic acid includes a mutation that corresponds to reference SNP cluster identifier rs200922784. In some embodiments, the corneal dystrophy target nucleic acid includes a mutation that corresponds to reference SNP cluster identifier rs9435793. In some embodiments, the corneal dystrophy target nucleic acid includes a mutation that corresponds to reference SNP cluster identifier rs116300974. In some embodiments, the corneal dystrophy target nucleic acid includes a mutation that corresponds to reference SNP cluster identifier rs2233696.

In some embodiments, the nucleic acid manipulation reagents include multiple repair nucleic acids. In certain embodiments, the repair nucleic acids comprise a nucleic acid encoding for arginine 124 of a TGFβI polypeptide and a nucleic acid encoding for arginine 555 of the TGFβI polypeptide. In some embodiments, the repair nucleic acids further comprise a nucleic acid encoding for histidine 626 of a TGFβI polypeptide. In some embodiments, the CRISPR system reagents used with the subject methods include a first nucleic acid encoding a first guide RNA for the nucleic acid encoding for arginine 124 of a TGFβI polypeptide and a second nucleic acid encoding a second guide RNA for the nucleic acid encoding for arginine 555 of a TGFβI polypeptide. In some embodiments, the CRISPR system reagents further include a third nucleic acid encoding a third guide RNA for the nucleic acid encoding for histidine 626. In some embodiments, the CRISPR system reagents further include any combination of the first nucleic acid, the second nucleic acid, and the third nucleic acid (e.g., a combination of the first nucleic acid and the third nucleic acid, or a combination of the second nucleic acid and the third nucleic acid). In some embodiments, the repair nucleic acid is capable of repairing a corneal dystrophy target nucleic acid that encodes for one or more amino acid substitutions that includes Q1334H in COL4A1, G683A in COL4A2, P718S in COL4A2, R517K in COL4A2, D326Y in COL4A3, H451R in COL4A3, V1327M in COL4A4, R158Q in LOX, A1046T in AKAP13, G624V in AKAP13, G2358R in ZNF469, S158F in SLC29A3, P4493S in MUC5AC, P370S in CROCC or combinations thereof.

The repair nucleic acid may further include a label for identification and sorting of stem cells containing the specific mutation. Exemplary labels that can be included with the repair nucleic acid include fluorescent labels and nucleic acid barcodes that are identifiable by length or sequence.

In further embodiments, the nucleic acid manipulation reagents also include one or more reagents that promote the HDR pathway over HNEJ repair of DSBs. Such reagents advantageously allow for the homologous recombination of the repair nucleic acid by the HDR pathway. Reagents that promote the HDR pathway over HNEJ repair of DSBs include, but are not limited to, agents that repress genes involved in HNEJ repair, for example, DNA ligase IV. See, e.g., Maruyana et al. *Nat Biotechnol.* 33(5): 538-42 (2015), which is herein incorporated by reference in its entirety for all purposes, and particularly for all teachings relating to agents that repress genes involved in HNEJ repair of DSBs.

The Type II nuclease used with the subject methods provided herein may be an inducible Type II nuclease that is optimized for expression in a temporal or cell-type dependent manner. Inducible promoters that can be linked to the Type II nuclease include, but are not limited to tetracycline-inducible promoters, metallothionein promoters; tetracycline-inducible promoters, methionine-inducible promoters (e.g., MET25, MET3 promoters); and galactose-inducible promoters (GAL1, GAL7 and GAL10 promoters). Other suitable promoters include the ADH1 and ADH2 alcohol dehydrogenase promoters (repressed in glucose, induced when glucose is exhausted and ethanol is made), the CUP1 metallothionein promoter (induced in the presence of $Cu^{2+}$, $Zn^{2+}$), the PHO5 promoter, the CYC1 promoter, the HIS3 promoter, the PGK promoter, the GAPDH promoter, the ADC1 promoter, the TRP1 promoter, the URA3 promoter, the LEU2 promoter, the ENO promoter, the TP1 promoter, and the AOX1 promoter.

Mutant Type II nucleases that exhibit improved specificity may also be used (see, e.g., Ann Ran et al. *Cell* 154(6) 1380-89 (2013), which is herein incorporated by reference in its entirety for all purposes, and particularly for all teachings relating to mutant Cas9 nucleases with improved specificity for target nucleic acids). The nucleic acid manipulation reagents can also include a deactivated Type II nuclease (e.g., dCas9). Deactivated Cas9 binding to nucleic acid elements alone may repress transcription by sterically hindering RNA polymerase machinery. Further, deactivated Cas may be used as a homing device for other proteins (e.g., transcriptional repressor, activators and recruitment domains) that affect gene expression at the target site without introducing irreversible mutations to the target nucleic acid. For example, dCas9 can be fused to transcription repressor domains such as KRAB or SID effectors to promote epigenetic silencing at a target site. Cas9 can also be converted into a synthetic transcriptional activator by fusion to VP16/VP64 or p64 activation domains.

Nucleic acid manipulation reagents can be introduced into stem cells using any suitable method. Exemplary methods for introducing the nucleic acid manipulation reagents include, but are not limited to, transfection, electroporation and viral-based methods.

In some cases, the one or more cell uptake reagents are transfection reagents. Transfection reagents include, for example, polymer based (e.g., DEAE dextran) transfection reagents and cationic liposome-mediated transfection reagents. Electroporation methods may also be used to facilitate uptake of the nucleic acid manipulation reagents. By applying an external field, an altered transmembrane potential in a cell is induced, and when the transmembrane potential net value (the sum of the applied and the resting potential difference) is larger than a threshold, transient permeation structures are generated in the membrane and electroporation is achieved. See, e.g., Gehl et al., *Acta Physiol. Scand.* 177:437-447 (2003).

Nucleic acid manipulation reagents may also be delivered through viral transduction into the stem cells. Suitable viral delivery systems include, but are not limited to, adeno-associated virus (AAV) retroviral and lentivirus delivery systems. Such viral delivery systems are particularly useful in instances where the stem cell is resistant to transfection. Methods that use a viral-mediated delivery system may further include a step of preparing viral vectors encoding the nucleic acid manipulation reagents and packaging of the vectors into viral particles. Other method of delivery of nucleic acid reagents include, but are not limited to, lipofection, nucleofection, microinjection, biolistics, virosomes, liposomes, immunoliposomes, polycation or lipid:nucleic acid conjugates, naked DNA, artificial virions, and agent-enhanced uptake of nucleic acids. See, also Neiwoehner et al., *Nucleic Acids Res.* 42:1341-1353 (2014), which is herein incorporated by reference in its entirety for all purposes, and particularly for all teachings relating to reagent delivery systems.

In one aspect, the nucleic acid mutation in a corneal dystrophy target nucleic acid in a stem cell is manipulated by introducing an engineered Clustered Regularly Interspaced Short Palindromic Repeats (CRISPR)/CRISPR associated protein 9 (Cas9) system into the stem cell, wherein the CRISPR/Cas9 system comprises at least one vector comprising a nucleotide molecule encoding Cas9 nuclease and an single guide RNA (sgRNA), and the Cas9 nuclease and said sgRNA do not naturally occur together.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. In some embodiments, the Cas9 nuclease and the sgRNA do not naturally occur together.

The engineered CRISPR/Cas9 system can be introduced into cells using any suitable method known in the art and those described herein. In some embodiments, the introducing may comprise administering the engineered CRISPR/Cas9 system described herein to stem cells in culture, or in a host organism. As discussed above, exemplary methods for introducing the engineered CRISPR/Cas9 system include, but are not limited to, transfection, electroporation and viral-based methods. In some cases, the one or more cell uptake reagents are transfection reagents. Transfection reagents include, for example, polymer based (e.g., DEAE dextran) transfection reagents and cationic liposome-mediated transfection reagents. Electroporation methods may also be used to facilitate uptake of the nucleic acid manipulation reagents. By applying an external field, an altered transmembrane potential in a cell is induced, and when the transmembrane potential net value (the sum of the applied and the resting potential difference) is larger than a threshold, transient permeation structures are generated in the membrane and electroporation is achieved. See, e.g., Gehl et al., *Acta Physiol. Scand.* 177:437-447 (2003). The engineered CRISPR/Cas9 system also be delivered through viral transduction into the cells. Suitable viral delivery systems include, but are not limited to, adeno-associated virus (AAV), retroviral and lentivirus delivery systems. Such viral delivery systems are useful in instances where the cell is resistant to transfection. Methods that use a viral-mediated delivery system may further include a step of preparing viral vectors encoding the nucleic acid manipulation reagents and packaging of the vectors into viral particles. Other method of delivery of nucleic acid reagents include, but are not limited to, lipofection, nucleofection, microinjection, biolistics, virosomes, liposomes, immunoliposomes, polycation or lipid:nucleic acid conjugates, naked DNA, artificial virions, and agent-enhanced uptake of nucleic acids. See, also Neiwoehner et al., *Nucleic Acids Res.* 42:1341-1353 (2014), and U.S. Pat. Nos. 5,049,386, 4,946,787; and 4,897,355, which are herein incorporated by reference in its entirety for all purposes, and particularly for all teachings relating to reagent delivery systems. In some embodiments, the introduction is performed by non-viral vector delivery systems include DNA plasmids, RNA (e.g. a transcript of a vector described herein), naked nucleic acid, and nucleic acid complexed with a delivery vehicle, such as a liposome. Delivery can be to cells (e.g. in vitro or ex vivo administration) or target tissues (e.g. in vivo administration).

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as "crRNA" herein, or a "spacer" in the context of an endogenous CRISPR system), and/or other sequences and transcripts from a CRISPR locus. As described above, sgRNA is a combination of at least tracrRNA and crRNA. In some embodiments, one or more elements of a CRISPR system is derived from a type II CRISPR system. In some embodiments, one or more elements of a CRISPR system is derived from a particular organism comprising an endogenous CRISPR system, such as *Streptococcus pyogenes* or *Staphylococcus aureus*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. In disclosure, "target site" refers to a site of the target sequence including both the target sequence and its complementary sequence, for example, in double stranded nucleotides. In some embodiments, the target site described herein may mean a first target sequence hybridizing to sgRNA or crRNA of CRISPR/Cas9 system, and/or a second target sequence adjacent to the 5'-end of a PAM. A target sequence may comprise any polynucleotide, such as DNA or RNA polynucleotides. In some embodiments, a target sequence is located in the nucleus or cytoplasm of a cell. In some embodiments, the target sequence is located within an organelle of a eukaryotic cell, for example, mitochondrion or chloroplast.

The sgRNA may be artificial, man-made, synthetic, and/or non-naturally occurring. In some embodiments, the sgRNA comprises (i) CRISPR targeting RNA (crRNA) sequence and (ii) a trans-activating crRNA (tracrRNA)

sequence, which also may be called "sgRNA scaffold." In some embodiments, the crRNA sequence and tracrRNA sequence do not naturally occur together. As used herein, the term "sgRNA" may refer to a single guide RNA containing (i) a guide sequence (crRNA sequence) and (ii) a Cas9 nuclease-recruiting sequence (tracrRNA). The crRNA sequence may be a sequence that is homologous to a region in your gene of interest and may direct Cas9 nuclease activity. The crRNA sequence and tracrRNA sequence do not naturally occur together. The sgRNA may be delivered as RNA or by transforming with a plasmid with the sgRNA-coding sequence (sgRNA gene) under a promoter.

In some embodiments, the sgRNA or the crRNA hybridizes to at least a part of a target sequence (e.g. target genome sequence), and the crRNA may have a complementary sequence to the target sequence. "Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%. 85%, 90%, 95%. 97%, 98%. 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence, Non-limiting examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self 17 hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "about" may refer to a range of values that are similar to the stated reference value. In certain embodiments, the term "about" refers to a range of values that fall within 15, 10, 9, 8, 7, 6, 5, 4, 3, 2, 1 percent or less of the stated reference value. In additional embodiments, the crRNA or the guide sequence is about 17, 18, 19, 20, 21, or 22 nucleotide long. In further embodiments, the crRNA includes the nucleotide sequences of TAG-GAAGCTAATCTATCATT (SEQ ID NO: 9). In additional embodiments, the crRNA excludes crRNA sequences having the nucleotide sequences of SEQ ID NO: 9. In yet further embodiments; the crRNA excludes crRNA sequences hybridizing to a nucleotide sequence comprising a SNP resulting in L132P mutation in kratin 12 protein. In yet further embodiments; the crRNA excludes crRNA sequences hybridizing to a nucleotide sequence comprising a SNP resulting in a mutation in keratin 12 protein.

In some embodiments, tracrRNA provides a hairpin structure that activates Cas9 for opening up the dsDNA for binding of the crRNA sequence. The tracrRNA may have a sequence complementary to the palindromic repeat. When the tracrRNA hybridizes to the short palindromic repeat, it may trigger processing by the bacterial double-stranded RNA-specific ribonuclease, RNase III. In additional embodiments, the tracrRNA may have SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in E. coli (Ishino et al., J. Bacteriol., 169:5429-5433 [1987]; and Nakata et al., J. Bacteriol., 171:3553-3556 [1989]), and associated genes. Similar interspersed SSRs have been identified in Haloferax mediterranei, Streptococcus pyogenes, Anabaena, and Mycobacterium tuberculosis (See, Groenen et al., Mol. Microbiol., 10:1057-1065 [1993]; Hoe et al., Emerg. Infect. Dis., 5:254 263 [1999]; Masepohl et al., Biochim. Biophys. Acta 1307:26-30 [1996]; and Mojica et al., Mol. Microbiol., 17:85-93 [1995]). The CRISPR loci may differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In certain embodiments, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). The tracrRNA sequence may be any sequence for tracrRNA for CRISPR/Cas9 system known in the art. In additional embodiments, the tracrRNA comprises a nucleotide sequence having at least about 70, 75, 80, 85, 90, 95 or 100% sequence identity with the nucleotide sequence of SEQ ID NO: 2 and 6. Exemplary CRISPR/Cas9 systems, sgRNA, crRNA and tracrRNA, and their manufacturing process and use are disclosed in U.S. Pat. No. 8,697,359, U.S. Patent Application Publication Nos. 20150232882, 20150203872, 20150184139, 20150079681, 20150073041, 20150056705, 20150031134, 20150020223, 20140357530, 20140335620, 20140310830, 20140273234, 20140273232, 20140273231, 20140256046, 20140248702, 20140242700, 20140242699, 20140242664, 20140234972, 20140227787, 20140189896, 20140186958, 20140186919, 20140186843, 20140179770, 20140179006, 20140170753, 20140093913, 20140080216, and WO2016049024, all of which are incorporated herein by its entirety.

In some embodiments, the Cas9 nucleases described herein are known; for example, the amino acid sequence of S. pyogenes Cas9 protein may be found in the SwissProt database under accession number Q99ZW2. The Cas9 nuclease may be a Cas9 homolog or ortholog. Mutant Cas9 nucleases that exhibit improved specificity may also be used (see, e.g., Ann Ran et al. *Cell* 154(6) 1380-89 (2013), which is herein incorporated by reference in its entirety for all purposes. and particularly for all teachings relating to mutant Cas9 nucleases with improved specificity for target nucleic acids). The nucleic acid manipulation reagents can also include a deactivated Cas9 nucleases (dCas9). Deactivated Cas9 binding to nucleic acid elements alone may repress transcription by sterically hindering RNA polymerase machinery. Further, deactivated Cas may be used as a homing device for other proteins (e.g., transcriptional repressor, activators and recruitment domains) that affect gene expression at the target site without introducing irreversible mutations to the target nucleic acid. For example, dCas9 can be fused to transcription repressor domains such as KRAB or SID effectors to promote epigenetic silencing at a target site. Cas9 can also be converted into a synthetic transcriptional activator by fusion to VP16/VP64 or p64 activation domains.

In some embodiments, the Cas9 nucleases direct cleavage of one or both strands at the location of a target sequence, such as within the target sequence and/or within the complement of the target sequence. Following directed DNA cleavage by the Cas9 nuclease, there are two modes of DNA repair available to the cell: homology directed repair (HDR) and non-homologous end joining (NHEJ). While seamless correction of the mutation by HDR following Cas9 cleavage close to the mutation site is attractive, the efficiency of method means that it could only be used for in vitro/ex vivo modification of stem cells or induced pluripotent stem cells (iPSC) with an additional step to select those cells in which repair had taken place and purify those modified cells only. HDR does not occur at a high frequency in cells. NHEJ occurs at a much higher efficiency and is suitable for the dominant-negative mutations described for many of the corneal dystrophies. In additional embodiments, the Cas9 nuclease is from *Streptococcus*. In yet additional embodiments, the Cas9 nuclease is from *Streptococcus pyogenes, Streptococcus dysgalactiae, Streptococcus canis, Streptococcus equi, Streptococcus iniae, Streptococcus phocae, Streptococcus pseudoporcinus, Streptococcus oxalis, Streptococcus pseudoporcinus, Streptococcus infantarius, Streptococcus mutans, Streptococcus agalactiae, Streptococcus caballi, Streptococcus equinus, Streptococcus sp. oral taxon, Streptococcus mitis, Streptococcus gallolyticus, Streptococcus gordonii,* or *Streptococcus pasteurianus,* or variants thereof. Such variants may include D10A Nickase, Spy Cas9-HF1 as described in Kleinstiver et al, 2016 *Nature,* 529, 490-495. In additional embodiments, the Cas9 nuclease is from *Staphylococcus*. In yet additional embodiments, the Cas9 nuclease is from *Staphylococcus aureus, S. simiae, S. auricularis, S. carnosus, S. condimenti, S. massiliensis, S. piscifermentans, S. simulans, S. capitis, S. caprae, S. epidermidis, S. saccharolyticus, S. devriesei, S. haemolyticus, S. hominis, S. agnetis, S. chromogenes, S. fells, S. delphini, S. hyicus, S. intermedius, S. lutrae, S. micron, S. muscae, S. pseudintermedius, S. rostri, S. schleiferi, S. lugdunensis, S. arlettae, S. cohnii, S. equorum, S. gallinarum, S. kloosii, S. leei, S. nepalensis, S. saprophyticus, S. succinus, S. xylosus, S. fleurettii, S. lentus, S. sciuri, S. stepanovicii, S. vitulinus, S. simulans, S. pasteuri, S. warneri,* or variants thereof.

In additional embodiments, the Cas9 nuclease comprises an amino acid sequence having at least about 60, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity with an amino acid sequence selected from the group consisting of SEQ ID NO: 4 or 8. In yet further embodiments, the nucleotide molecule encoding Cas9 nuclease comprises a nucleotide sequence having at least about 60, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity with a nucleotide sequence selected from the group consisting of SEQ ID NO: 3 or 7.

In some embodiments, the CRISPR/Cas9 system and the methods using the CRISPR/Cas9 system described herein alter a DNA sequence by the NHEJ. In additional embodiments, the CRISPR/Cas9 system or the at least one vector described herein does not include a repair nucleotide molecule. In some embodiments, the methods described herein alter a DNA sequence by the HDR described herein. In additional embodiments, HDR approach could be used in an ex vivo approach to gene therapy in MECD. In further embodiments, approach may not be allele specific and may be used to repair mutations in KRT12 codons 129, 130, 132, 133 and 135.

In some embodiments, the engineered CRISPR/Cas9 system comprises (a) a first regulatory element operably linked to the sgRNA that hybridizes with the target sequence described herein, and (b) a second regulatory element operably linked to the nucleotide molecule encoding Cas9 nuclease, wherein components (a) and (b) are located on a same vector or different vectors of the system, the sgRNA targets (e.g., hybridizes with) the target sequence, and the Cas9 nuclease cleaves the DNA molecule. The target sequence may be a nucleotide sequence complementary to from 16 to 25 nucleotides adjacent to the 5' end of a PAM. Being "adjacent" herein means being within 2 or 3 nucleotides of the site of reference, including being "immediately adjacent," which means that there is no intervening nucleotides between the immediately adjacent nucleotide sequences and the immediate adjacent nucleotide sequences are within 1 nucleotide of each other. In additional embodiments, the cell is a eukaryotic cell, or a mammalian or human cell, and the regulatory elements are eukaryotic regulators. In further embodiments, the cell is a stem cell described herein. In some embodiments, the Cas9 nuclease is codon-optimized for expression in a eukaryotic cell.

In some embodiments, the first regulatory element is a polymerase III promoter. In some embodiments, the second regulatory element is a polymerase II promoter. The term "regulatory element" is intended to include promoters, enhancers, internal ribosomal entry sites (IRES), and other expression control elements (e.g. transcription termination signals such as polyadenylation signals and poly-U sequences). Such regulatory elements are described, for example, in Goeddel, GENE EXPRESSION TECHNOLOGY: METHODS IN ENZYMOLOGY 185, Academic Press, San Diego. Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g.

1, 2, 3, 4, 5, or more pol I promoters), or combinations thereof, Examples of pol III promoters include, but are not limited to, U6 and H1 promoters. Examples of poi II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such a WPRE; CMV enhancers; the R-U5' segment in LTR of HTLV-I (Mol. Cell Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31. 1981).

In some embodiments, the Cas9 nuclease provided herein is an inducible the Cas9 nuclease that is optimized for expression in a temporal or cell-type dependent manner. The first regulatory element may be an inducible promoter that can be linked to the Cas9 nuclease include, but are not limited to tetracycline-inducible promoters, metallothionein promoters; tetracycline-inducible promoters, methionine-inducible promoters (e.g., MET25, MET3 promoters); and galactose-inducible promoters (GAL1, GAL7 and GAL10 promoters). Other suitable promoters include the ADH1 and ADH2 alcohol dehydrogenase promoters (repressed in glucose, induced when glucose is exhausted and ethanol is made), the CUP1 metallothionein promoter (induced in the presence of $Cu^{2+}$, $Zn^{2+}$), the PHO5 promoter, the CYC1 promoter, the HIS3 promoter, the PGK promoter, the GAPDH promoter, the ADC1 promoter, the TRP1 promoter, the URA3 promoter, the LEU2 promoter, the ENO promoter, the TP1 promoter, and the AOX1 promoter.

It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

The term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids. Recombinant expression vectors can comprise a nucleic acid of the invention in a form suitable for expression of the nucleic acid in a host cell, which means that the recombinant expression vectors include one or more regulatory elements, which is, in some cases, selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). Advantageous vectors include lentiviruses and adeno-associated viruses, and types of such vectors can also be selected for targeting particular types of cells.

Stem cells that have undergone a nucleic acid manipulation event (i.e., a "manipulated" stem cell) can be isolated using any suitable method. In some embodiments, the repair nucleic acid further comprises a nucleic acid encoding a selectable marker. In these embodiments, successful homologous recombination of the repair nucleic into a host stem cell genome is also accompanied by integration of the selectable marker. Thus, in such embodiments, the positive marker is used to select for manipulated stem cells. In some embodiments, the selectable marker allows the manipulated stem cell to survive in the presence of a drug that otherwise would kill the cell. Such selectable markers include, but are not limited to, positive selectable markers that confer resistance to neomycin, puromycin or hygromycin B. In addition, a selectable marker can be a product that allows a manipulated stem cell to be identified visually among a population of stem cells, some of which do not contain the selectable marker. Examples of such selectable markers include, but are not limited to the green fluorescent protein (GFP), which can be visualized by its fluorescence; the luciferase gene, which, when exposed to its substrate luciferin, can be visualized by its luminescence; and β-galactosidase (β-gal), which, when contacted with its substrate, produces a characteristic color. Such selectable markers are well known in the art and the nucleic acid sequences encoding these markers are commercially available (see, e.g., Sambrook et al., Molecular Cloning: A Laboratory Manual (Cold Spring Harbor Laboratory Press 1989). Methods that employ selectable markers that can be visualized by fluorescence may further be sorted using Fluorescence Activated Cell Sorting (FACS) techniques.

In some embodiments, isolated manipulated stem cells are used to establish cell lines for transplantation. The isolated manipulated cells can be cultured using any suitable method to produce a stable cell line. For instance, cultures can be maintained in the presence or absence of fibroblast cells (e.g., 3T3) as feeder cells. In other instances, human amniotic epithelial cells or human embryonic fibroblasts are used as feeder layers for cultures. In some embodiments, the manipulated stem cells are cultured on a feeder layer of fibroblast (e.g., 3T3 cells) in supplemented hormonal epithelial medium (SHEM). In certain embodiments, medium suitable for culturing the subject manipulated stem cells include one or more of the following components: fetal bovine serum, patient's autologous serum, EGF, insulin, transferrin, sodium selenite, hydrocortisone, cholera toxin subunit A, DMSO, triiodothyronine, antibiotics (e.g., penicillin/streptomycin and gentamycin) and antimycotic (e.g., amphotericin B). Suitable techniques for the culturing of LESCs are further described in Takacs et al. *Cytometry A* 75: 54-66 (2009), Shortt et al., *Surv Opthalmol Vis Sci* 52: 483-502 (2007); and Cauchi et al. *Am J Ophthalmol* 146: 251-259 (2008), which are incorporated by reference in their entirety for all purposes, and particularly for all teachings relating to the culturing of LESCs. Verification of the desired nucleic manipulation in the established cell lines can be carried out using any suitable technique, including, for example, selection of a selectable marker as discussed herein and nucleic acid sequence to confirm the sequence of the desired nucleic acid manipulation.

V. Transplantation

In one aspect, following isolation of manipulated stem cells and optional establishment or culture of a cell line from the manipulated stem cells, the manipulated stem cells are transplanted into the subject in need of treatment thereof. The manipulated stem cells can be transplanted in the subject using any suitable method.

In some embodiments, a surgical graft for transplantation is developed from the manipulated cells that is subsequently transplanted into the subject. In certain embodiments, the manipulated stem cells are cultured on an amniotic membrane for a period of time sufficient for the manipulated stem cells to expand to an appropriate area sized for transplantation. Confirmation of growth can be done by various methods including direct observation, whole mount stained preparation, histopathology, immunohistochemistry, thymidine incorporation and by flow cytometry using markers for cell cycle. The cultured manipulated stem cells can then be transplanted directly with the amniotic membrane. In other embodiments, the manipulated stem cells are separated from the amniotic membrane and transplanted onto a non-amniotic membrane carrier to obtain a surgical graft. Suitable carriers include, but are not limited to paraffin gauze, contact lenses, collage shields, biopolymers, fibrin gels and anterior lens capsules.

Following transplantation, assessment of visual function in the subject can be carried out using any suitable test known in the art, including but not limited to assessments of uncorrected visual acuity (UCVA), best-corrected visual acuity (BCVA) and brightness acuity test (BAT). See, e.g., Awaad et al., *Am J Ophthalmol*. 145(4): 656-661 (2008) and Sharhan et al., *Br J Ophthalmol* 84:837-841 (2000), which are incorporated by reference in their entirety for all purposes, and particularly for all teachings relating to standards for assessing visual acuity. In certain embodiments, the subject's visual acuity improves by at least 5%, 10%, 15%, 20%, 25%, 30%, 35%, 40%, 45%, 50%, 55%, 60%, 65%, 70%, 75%, 80%, 85%, 90%, 95%, or 99% as compared prior to undergoing treatment.

In some embodiments, the method further includes repeating transplanting of the one or more manipulated stem cells into the subject at one or more predetermined frequencies (e.g., weekly, monthly, quarterly, biannually, annually, etc.).

VI. Kits

In another aspect, provided herein are kits that include nucleic acid manipulation reagents for the treatment of the corneal dystrophy. In some embodiments, the kit includes CRISPR reagents, for example, one or more guide RNAs that target the nucleic acid of interest, and a nuclease (e.g., Type-II nuclease). In additional embodiments, the kit also includes a repair nucleic acid that includes a wild-type allele of the mutation to be repaired as described herein. In some embodiments, the kit includes agents that facilitate uptake of the nucleic acid manipulation by cells, for example, a transfection agent or an electroporation buffer. In some embodiments, the subject kits provided herein include one or more reagents for the detection or isolation of stem cells, for example, labeled antibodies for one or more positive stem cell markers that can be used in conjunction with FACS.

EXAMPLES

The following examples are presented to illustrate various embodiments of the invention. It is understood that such examples do not represent and are not intended to represent exclusive embodiments; such examples serve merely to illustrate the practice of invention.

Mutation analysis: Mutations associated with various corneal dystrophies were analyzed to determine which were solely missense mutations or in-frame indels. analysis indicates that for the majority of K12 and TGFBI disease, nonsense or frameshifting indel mutations are not associated with disease. Furthermore, an analysis of the exome variant database confirmed that any naturally occurring nonsense, frameshifting indels or splice site mutations found in these genes are not reported to be associated with disease in these individuals.

Mutation analysis revealed that the following corneal-dystrophy genes are suitable for targeted nuclease gene therapy (Table 1).

TABLE 1

Genes and their associated corneal dystrophies that are suitable for a CRISPR/Cas9 mediated approach.

| Gene | Associated Corneal Dystrophies |
|---|---|
| TGFBI | Avellino corneal dystrophy |
|  | Reis-Bücklers corneal dystrophy |
|  | Thiel-Behnke corneal dystrophy |
|  | Grayson -Wilbrandt corneal dystrophy |
|  | Lattice Corneal Dystrophy I & II |
|  | Granular Corneal Dystrophy I, II & III |
|  | Epithelial Basement Membrane Dystrophy |
| KRT3 | Meesmann Epithelial Corneal Dystrophy |
| KRT12 | Meesmann Epithelial Corneal Dystrophy |
| UBIAD1 | Schnyder corneal dystrophy |

An investigation of the suitable corneal dystrophy genes was conducted for report to determine the number of mutations targetable by either a PAM-specific approach or a guide allele-specific approach. A PAM-specific approach requires the disease causing SNP to generate a novel PAM, whilst the allele specific approach involves the design of a guide containing the disease causing SNP.

All non-disease causing SNPs in TGFBI that generate a novel PAM with a minor allele frequency (MAF) of >10% were identified. The selection of SNPs with a MAF of >10% may provide a reasonable chance that the SNP resulting in a novel PAM will be found in cis with the disease causing mutation. All variants within TGFBI were analyzed to determine whether a novel PAM was created (Table 2). Previous reports demonstrate permanent inactivation of the mutant allele using approach (Shin et al., 2016. Human Molecular Genetics).

TABLE 2

The variants within TGFBI that result in a novel PAM that have a MAF of >10%.

| Exon Number | Position | SNP | Variant | Novel PAM (Required variant underlined) | MAF |
|---|---|---|---|---|---|
| 1 | | | | | |
| b/w 1 & 2 | Intronic variant, 1507 bp | rs756462 | T/C | cc<u>c</u> | 0.31 |
| 2 | | | | | |
| b/w 2 & 3 | Intronic variant | rs1989972 | A/C | atc<u>c</u>ca | 0.43 |
| | Intronic variant, 1945 bp | rs1989972 | A/C | cc<u>c</u> | 0.43 |
| | Intronic variant, 966 bp | rs3805700 | A/G | a<u>g</u>g | 0.41 |
| 3 | | | | | |
| b/w 3 & 4 | | | | | |
| 4 | | | | | |
| b/w 4 & 5 | | | | | |
| 5 | | | | | |
| b/w 5 & 6 | | | | | |
| 6 | Synonymous variant | rs1442 | G/C | <u>C</u>CT | 0.32 |
| b/w 6 & 7 | Intronic variant, 119 bp | rs764567 | A/G | <u>c</u>gg | 0.3 |
| | Intronic variant, 119 bp | rs764567 | A/G | gc<u>g</u>ggt | 0.3 |
| | Intronic variant, 268 bp | rs2073509 | T/G | g<u>g</u>g | 0.4 |
| | Intronic variant, 268 bp | rs2073509 | T/G | ca<u>g</u>ggt | 0.4 |
| | Intronic variant, 784 bp | rs2073511 | T/C | cc<u>t</u> | 0.4 |
| | Intronic variant, 685 bp | rs916951 | A(ancestral)/C/G | c<u>g</u>g | 0.37 |
| 7 | | | | | |
| b/w 7 & 8 | Intronic variant, 509 bp | rs1137550 | T/C | act<u>c</u>tg | 0.37 |
| 8 | Synonymous variant | rs1054124 | A/G | T<u>G</u>G | 0.39 |
| b/w 8 & 9 | Intronic variant, 207 bp | rs6889640 | C/A | <u>a</u>ctctc | 0.37 |
| 9 | | | | | |
| b/w 9 & 10 | | | | | |
| 10 | | | | | |
| b/w 10 & 11 | Intronic variant, 43 bp | rs6860369 | A/G | ga<u>g</u> | 0.4 |
| 11 | | | | | |
| b/w 11 & 12 | | | | | |
| 12 | | | | | |
| b/w 12 & 13 | Intronic variant, 713 bp | rs6871571 | A/G | tt<u>g</u>aat | 0.42 |
| 13 | | | | | |
| b/w 13 & 14 | Intronic variant, 530 bp | rs6893691 | A/G | c<u>g</u>g | 0.39 |
| | Intronic variant, 640 bp | rs1990199 | G/C | c<u>c</u>a | 0.39 |
| | Intronic variant, 659 bp | rs6894815 | G/C | <u>c</u>cc | 0.42 |
| | Intronic variant, 230 bp | rs10064478 | T/G | c<u>g</u>g | 0.42 |
| 14 | | | | | |
| b/w 14 & 15 | Intronic variant, 44 bp | rs6880837 | T/C | <u>c</u>ca | 0.41 |
| 15 | | | | | |
| b/w 15 & 16 | | | | | |
| 16 | | | | | |
| b/w 16 & 17 | | | | | |
| 17 | | | | | |

The novel PAM is shown with the required variant indicated with an underline.

Figure 3:
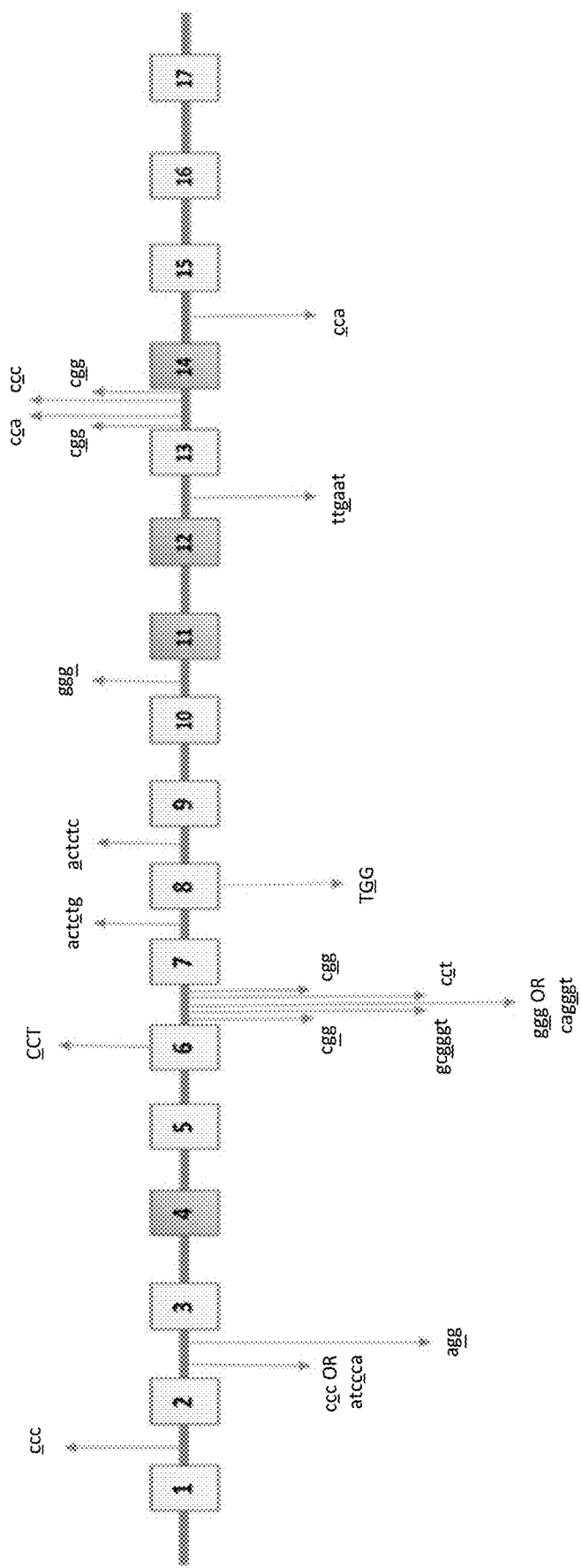
FIG. 3 shows positions of variants for novel PAM.

In Table 2, "b/w" indicates that the variant (e.g., mutation) is located between two exons. For example, "b/w 1 & 2" means that the variant is located between exon 1 and exon 2 (e.g., the variant is located in intron), as shown in FIG. 3. In FIG. 3, the numbered boxes indicate the exons within TGFBI. The hotspots in TGFBI, where multiple disease-causing mutations are found, are shown by the red boxes. Each blue arrow indicates the position of a SNP that generates a novel PAM. The novel PAM is shown for each arrow, with the required variant highlighted in red.

Figure 4:
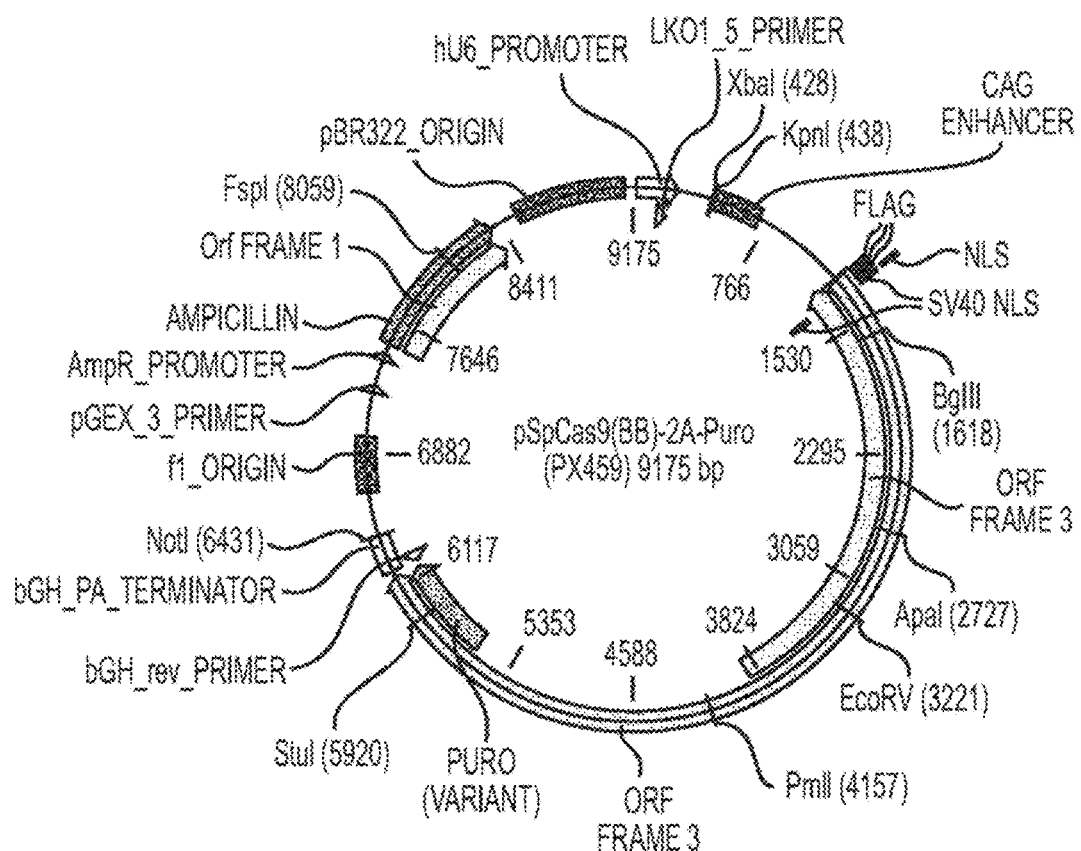
FIG. 4 illustrates exemplary vectors for CRISPR/Cas9 system, including pSpCas9(BB)-2A-Puro (PX459) using *Streptococcus pyogenes* Cas9 nuclease.

Constructs: Three plasmids expressing Cas9 and an sgRNA were used throughout all experiments. The non-targeting plasmid used was pSpCas9(BB)-2A-Puro (PX459) (Broad Institute, MIT; Addgene plasmid 48139; FIG. 4).

Figure 5:
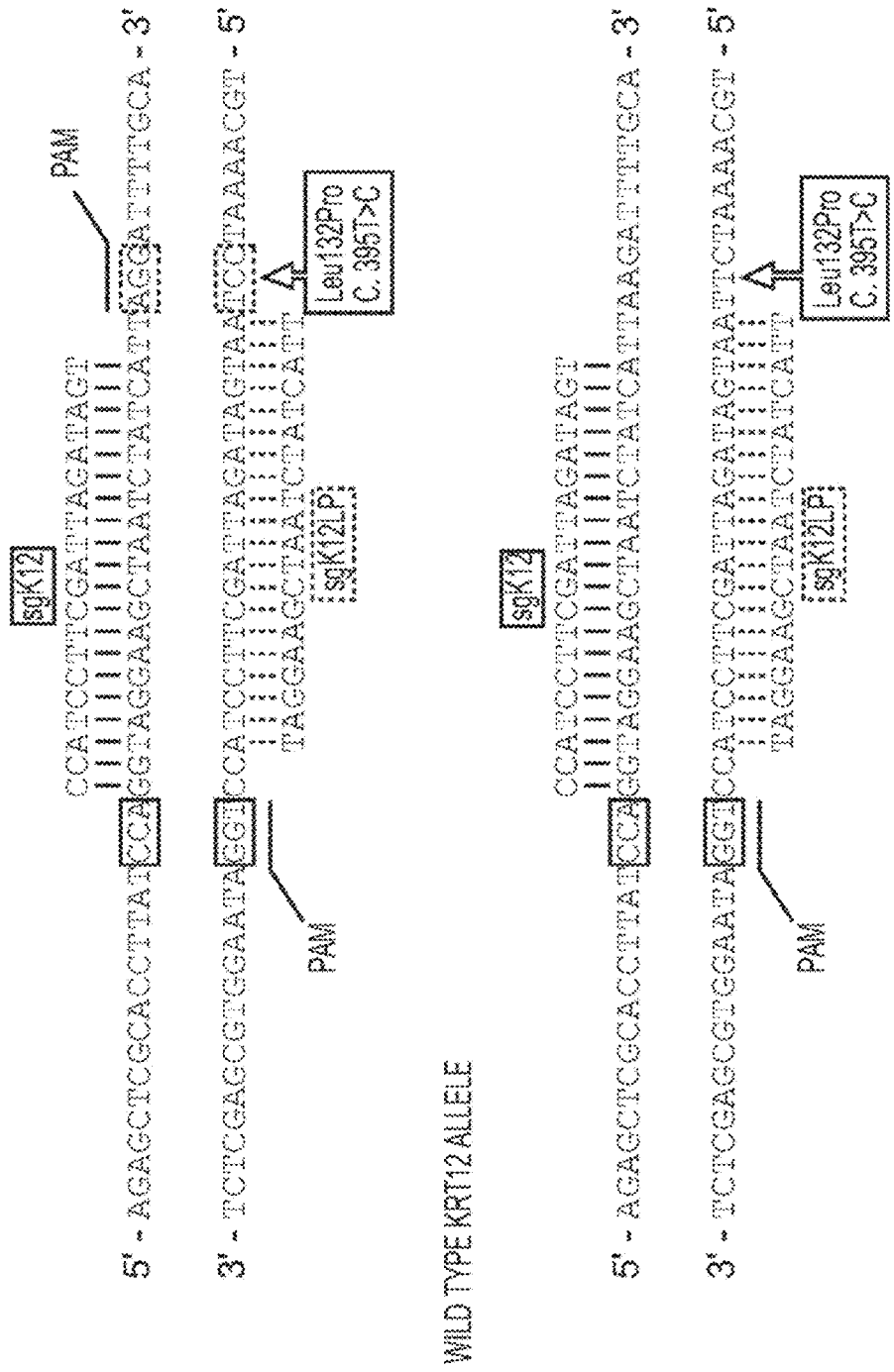
FIG. 5 illustrates exemplary design of sgRNAs for targeting wild-type and mutant keratin 12 (K12) alleles. An sgRNA to use the SNP-derived PAM found on the K12-L132P allele was designed (red). PAM is absent from the wild-type allele. A second sgRNA to target both wild-type and mutant K12 alleles (green) was also designed and used as a positive control. Figure discloses SEQ ID NOS 16-17, 9, 16, 18, and 9 respectively, in order of appearance.

Following a published protocol (Ran F A, et al., Nat Protoc 2013; 8: 2281-2308), the plasmid containing the sgRNA specific to the K12-L132P allele was designed by annealing and cloning the following 2 primers (Life Technologies, Paisley, UK): 5'-CACCGTAGGAAGCTAATCTATCATT-3' (SEQ ID NO: 10) and 5'-AAACAATGATAGATT-AGCTTCCTAC-3' (SEQ ID NO: 11) into pSpCas9(BB)-2A-Puro. sgRNA corresponds to the 20 nucleotides directly 3' of the allele-specific PAM found on the K12-L132P allele (FIG. 5, red), hereafter named sgK12LP. A Cas9/sgRNA plasmid to target both wild-type and mutant K12 sequences was constructed (Sigma, Gillingham, UK) and used as a positive control (FIG. 5, green).

Additional K12 expression constructs previously described were used to assess allele specificity and potency. Firefly luciferase plasmids with the full mRNA sequence for either K12-WT or K12-L132P inserted 3' of the stop codon, hereafter named as K12WT-Luc and K12LP-Luc, respectively (Liao H, et al. PLoS One 2011; 6: e28582.), and expression plasmids for mature haemagglutinin (HA)-tagged K12-WT and K12-L132P protein (Courtney D G, et al. Invest Ophthalmol Vis Sci 2014; 55: 3352-3360.) with plasmids hereafter known as K12WT-HA and K12LP-HA, respectively, were used. An expression construct for Renilla luciferase (pRL-CMV, Promega, Southampton, UK) was used for the dual-luciferase assay to normalize transfection efficiency.

Dual-luciferase assay: A dual-luciferase assay was used to quantify potency and allele-specificity of the three test sgRNAs in exogenous constructs, using methods adapted as previously described (Courtney D G, et al. Invest Ophthalmol Vis Sci 2014; 55: 977-985; Allen EHA, et al. Invest Ophthalmol Vis Sci 2013; 54: 494-502; Atkinson S D, et al. J Invest Dermatol 2011; 131: 2079-2086). In short, HEK AD293 cells (Life Technologies) were transfected using Lipofectamine 2000 (Life Technologies) with both K12WT-Luc or K12LP-Luc expression constructs and sgNSC, sgK12 or sgK12LP constructs at a ratio of 1:4. Cells were incubated for 72 h before being lysed and the activities of both Firefly and Renilla luciferase quantified. In all, eight replicates were carried out for each transfection condition.

Western blotting: HA-tagged wild-type (K12WT-HA) and mutant (K12LP-HA) expression constructs (Liao H, et al. PLoS One 2011; 6: e28582.) were transiently co-transfected with each of the sgRNAs at a ratio of 1:4 into HEK AD293 cells in duplicate using Lipofectamine 2000 (Invitrogen), using similar methods as previously described (Courtney D G, et al. Invest Ophthalmol Vis Sci 2014; 55: 977-985; Allen EHA, et al. Invest Ophthalmol Vis Sci 2013; 54: 494-502). Transfected cells were incubated for 72 h. Expression of HA-tagged K12 and β-actin was analyzed using a rabbit polyclonal antibody to HA (Abcam, Cambridge, UK; ab9110, 1:2000) and a mouse monoclonal antibody to human β-actin (Sigma, 1:15 000) using standard methods (Courtney D G, et al. Invest Ophthalmol Vis Sci 2014; 55: 977-985; Allen EHA, et al. Invest Ophthalmol Vis Sci 2013; 54: 494-502). Membranes were incubated with a secondary horseradish peroxide-conjugated polyclonal swine anti-rabbit antibody (DakoCytomation, Ely, UK) or a horseradish peroxide-conjugated goat anti-mouse antibody (DakoCytomation), respectively. Protein binding was detected by standard chemiluminescence (Life Technologies). Densitometry was performed using ImageJ (Schneider C A, Rasband W S, Eliceiri K W. Nat Methods 2012; 9: 671-675), to quantify the band intensity of the HA-tagged K12 (n=4). was normalized to the band intensity of β-actin.

Quantitative real-time PCR: Transfections were carried out in the same manner as described for western blotting; however, both K12WT-HA and K12LP-HA were simultaneously transfected into cells. All transfections were carried out in triplicate. Following transfection, cells were incubated for 48 h and RNA extracted using the RNAeasy Plus kit (Qiagen, Venlo, The Netherlands). Following cDNA conversion of 500 ng of RNA (Life Technologies) quantitative real-time PCR was performed to quantify levels of KRT12 mRNA. A KRT12 assay was used (assay Id 140679; Roche, West Sussex, UK) alongside an HPRT assay (assay ID 102079; Roche) and a GAPDH assay (assay ID 141139; Roche). Each sample was run in triplicate for each assay and relative gene expression was calculated using the ΔΔCT method (Livak K J, Schmittgen T D. Methods 2001; 25: 402-408). KRT12 expression levels were normalized against HPRT and GAPDH, where expression of both reference genes was deemed to be 'stable' across treatment groups, using the BestKeeper software tool (Pfaffl M W, Tichopad A, Prgomet C, Neuvians T P. Biotechnol Lett 2004; 26: 509-515).

Pyrosequencing: Using the same cDNA samples assessed by quantitative reverse transcriptase-PCR, pyrosequencing was carried out to determine the ratio of remaining K12-L132P mRNA to K12-WT mRNA, exactly as described previously (Courtney D G, et al. Invest Ophthalmol Vis Sci 2014; 55: 3352-3360).

KRT12 transgenic mouse: A C57 mouse model was obtained, with a human K12-L132P allele knocked in to replace the endogenous mouse Krt12 coding sequence. allowed for the in-vivo targeting of KRT12-L132P by the allele-specific sgRNA and Cas9. Female heterozygous mice at 24 weeks old were used, where one copy of the human K12-L132P allele and one copy of murine Krt12 were present. Standard PCR and Sanger dideoxynucleotide sequencing was used to genotype the mice and confirm heterozygosity of the K12-L132P allele. Randomization of animals was not required, as study investigated the effect of treatment on one cornea, whereas the other cornea of the same animal was used as the negative control. Investigators were not blinded in study. All experimentation complied with ethical regulations and was approved by the local ethics committee.

In-vivo intrastromal ocular injection: To achieve transient expression of the allele-specific sgRNA and the Cas9, the sgK12LP plasmid was introduced into the corneal stroma of the heterozygous knock-in mice by intrastromal ocular injection, following previously described protocols (Moore J E, McMullen C B T, Mahon G, Adamis A P. DNA Cell Biol 21: 443-451). To assess delivery method, wild-type mice were first injected with 4 µg of a Cas9-GFP plasmid (pCas9D10A_GFP) (Addgene plasmid 44720). Mice were culled at 24, 48 and 72 h, and corneas fixed in 4% paraformaldehyde and processed using standard histological procedures. Five-micrometer-thick sections were cut, rehydrated and imaged by fluorescent microscopy. Mice were administered with general anesthetic and a local anesthetic to the cornea. A qualified ophthalmologist injected 4 µg of sgK12LP or sgNSC plasmid diluted in a total of 3 µl phosphate-buffered saline into the cornea of the right eye and the left eye, respectively, of four mice. Mice were culled 48 h post treatment.

Sequencing and determination of NHEJ: Once the mice were culled, the eyes were enucleated and the corneas were dissected. gDNA was extracted using a DNA extraction kit (Qiagen) and samples were pooled into two treatment groups: sgK12LP and sgNSC. Samples underwent PCR amplification using the following two primers to amplify the region around the K12-L132P mutation: 5'-ACACC-CATCTTGCAGCCTAT-3' (SEQ ID NO: 12) and 5'-AAAATTCCCAAAGCGCCTC-3' (SEQ ID NO: 13). PCR products were gel purified and ligated into the CloneJet cloning vector (Life Technologies) and were used to transform DH5α competent cells (Life Technologies). A total of 13 clones were selected and plasmid DNA prepared using a miniprep kit (Qiagen) following manufacturer's procedures. DNA from the 13 clones was then sequenced (Department of Zoology, University of Oxford) using the sequencing primers provided with the CloneJet vector. The two most likely exonic off-target sites for sgK12LP in the mouse genome, as predicted by the Zhang Lab online tool (crispr.mit.edu) were assessed in the same way, where 10 colonies were selected for analysis for each predicted off target. The predicted off-target sites were 5'-TAAGTAGCTGATC-TATCAGTGGG-3' (SEQ ID NO: 14) (Gon41) and 5'-TGG-GAAGCATATCTGTCATTTGG-3' (SEQ ID NO: 15) (Asphd1). Only these two sites were selected, as they were the only two to have a calculated off-target score >0.1.

Statistics: All error bars represent the s.e.m. unless stated otherwise. Significance was calculated using an unpaired t-test, as all samples demonstrated the same distribution. Statistical significance was set at 0.05%. Variance was calculated among groups and deemed to be similar.

Construction of a KRT12-specific sgRNA: An analysis of the sequence changes that result from MECD-causing KRT12 missense mutations revealed that the L132P mutation that causes the severe form of MECD coincidentally results in the generation of a novel PAM site (AAG>AGG). An sgRNA (sgK12LP) complementary to the sequence 20 nucleotides adjacent to the 5'-end of the novel PAM site generated by the KRT12 L132P mutation was designed and assessed for potential off targets using the 'Optimized CRISPR Design Tool' provided online by the Zhang lab, MIT 2013, (FIG. 5, red). The sgRNA was calculated as having a score of 66% using system, where a score >50% is deemed to be of high quality with a limited number of predicted possible off targets.

Figure 6:
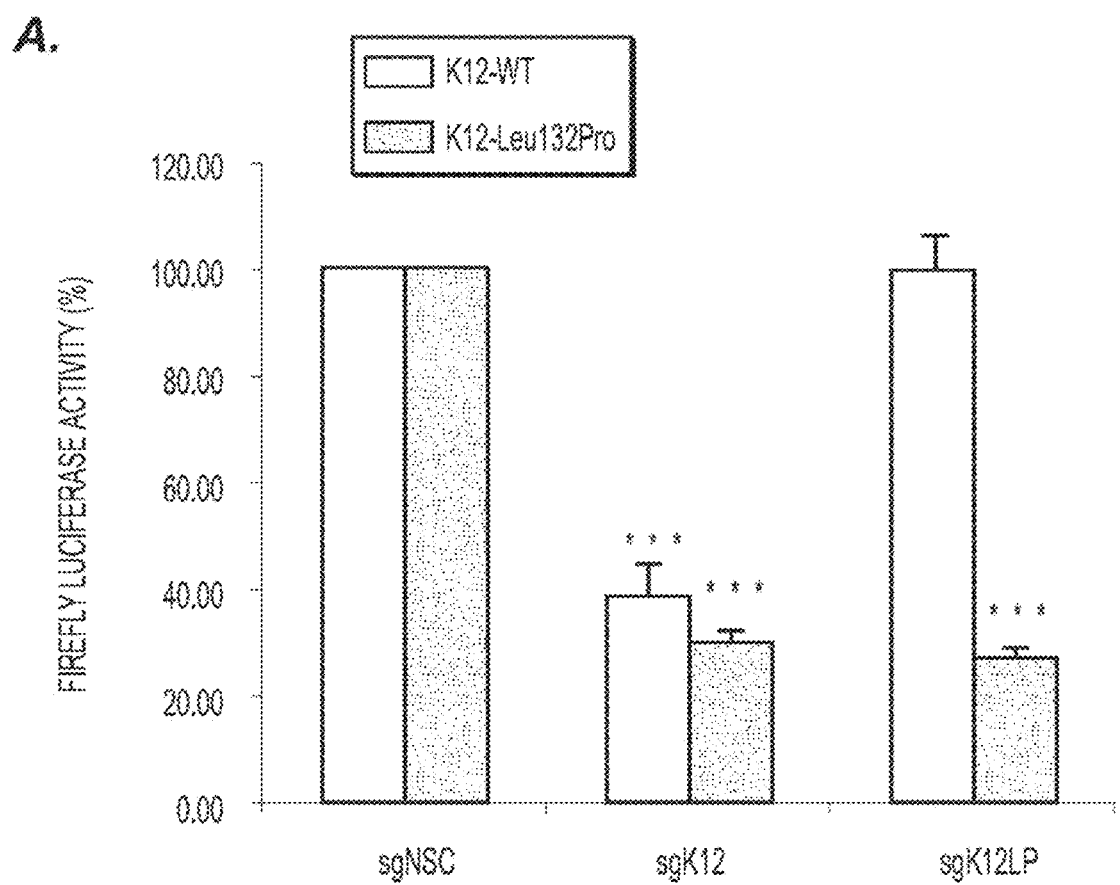
FIG. 6 illustrates evaluation of allele specificity and potency of sgK12LP using exogenous expression constructs. Exogenous expression constructs for wild-type and mutant K12 were employed to test the allele-specificity and potency of sgK12LP. (a) A dual luciferase assay demonstrated the allele-specificity of the sgK12LP plasmid, whereas potency was shown to be comparable to that of the sgK12 construct. N=8 (b) Western blotting further demonstrated these attributes with a noticeable reduction in K12-L132P protein in cells treated with sgK12LP in comparison with cells treated but expressing K12 wild-type protein. β-Actin was used as a loading control. (c) Quantitative reverse transcriptase-PCR for total K12 in cells expressing both wild-type and mutant alleles demonstrated a knockdown in mRNA expression. N=4 (d) Allele proportions of mRNA knockdown were then quantified by pyrosequencing, confirming an allele knockdown of the mutant allele in cells co-expressing both KRT12 alleles and treated with sgK12LP. N=4, *P<0.05, P<0.01, *P<0.001.
Figure 6:
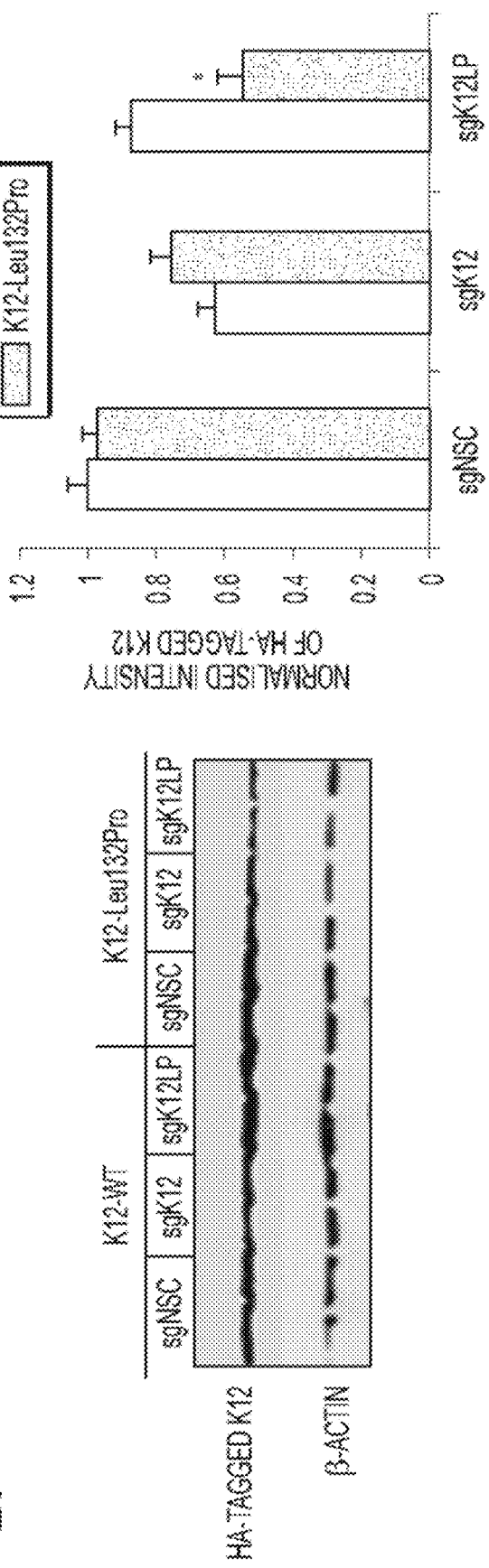
Figure 6:
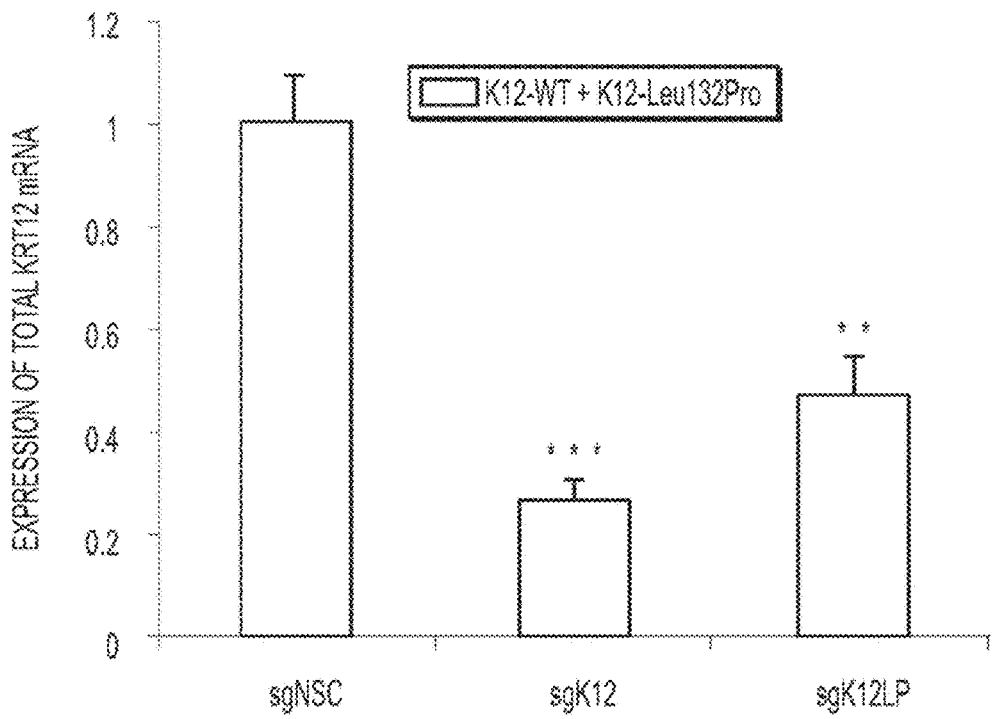
Figure 6:
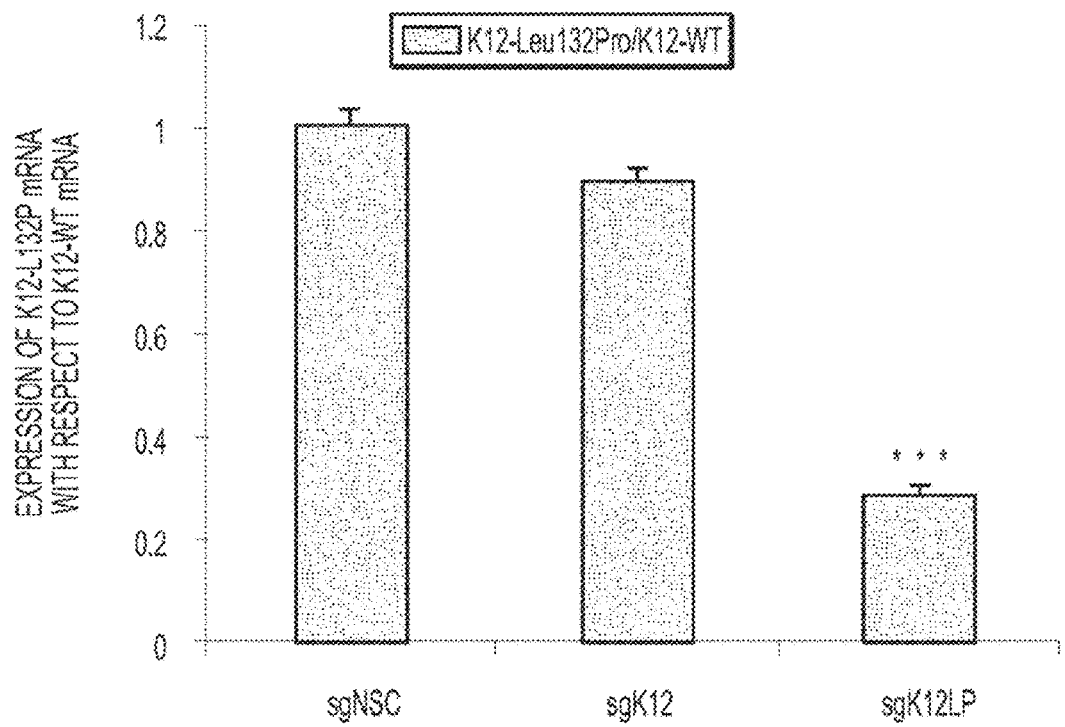

Assessment of sgK12LP allele specificity and potency in vitro: The allele-specificity and potency of sgK12LP was assessed in vitro, in HEK AD293 cells, using exogenous expression constructs for wild-type and mutant K12. Allele specificity was first determined using a dual-luciferase reporter assay (FIG. 6 item a). Firefly luciferase activity was found to be significantly decreased in cells expressing either K12WT-Luc or K12LP-Luc and treated with sgK12. A potent and allele-specific reduction of firefly luciferase activity was observed in cells treated with sgK12LP. In cells expressing K12LP-Luc, a reduction of 73.4±2.7% (P<0.001) was observed (FIG. 6 item a). allele-specific and potent knockdown was also observed by western blotting, in cells expressing either K12WT-HA or K12LP-HA (FIG. 6 item b; image representative of four blots) and quantification by densitometry revealed a significant reduction of 32% in K12LP-HA protein by sgK12LP in comparison with K12WT-HA protein (P<0.05). In cells treated with sgK12, both wild-type and mutant K12 protein was found to have decreased, whereas in those treated with sgK12LP there appeared to be no effect on expression of the wild-type protein but a significant knockdown of the mutant K12 protein (FIG. 6 item b).

To support data, observed at the protein level, quantitative reverse transcriptase-PCR and pyrosequencing were carried out to determine allele specificity and potency at the mRNA level. In cells expressing both wild-type and mutant K12 simultaneously (in a 1:1 expression ratio) and treated with each of the three test Cas9/sgRNA expression constructs (NSC, K12 and K12LP), quantitative reverse transcriptase-PCR was used to determine knockdown of total K12 mRNA (FIG. 6 item c). A potent reduction of 73.1±4.2% (P<0.001) of total K12 mRNA was observed in sgK12-treated cells, with a lesser reduction of 52.6±7.0% (P<0.01) measured in sgK12LP-treated cells (FIG. 6 item c). Pyrosequencing was used to determine the intracellular proportion of the remaining mature mRNA species after treatment with these sgRNAs (FIG. 6 item d). Proportions of mRNA were calculated as percentage of K12-L132P'/percentage of K12-WT'. Cells treated with sgNSC were normalized to 1, assuming a ratio of 1:1 between mutant and wild-type K12 mRNA. In cells tested with sgK12, a K12 mutant mRNA proportion of 0.89±0.03 was observed, but the difference to the NSC control was not significant (P<0.14). In those cells treated with sgK12LP, a K12 mutant mRNA proportion of 0.28±0.02 was detected and was significantly altered in comparison with the sgNSC-treated cells (P<0.001) (FIG. 6 item d).

Figure 7:
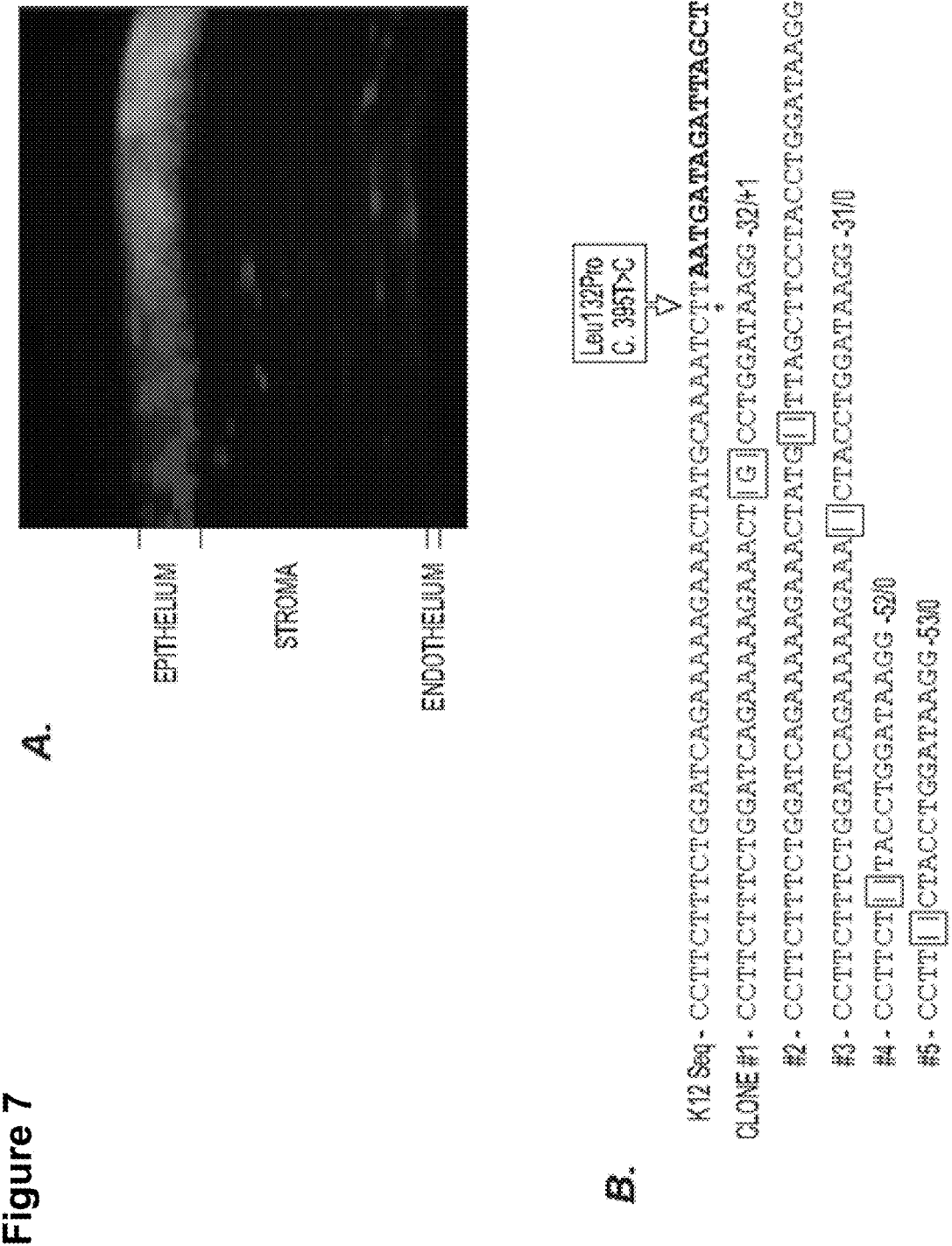
FIG. 7 illustrates sgK12LP-induced NHEJ in vivo. GFP expression was observed in the corneal epithelium of mice at 24 h post intrastromal injection, demonstrating the efficacy of an intrastromal plasmid injection for transfecting the corneal epithelium (a; N=2). No GFP expression was observed at 48 h post injection. Sequencing of the gDNA from human K12-L132P heterozygous mice injected with the sgK12LP construct demonstrated large deletions and the induction of NHEJ due to cleavage of the KRT12-L132P allele. Of 13 clones sequenced, 5 were found to have undergone NHEJ (b). Figure discloses SEQ ID NOS 19-24, respectively, in order of appearance.

Determination of the efficacy of sgRNA-K12LP in vivo: Intrastromal injection of the Cas9-GFP construct resulted in the presence of green fluorescent protein (GFP) protein in the corneal epithelium at 24 h post injection (FIG. 7 item a). Transient expression of GFP was found up to 48 h post injection. Following intrastromal injection of either the sgK12LP or sgNSC expression constructs into K12-L132P humanized heterozygous mice and an incubation period of 48 h, mice were euthanized and genomic DNA (gDNA) prepared from the corneas. gDNA from the corneas of four sgK12LP- or sgNSC-treated animals was pooled and PCR amplification of exon 1 of the humanized K12-L132P gene, cloning and sequencing was performed. Of 10 clones established from gDNA of eyes treated with sgNSC, the K12-L132P sequence remained intact in all 10. Thirteen individual clones from sgK12LP-treated eyes were sequenced; eight were found to contain an unaltered KRT12 L132P human sequence, whereas five clones demonstrated NHEJ around the predicted cleavage site of the Cas9/sgK12LP complex (FIG. 7 item b). In one clone (1), an insertion of 1 nucleotide was found, with a deletion of 32 nucleotides. Large deletions of up to 53 nucleotides were observed in vivo (clone 5). Of these 5 clones, 4 contained deletions (clones 1 and 3-5) that are predicted to result in a frameshift that would lead to the occurrence of an early stop codon. The top 2 predicted exonic off-target sites of sgK12LP in mouse were also assessed using method. Ten clones were sequenced for each target and none were found to have undergone nonspecific cleavage.

TGFBI Mutations associated with a PAM site created by mutation in R514P, L518R and L509R: Single guide RNAs were designed to target each of these mutations and cloned into the sgRNA/Cas9 expression plasmid. In addition, a positive control guide RNA utilizing a naturally-occurring near-by PAM was designed for each mutation. Wild-type and mutant target sequences were cloned into a luciferase reporter plasmid to allow us to monitor the effect of gene editing on expression of WT and MUT expression. Both plasmids were used to transfect AD293 cells and luciferase expression was measured 48 hours after CRISPR Cas9 treatment using our high throughput reporter gene assay to give a measurement of the amount of MUT and WT DNA present in the cells.

Figure 8:
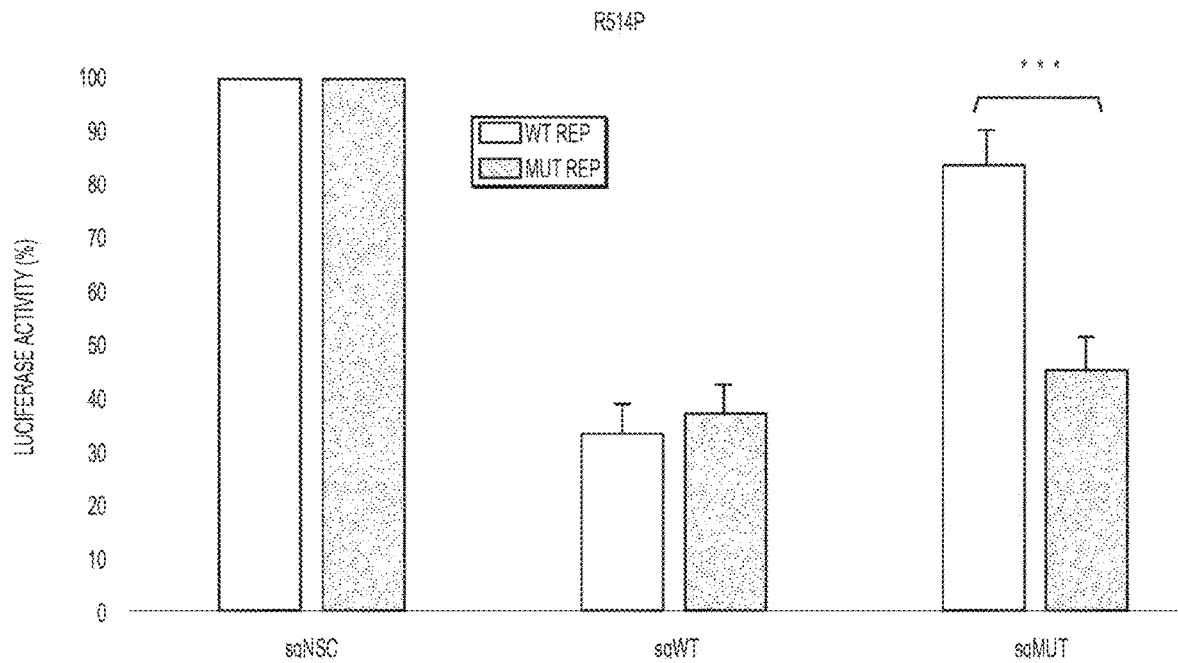
FIG. 8 shows results using SNP derived PAM guide RNAs designed for TGFBI mutations R514P (A), L518R (B), and L509R (C), and luciferase expression was used to assess wild type and mutant allele expression. A positive control (sgW or sgWT) guide was designed to cut both WT (blue bar) and MUT (red bar) allele and as shown above cuts both alleles as expected. The guide used for L518R (sgM or sgMUT) shows the greatest allele specificity with minimal cutting of the mutant allele (red bar). The negative control guide (sgN or sgNSC) as expected did not cut either of the WT nor MUT DNA.
Figure 8:
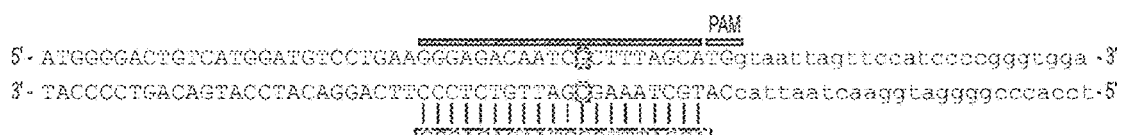
Figure 8:
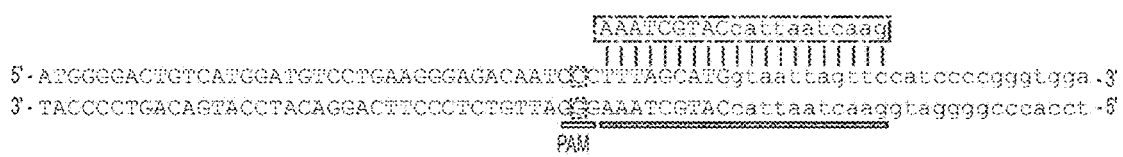
Figure 8:
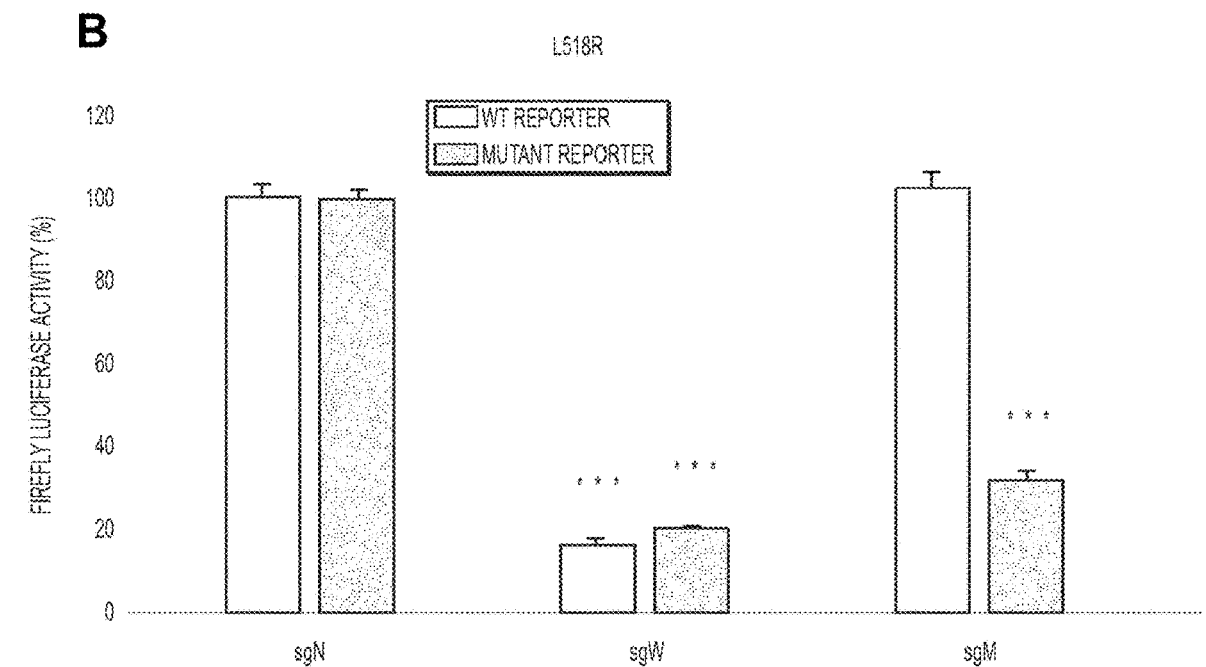
Figure 8:
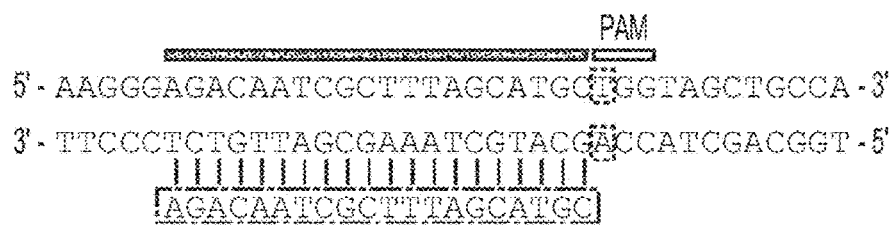
Figure 8:
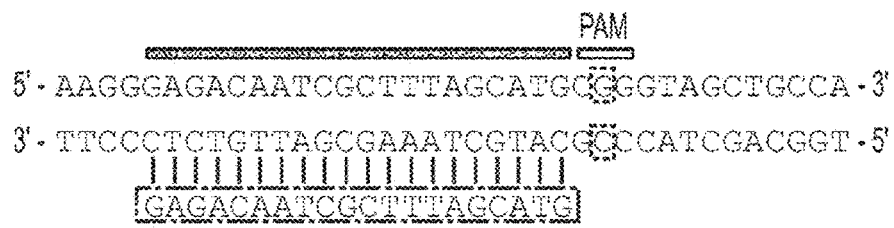
Figure 8:
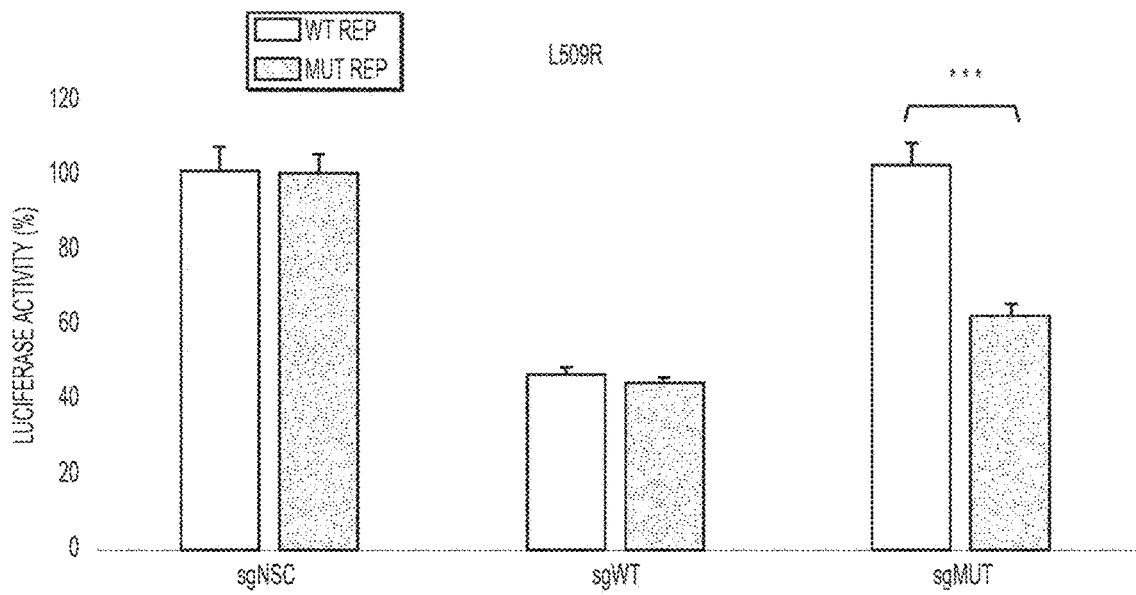
Figure 8:
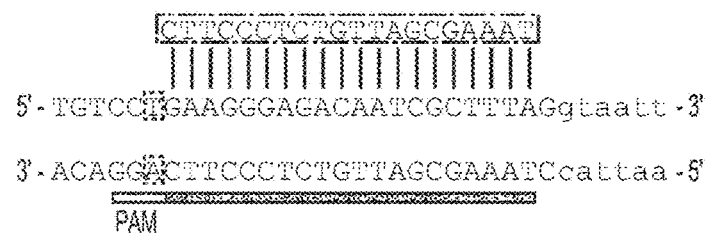
Figure 8:
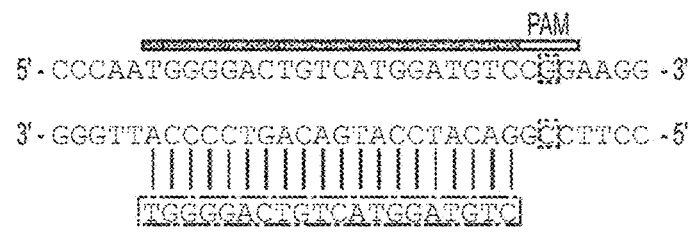

FIG. 8 shows that for 3 TGFBI mutations (R514P, L518R, and L509R) assessed using the SNP derived PAM approach significant allele-specificity was achieved, with the mutant allele cut by the CRISPR Cas9 system and the WT DNA cut to some degree for some of the guides.

Figure 9:
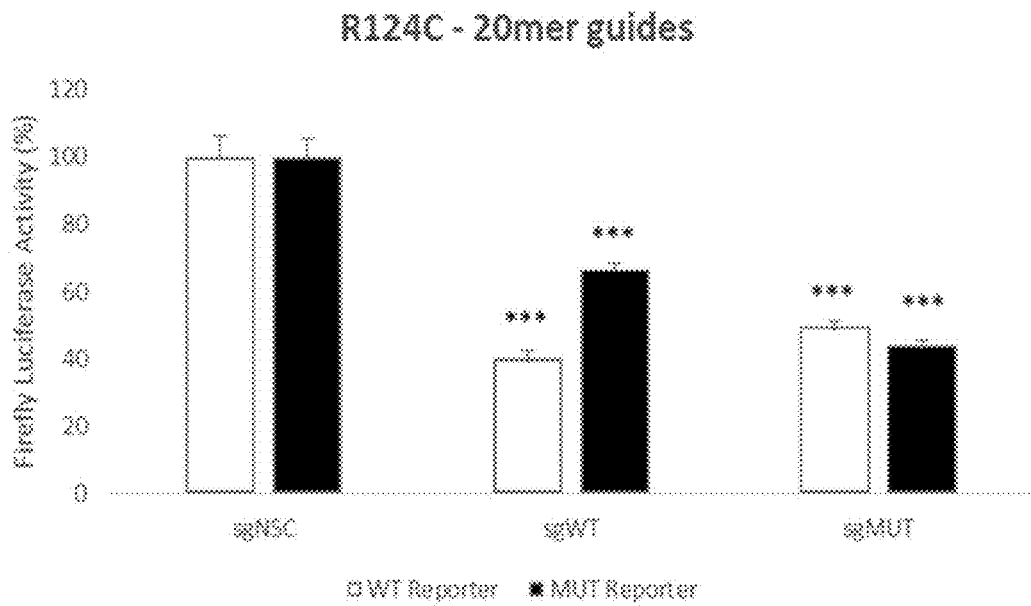
FIG. 9 shows results using mutant allele specific guide RNAs designed for R124. TGFBI mutations and luciferase expression was used to assess wild type and mutant allele expression. A positive control sgWT guide was designed to cut both WT and MUT allele and as shown above cuts both alleles as expected (middle bars in each graph blue and red bars). The guides with the 20 mer length showed more WT allele DNA editing. The assay was repeated with allele specific RNA guides shortened to 18 mer. reduced the amount of WT DNA cutting (right hand panel of graphs and right side bars on graph (blue bars).
Figure 9:
Figure 9:
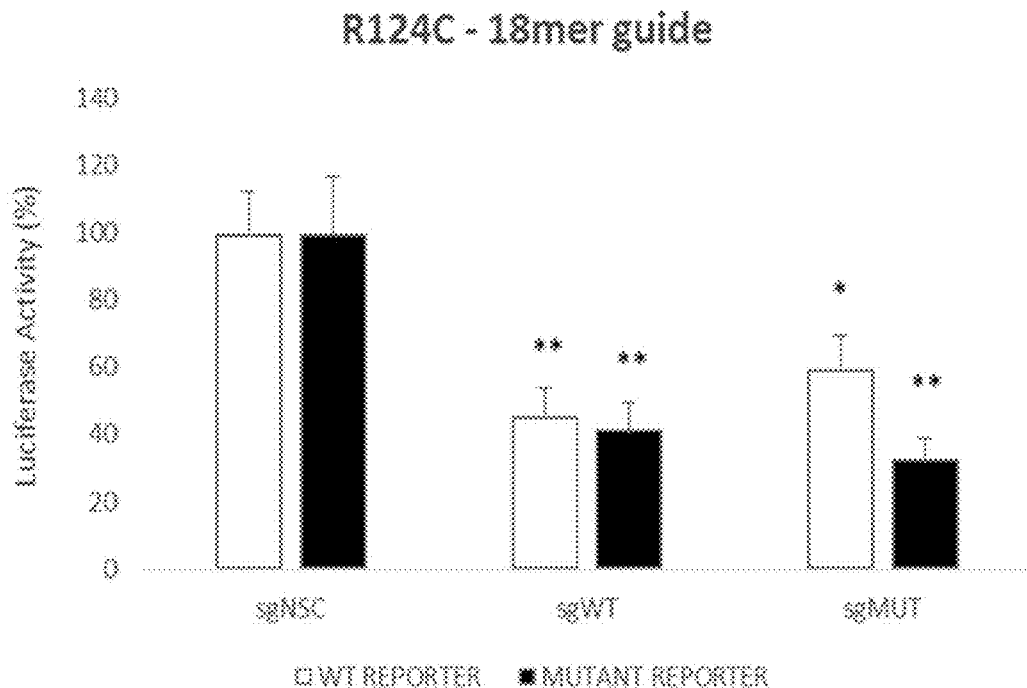
Figure 9:
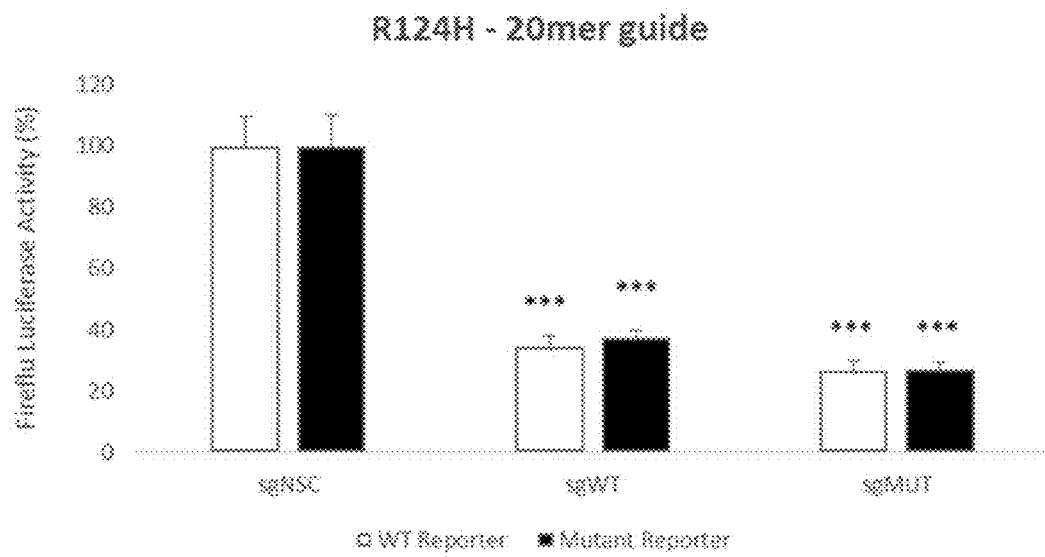
Figure 9:
Figure 9:
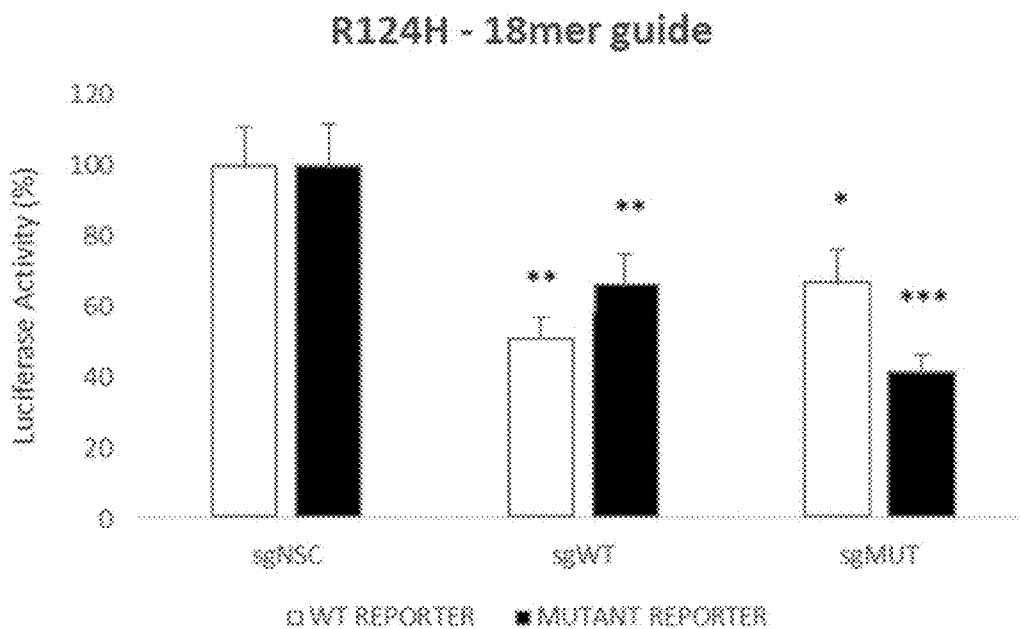
Figure 9:
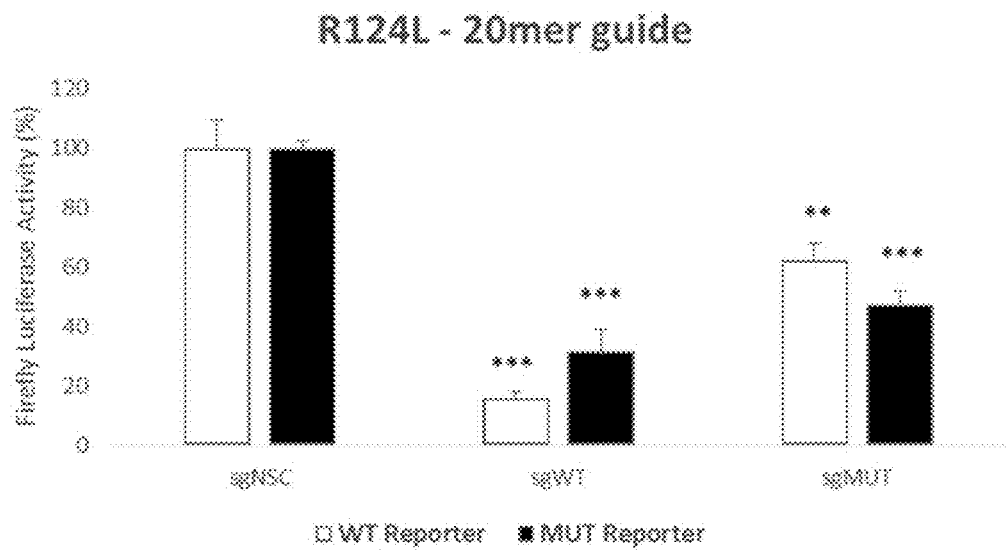
Figure 9:
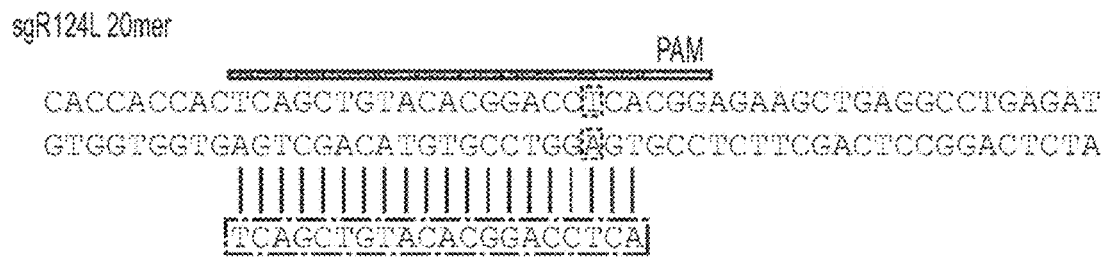
Figure 9:
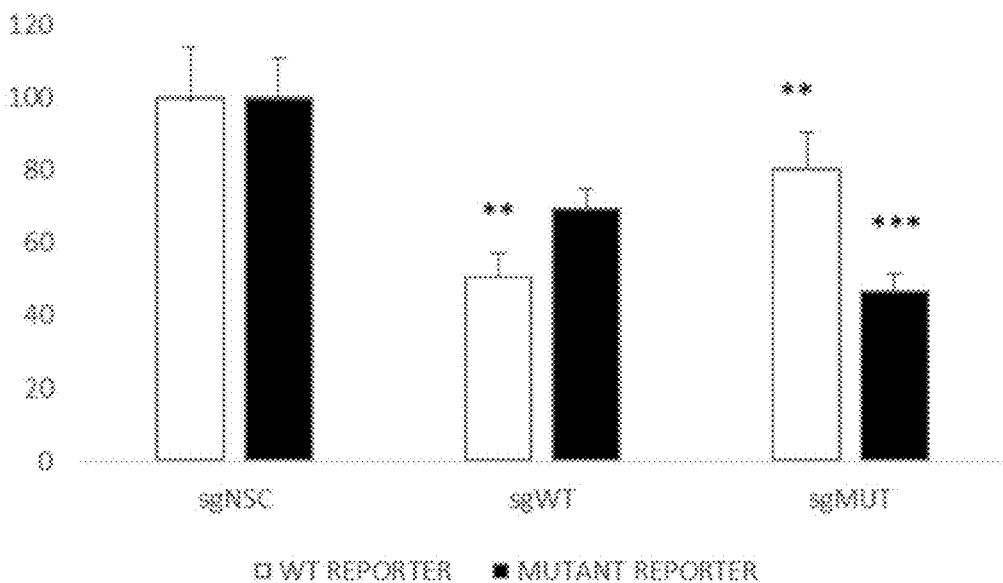

TGFBI Mutations associated with a SNP mutation that lies within a target region adjacent to a PAM site: Single guide RNAs were designed to target these mutations and cloned into the sgRNA/Cas9 expression plasmid. Wild-type and mutant target sequences were cloned into a luciferase reporter plasmid and assessed in our high throughout reporter gene assay. Both plasmids were used to transfect AD293 cells and luciferase expression measured two days afterwards. Firstly, sgRNA that contained a 20 bp target specific sequence were tested. However, these failed to provide sufficient allele specificity. Subsequently, truncated sgRNA (TRU-guides) were designed that reduced the target sequence to 18 bp. An improved allele-specificity was noted (FIG. 9 items a-f).

Ex Vivo Gene Correction: The ability to achieve gene-silencing in corneas from the luciferase reporter mouse was demonstrated. Mice heterozygous for Luc2 were culled, and their corneas were dissected and then transferred to cell culture medium. The dissected corneas were transfected with either a non-specific control sgRNA or a sgRNA targeted to the luciferase reporter gene using Lipofectamine 2000. Corneas were maintained in culture for 3 days, and the luciferase expression was measured.

Figure 10:
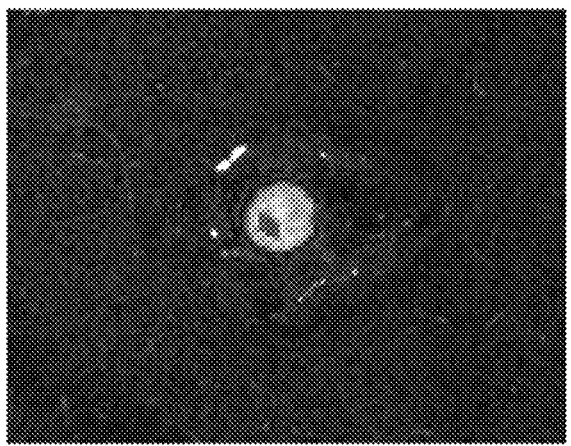
FIG. 10 shows that the left eye was transfected with a non-specific negative control sgRNA, while the right eye was transfected with a sgRNA targeting Luc2.
Figure 10:
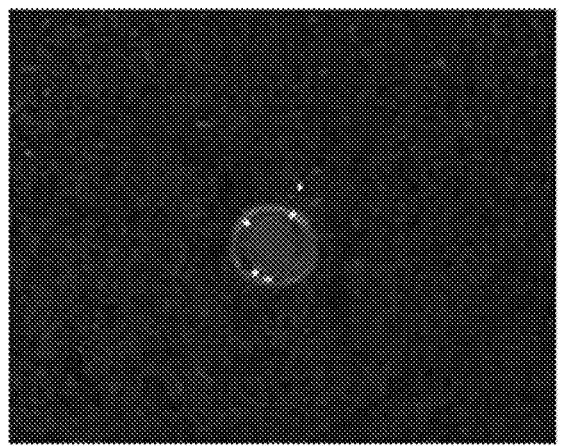

Potent silencing of the luciferase reporter gene (FIG. 10) was observed in corneas transfected with the sgRNA targeting Luc2 representing successful CRISPR gene editing of the target gene ex vivo. The cornea from a mouse heterozygous for Luc2 was dissected and CRISPR gene editing performed ex vivo. The mouse corneal epithelial stem cell is not restricted to the limbal region and therefore we needed to show gene editing across the entire epithelium as shown in FIG. 10. The dark color of the figure on the right after treatment demonstrated complete gene editing and knock out of the Luc gene in entire mouse cornea ex vivo. (Moore J E, McMullen C B T, Mahon G, Adamis A P (2002). The Corneal Epithelial Stem Cell. DNA & Cell Biology, 21 (5-6) pp. 443-451.)

Surgical Graft for Treatment of Granular Corneal Dystrophy Type II

Cells are cultivated from a limbal biopsy sample obtained from a patient undergoing treatment for granular corneal dystrophy type II. The patient undergoing treatment carries a mutation in a TGFBI gene that encodes for one of the following amino acid substitutions: R124C, R124H, R124L, R555W, R555Q, and H626P. Cells are washed and limbal epithelial stem cells (LESCs) are sorted based on one or more of the following markers: transcription factor p63, ABCG2, C/EBPδ or Bmi-1. A cell line is established from the isolated LESCs in the presence of 3T3 feeder cells. The established LESC line is then confirmed by the presence of one or more of the following positive markers: transcription factor p63, ABCG2, C/EBPδ or Bmi-1, and the absence of one or more of the following negative markers: cytokeratin 3 (CK3), cytokeratin 12 (CK12), connexin 43 or involucrin.

CRISPR system reagents are prepared according to Shalem et al., Nature Reviews Genetics 16: 299-311 (2013); Zhang et al., Human Molecular Genetics 23(R1): R40-6 (2014); Zetsche et al. dx.doi.org/10.1016/j.cell.2015.09.038 (2015) and Zhu et al. Cell 157: 1262-1278 (2014). The CRISPR system reagents include one or more guide RNAs (gRNAs), and a Type-II nuclease (e.g., Cas9 or Cpf1) included on the same vector and a repair nucleic acid that is approximately 150 bp long. The repair nucleic acid includes a wild type allele of R124, R555, or H626 as well as a selectable GFP marker that allows for the selection of position homologous recombination events. The CRISPR system reagents are introduced into the LESC cell line using standard polymer based (DEAE dextran) transfection techniques. LESCs are allowed to undergo nucleic acid manipulation events and cells positive for such an event are isolated using the GFP marker and FACS. The desired homologous recombination event is further confirmed by sequencing of the TGFBI region of interest in the FACS sorted LESCs.

Manipulated LESCs that contain the desired wild type TGFBI allele are cultured on an amniotic membrane for a period of time sufficient for the manipulated LESCs to expand to an appropriate area size for transplantation. Once the desired size is achieved, the manipulated LESCs can be transplanted using the amniotic membrane as a carrier.

What is claimed is:

1. A method of ameliorating or treating corneal dystrophy in a subject in need thereof, the method comprising:

manipulating a nucleic acid mutation in a corneal dystrophy target nucleic acid in a limbal epithelial stem cell to correct the nucleic acid mutation, thereby forming a manipulated limbal epithelial stem cell, wherein the manipulating comprises introducing an engineered Clustered Regularly Interspaced Short Palindromic Repeats (CRISPR)/CRISPR associated protein 9 (Cas9) system into the limbal epithelial stem cell, wherein the CRISPR/Cas9 system comprises at least one vector comprising a nucleotide molecule encoding Cas9 nuclease and an single guide RNA (sgRNA), and the Cas9 nuclease and said sgRNA do not naturally occur together, wherein the sgRNA comprises (i) CRISPR targeting RNA (crRNA) sequence, and (ii) a trans-activating crRNA (tracrRNA) sequence, wherein the tracrRNA comprises a nucleotide sequence having the nucleotide sequence of SEQ ID NO: 6, wherein the crRNA sequence and tracrRNA sequence do not naturally occur together; and transplanting the manipulated limbal epithelial stem cell into the subject.

2. The method according to claim 1, comprising:

manipulating the nucleic acid mutation in a plurality of limbal epithelial stem cells to correct the nucleic acid mutation, thereby forming one or more manipulated limbal epithelial stem cells;

isolating the one or more manipulated limbal epithelial stem cells; and transplanting the one or more manipulated limbal epithelial stem cells into the subject.

3. The method according to claim 2, further comprising culturing the one or more manipulated limbal epithelial stem cells prior to transplanting, thereby forming a plurality of manipulated limbal epithelial stem cells,
- wherein the transplanting comprises transplanting the plurality of manipulated limbal epithelial stem cells.

4. The method according to claim 3, wherein the culturing comprises establishing a stable cell line.

5. The method according to claim 1, further comprising culturing the manipulated limbal epithelial stem cell prior to transplanting, thereby forming a plurality of manipulated limbal epithelial stem cells,
- wherein the transplanting comprises transplanting the plurality of manipulated limbal epithelial stem cells.

6. The method according to claim 1, wherein the limbal epithelial stem cell is obtained from an autologous or homologous donor.

7. The method according to claim 1, wherein the limbal epithelial stem cells that include the nucleic acid mutation in a corneal dystrophy target nucleic acid are obtained from the subject.

8. The method according to claim 1, wherein the corneal dystrophy target nucleic acid is a TGFβI target nucleic acid, and wherein the nucleic acid mutation encodes for an amino acid substitution of R124, R555, or H626 of the TGFβI polypeptide.

9. The method according to claim 1, wherein the corneal dystrophy target nucleic acid is a TGFβI, KRT3, KRT12, GSN or UBIAD1 target nucleic acid.

10. The method according to claim 1, wherein the corneal dystrophy occurs following laser eye surgery.

11. The method according to claim 1, further comprising repeating the transplanting at one or more predetermined frequencies.

12. The method according to claim 1, wherein the sgRNA comprises a detectable label.

13. The method according to claim 12, wherein the detectable label of the sgRNA is a nucleic acid barcode or fluorescent barcode label.

14. The method according to claim 1, wherein the manipulating further comprises introducing into the limbal epithelial stem cell:
- a repair nucleic acid comprising a wild type version of the corneal dystrophy target nucleic acid or fragment thereof,
- whereby the sgRNA targets the target nucleic acid and the nuclease cleaves the target nucleic acid thereby creating a target nucleic acid cleavage site and whereby the repair nucleic acid is capable of homologously recombining with the corneal dystrophy target nucleic acid after the creation of the target nucleic cleavage site.

15. The method according to claim 14, wherein the repair nucleic acid comprises a detectable label.

16. The method according to claim 15, wherein the detectable label of the repair nucleic acid is a nucleic acid barcode or fluorescent barcode label.

17. The method according to claim 14, wherein CRISPR/nuclease system reagents further comprise one or more agents that increase frequency of homologous recombination in the plurality of limbal epithelial stem cells by repressing genes involved in non-homologous end-joining (NHEJ) pathway.

18. The method according to claim 1, wherein the Cas9 nuclease is a *Streptococcus* Cas9, a *Staphylococcus* Cas9, or variants thereof.

19. The method according to claim 1, wherein the Cas9 nuclease comprises an amino acid sequence having at least 85% sequence identity with an amino acid sequence selected from the group consisting of SEQ ID NO: 4 or 8.

20. The method according to claim 1, wherein the sgRNA and the Cas9 nuclease are included on the same vector.

* * * * *

SEQUENCE LISTING

<160> NUMBER OF SEQ ID NOS: 45

<210> SEQ ID NO 1
<211> LENGTH: 102
<212> TYPE: RNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Spy Cas9 sgRNA
<220> FEATURE:
<221> NAME/KEY: modified_base
<222> LOCATION: (1)..(20)
<223> OTHER INFORMATION: a, c, u, or g

<400> SEQUENCE: 1
nnnnnnnnnn nnnnnnnnnn guuuuagagc uagaaauagc aaguuaaaau aaggcuaguc    60
cguuaucaac uugaaaaagu ggcaccgagu cggugcuuuu uu    102

<210> SEQ ID NO 2
<211> LENGTH: 82
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: tracrRNA or sgRNA scaffold sequence

<400> SEQUENCE: 2
guuuuagagc uagaaauagc aaguuaaaau aaggcuaguc cguuaucaac uugaaaaagu    60
ggcaccgagu cggugcuuuu uu                                            82

<210> SEQ ID NO 3
<211> LENGTH: 3974
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Spy Cas9 nucleotide sequence

<400> SEQUENCE: 3
atggactata aggaccacga cggagactac aaggatcatg atattgatta caaagacgat    60
gacgataaga tggcccccaaa gaagaagcgg aaggtcggta ccacggagt cccagcagcc   120 gacaagaagt acagcatcgg cctggacatc ggcaccaact ctgtgggctg gccgtgatc    180 accgacgagt acaaggtgcc cagcaagaaa ttcaaggtgc tgggcaacac cgaccggcac   240
agcatcaaga gaacctgat cggagccctg ctgttcgaca cggcgaaac agccgaggcc    300 acccggctga gagaaccgc cagaagaaga tacaccagac ggaagaaccg gatctgctat   360
ctgcaagaga tcttcagcaa cgagatggcc aaggtggacg acagcttctt ccacagactg   420
gaagagtcct tcctggtgga agaggataag agcacgagc ggcacccat cttcggcaac    480 atcgtggacg aggtggccta ccacgagaag taccccacca tctaccacct gagaaagaaa   540 ctggtgaca gcaccgacaa ggccgacctg cggctgatct atctggccct ggcccacatg   600
atcaagttcc ggggccactt cctgatcgag ggcgacctga cccccgacaa cagcgacgtg   660
gacaagctgt tcatccagct ggtgcagacc tacaaccagc tgttcgagga aaaccccatc   720
aacgccagcg gcgtggacgc caaggccatc ctgtctgcca gactgagcaa gagcagacgg   780
ctggaaaatc tgatcgccca gctgcccggc gagaagaaga tggcctgtt cggaaacctg    840 attgccctga gctgggcct gacccccaac ttcaagagca acttcgacct ggccgaggat    900
gccaaactgc agctgagcaa ggacacctac gacgacgacc tggacaacct gctggcccag   960
atcggcgacc agtacgccga cctgtttctg gccgccaaga acctgtccga cgccatcctg  1020
ctgagcgaca tcctgagagt gaacaccgag atcaccaagg cccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt catcaagcc catcctggaa   1260 aagatggacg gcaccgagga actgctcgtg aagctgaaca gagaggacct gctgcggaag  1320
cagcggacct cgacaacgg cagcatcccc accagatcc acctgggaga gctgcacgcc   1380
attctgcggc ggcaggaaga ttttaccca ttcctgaagg acaaccggga aaagatcgag   1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg cgcttccgc ccagagcttc atcgagcgga tgaccaactt cgataagaac  1620
```

```
ctgcccaacg agaaggtgct gcccaagcac agcctgctgt acgagtactt caccgtgtat      1680
aacgagctga ccaaagtgaa atacgtgacc gagggaatga gaaagcccgc cttcctgagc      1740
ggcgagcaga aaaaggccat cgtggacctg ctgttcaaga ccaaccggaa agtgaccgtg      1800
aagcagctga aagaggacta cttcaagaaa atcgagtgct tcgactccgt ggaaatctcc      1860
ggcgtggaag atcggttcaa cgcctccctg gcacatacc acgatctgct gaaaattatc       1920
aaggacaagg acttcctgga caatgaggaa acgaggaca ttctggaaga tatcgtgctg       1980
accctgacac tgtttgagga cagagagatg atcgaggaac ggctgaaaac ctatgcccac      2040
ctgttcgacg acaaagtgat gaagcagctg aagcggcgga gatacaccgg ctggggcagg     2100
ctgagccgga agctgatcaa cggcatccgg acaagcagt ccggcaagac aatcctggat       2160
ttcctgaagt ccgacggctt cgccaacaga aacttcatgc agctgatcca cgacgacagc     2220 ctgacctta aagaggacat ccagaaagcc caggtgtccg gccagggcga tagcctgcac      2280
gagcacattg ccaatctggc cggcagcccc gccattaaga agggcatcct gcagacagtg      2340
aaggtggtgg acgagctcgt gaaagtgatg ggccggcaca gcccgagaa catcgtgatc       2400 gaaatggcca gagagaacca gaccacccag aagggacaga agaacagccg cgagagaatg     2460
aagcggatcg aagagggcat caaagagctg ggcagccaga tcctgaaaga caccccgtg      2520 gaaacacccc agctgcagaa cgagaagctg tacctgtact acctgcagaa tgggcgggat     2580
atgtacgtgg accaggaact ggacatcaac cggctgtccg actacgatgt ggaccatatc      2640
gtgcctcaga gctttctgaa ggacgactcc atcgacaaca aggtgctgac cagaagcgac     2700
aagaaccggg gcaagagcga caacgtgccc tccgaagagg tcgtgaagaa gatgaagaac     2760
tactggcggc agctgctgaa cgccaagctg attacccaga gaaagttcga caatctgacc     2820
aaggccgaga gaggcggcct gagcgaactg gataaggccg gcttcatcaa gagacagctg     2880
gtggaaaccc ggcagatcac aaagcacgtg gcacagatcc tggactcccg gatgaacact     2940
aagtacgacg agaatgacaa gctgatccgg gaagtgaaag tgatcaccct gaagtccaag     3000
ctggtgtccg atttccggaa ggattccag ttttacaaag tgcgcgagat caacaactac        3060
caccacgccc acgacgccta cctgaacgcc gtcgtgggaa ccgccctgat caaaaagtac     3120
cctaagctgg aaagcgagtt cgtgtacggc gactacaagg tgtacgacgt gcggaagatg     3180
atcgccaaga gcgagcagga aatcggcaag gctaccgcca agtacttctt ctacagcaac     3240
atcatgaact ttttcaagac cgagattacc ctggccaacg gcgagatccg gaagcggcct     3300
ctgatcgaga caaacggcga aaccggggag atcgtgtggg ataagggccg ggattttgcc     3360
accgtgcgga aagtgctgag catgccccaa gtgaatatcg tgaaaaagac cgaggtgcag     3420
acaggcggct tcagcaaaga gtctatcctg cccaagagga caagcgataa gctgatcgcc     3480
agaaagaagg actgggaccc taagaagtac ggcggcttcg acagccccac cgtggcctat     3540
tctgtgctgt tggtggccaa agtggaaaag ggcaagtcca agaaactgaa gagtgtgaaa    3600
gagctgctgg ggatcaccat catggaaaga agcagcttcg agaagaatcc catcgacttt     3660
ctggaagcca agggctacaa agaagtgaaa aaggacctga tcatcaagct gcctaagtac     3720
tccctgttcg agctggaaaa cggccggaag agaatgctgg cctctgccgg cgaactgcag     3780
aagggaaacg aactggccct gccctccaaa tatgtgaact tcctgtacct ggccagccac     3840
tatgagaagc tgaagggctc ccccgaggat aatgagcaga acagctgtt tgtggaacag      3900 cacaagcact acctggacga gatcatcgag cagatcagcg agttctccaa gagagtgatc     3960
```

-continued ctggccgacg ctaa                                                          3974

<210> SEQ ID NO 4
<211> LENGTH: 1423
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Spy Cas9 amino acid sequence

<400> SEQUENCE: 4

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
                20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr

-continued

```
            340                 345                 350
Lys Ala Pro Leu Ser Ala Ser Met Ile Lys Arg Tyr Asp Glu His His
            355                 360                 365
Gln Asp Leu Thr Leu Leu Lys Ala Leu Val Arg Gln Gln Leu Pro Glu
            370                 375             380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
                420                 425                 430
Asn Arg Glu Asp Leu Leu Arg Lys Gln Arg Thr Phe Asp Asn Gly Ser
            435                 440             445
Ile Pro His Gln Ile His Leu Gly Glu Leu His Ala Ile Leu Arg Arg
            450                 455             460
Gln Glu Asp Phe Tyr Pro Phe Leu Lys Asp Asn Arg Glu Lys Ile Glu
465             470                 475                 480
Lys Ile Leu Thr Phe Arg Ile Pro Tyr Tyr Val Gly Pro Leu Ala Arg
                485             490                 495
Gly Asn Ser Arg Phe Ala Trp Met Thr Arg Lys Ser Glu Glu Thr Ile
                500                 505                 510
Thr Pro Trp Asn Phe Glu Glu Val Val Asp Lys Gly Ala Ser Ala Gln
            515                 520                 525
Ser Phe Ile Glu Arg Met Thr Asn Phe Asp Lys Asn Leu Pro Asn Glu
            530                 535             540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
                580                 585                 590
Lys Thr Asn Arg Lys Val Thr Val Lys Gln Leu Lys Glu Asp Tyr Phe
            595                 600             605
Lys Lys Ile Glu Cys Phe Asp Ser Val Glu Ile Ser Gly Val Glu Asp
            610                 615             620
Arg Phe Asn Ala Ser Leu Gly Thr Tyr His Asp Leu Leu Lys Ile Ile
625                 630                 635                 640
Lys Asp Lys Asp Phe Leu Asp Asn Glu Glu Asn Glu Asp Ile Leu Glu
                645                 650                 655
Asp Ile Val Leu Thr Leu Thr Leu Phe Glu Asp Arg Glu Met Ile Glu
                660                 665                 670
Glu Arg Leu Lys Thr Tyr Ala His Leu Phe Asp Asp Lys Val Met Lys
            675                 680                 685
Gln Leu Lys Arg Arg Arg Tyr Thr Gly Trp Gly Arg Leu Ser Arg Lys
            690                 695             700
Leu Ile Asn Gly Ile Arg Asp Lys Gln Ser Gly Lys Thr Ile Leu Asp
705                 710                 715                 720
Phe Leu Lys Ser Asp Gly Phe Ala Asn Arg Asn Phe Met Gln Leu Ile
                725                 730                 735
His Asp Asp Ser Leu Thr Phe Lys Glu Asp Ile Gln Lys Ala Gln Val
            740                 745                 750
Ser Gly Gln Gly Asp Ser Leu His Glu His Ile Ala Asn Leu Ala Gly
            755                 760             765
```

-continued

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
            965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala
1010                1015                1020

His Asp Ala Tyr Leu Asn Ala Val Val Gly Thr Ala Leu Ile Lys
1025                1030                1035

Lys Tyr Pro Lys Leu Glu Ser Glu Phe Val Tyr Gly Asp Tyr Lys
1040                1045                1050

Val Tyr Asp Val Arg Lys Met Ile Ala Lys Ser Glu Gln Glu Ile
1055                1060                1065

Gly Lys Ala Thr Ala Lys Tyr Phe Phe Tyr Ser Asn Ile Met Asn
1070                1075                1080

Phe Phe Lys Thr Glu Ile Thr Leu Ala Asn Gly Glu Ile Arg Lys
1085                1090                1095

Arg Pro Leu Ile Glu Thr Asn Gly Glu Thr Gly Glu Ile Val Trp
1100                1105                1110

Asp Lys Gly Arg Asp Phe Ala Thr Val Arg Lys Val Leu Ser Met
1115                1120                1125

Pro Gln Val Asn Ile Val Lys Lys Thr Glu Val Gln Thr Gly Gly
1130                1135                1140

Phe Ser Lys Glu Ser Ile Leu Pro Lys Arg Asn Ser Asp Lys Leu
1145                1150                1155

Ile Ala Arg Lys Lys Asp Trp Asp Pro Lys Lys Tyr Gly Gly Phe
1160                1165                1170

-continued

```
Asp Ser Pro Thr Val Ala Tyr Ser Val Leu Val Ala Lys Val
    1175                1180                1185

Glu Lys Gly Lys Ser Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 5
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sau Cas9 sgRNA
<220> FEATURE:
<221> NAME/KEY: modified_base
<222> LOCATION: (2)..(22)
<223> OTHER INFORMATION: a, c, u, or g

<400> SEQUENCE: 5
gnnnnnnnnn nnnnnnnnnn nnguuuuagu acucuggaaa cagaaucuac uaaaacaagg    60
caaaugccgu guuuaucucg ucaacuuguu ggcgaagauu uuuuu                   105

<210> SEQ ID NO 6
<211> LENGTH: 83
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: tracrRNA or sgRNA scaffold sequence

<400> SEQUENCE: 6

| guuuuaguac ucuggaaaca gaaucuacua aaacaaggca aaugccgugu uuaucucguc | 60 |
| aacuuguugg cgaagauuuu uuu | 83 |

<210> SEQ ID NO 7
<211> LENGTH: 3345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Sau Cas9 nucleotide sequence

<400> SEQUENCE: 7

| atggccccaa agaagaagcg gaaggtcggt atccacggag tcccagcagc caagcggaac | 60 |
| tacatcctgg gcctggacat cggcatcacc agcgtgggct acggcatcat cgactacgag | 120 |
| acacgggacg tgatcgatgc cggcgtgcgg ctgttcaaag aggccaacgt ggaaaacaac | 180 |
| gagggcaggc ggagcaagag aggcgccaga aggctgaagc ggcggaggcg catagaatc | 240 |
| cagagagtga agaagctgct gttcgactac aacctgctga ccgaccacag cgagctgagc | 300 |
| ggcatcaacc cctacgaggc cagagtgaag ggcctgagcc agaagctgag cgaggaagag | 360 |
| ttctctgccg ccctgctgca cctggccaag agaagaggcg tgcacaacgt gaacgaggtg | 420 |
| gaagaggaca ccggcaacga gctgtccacc aaagagcaga tcagccggaa cagcaaggcc | 480 |
| ctggaagaga atacgtggc cgaactgcag ctggaacggc tgaagaaaga cggcgaagtg | 540 |
| cggggcagca tcaacagatt caagaccagc gactacgtga agaagccaa acagctgctg | 600 |
| aaggtgcaga aggcctacca ccagctggac cagagcttca tcgacaccta catcgacctg | 660 |
| ctggaaaccc ggcggaccta ctatgaggga cctggcgagg gcagccctt cggctggaag | 720 |
| gacatcaaag aatggtacga gatgctgatg ggccactgca cctacttccc cgaggaactg | 780 |
| cggagcgtga agtacgccta caacgccgac ctgtacaacg ccctgaacga cctgaacaat | 840 |
| ctcgtgatca ccaggacga gaacgagaag ctggaatatt acgagaagtt ccagatcatc | 900 |
| gagaacgtgt tcaagcagaa gaagaagccc accctgaagc agatcgccaa agaaatcctc | 960 |
| gtgaacgaag aggatattaa gggctacaga gtgaccagca ccggcaagcc cgagttcacc | 1020 |
| aacctgaagg tgtaccacga catcaaggac attaccgccc ggaaagagat tattgagaac | 1080 |
| gccgagctgc tggatcagat tgccaagatc ctgaccatct accagagcag cgaggacatc | 1140 |
| caggaagaac tgaccaatct gaactccgag ctgacccagg aagagatcga gcagatctct | 1200 |
| aatctgaagg gctataccgg cacccacaac ctgagcctga aggccatcaa cctgatcctg | 1260 |
| gacgagctgt ggcacaccaa cgacaaccag atcgctatct tcaaccggct gaagctggtg | 1320 |
| cccaagaagg tggacctgtc ccagcagaaa gagatcccca ccacctggt ggacgacttc | 1380 |
| atcctgagcc ccgtcgtgaa gagaagcttc atccagagca tcaaagtgat caacgccatc | 1440 |
| atcaagaagt acggcctgcc caacgacatc attatcgagc tggcccgcga gaagaactcc | 1500 |
| aaggacgccc agaaaatgat caacgagatg cagaagcgga accggcagac caacgagcgg | 1560 |
| atcgaggaaa tcatccggac caccggcaaa gagaacgcca gtacctgat cgagaagatc | 1620 |
| aagctgcacg acatgcagga aggcaagtgc ctgtacagcc tggaagccat ccctctggaa | 1680 |

```
gatctgctga caacccctt caactatgag gtggaccaca tcatccccag aagcgtgtcc    1740
ttcgacaaca gcttcaacaa caaggtgctc gtgaagcagg aagaaaacag caagaagggc    1800
aaccggaccc cattccagta cctgagcagc agcgacagca agatcagcta cgaaaccttc    1860
aagaagcaca tcctgaatct ggccaagggc aagggcagaa tcagcaagac caagaaagag    1920
tatctgctgg aagaacggga catcaacagg ttctccgtgc agaaagactt catcaaccgg    1980
aacctggtgg ataccagata cgccaccaga ggcctgatga acctgctgcg gagctacttc    2040
agagtgaaca acctggacgt gaaagtgaag tccatcaatg gcggcttcac cagctttctg    2100
cggcggaagt ggaagtttaa gaagagcgg aacaagggt acaagcacca cgccgaggac    2160
gccctgatca ttgccaacgc cgatttcatc ttcaaagagt ggaagaaact ggacaaggcc    2220 aaaaagtga tggaaaacca gatgttcgag gaaaagcagg ccgagagcat gcccgagatc    2280
gaaaccgagc aggagtacaa agagatcttc atcaccccc accagatcaa gcacattaag    2340
gacttcaagg actacaagta cagccaccgg gtggacaaga gcctaatag agagctgatt    2400 aacgacaccc tgtactccac ccggaaggac gacaagggca cacccgat cgtgaacaat    2460 ctgaacggcc tgtacgacaa ggacaatgac aagctgaaaa agctgatcaa caagagcccc    2520
gaaaagctgc tgatgtacca ccacgacccc cagacctacc agaaactgaa gctgattatg    2580
gaacagtacg gcgacgagaa gaatcccctg tacaagtact acgaggaaac cgggaactac    2640
ctgaccaagt actccaaaaa ggacaacggc cccgtgatca agaagattaa gtattacggc    2700
aacaaactga acgcccatct ggacatcacc gacgactacc ccaacagcag aaacaaggtc    2760
gtgaagctgt ccctgaagcc ctacagattc gacgtgtacc tggacaatgg cgtgtacaag    2820
ttcgtgaccg tgaagaatct ggatgtgatc aaaaagaaa actactacga agtgaatagc    2880
aagtgctatg aggaagctaa gaagctgaag aagatcagca accaggccga gtttatcgcc    2940
tccttctaca acaacgatct gatcaagatc aacggcgagc tgtatagagt gatcggcgtg    3000
aacaacgacc tgctgaaccg gatcgaagtg aacatgatcg acatcaccta ccgcgagtac    3060
ctggaaaaca tgaacgacaa gaggcccccc aggatcatta gacaatcgc ctccaagacc    3120 cagagcatta gaagtacag cacagacatt ctgggcaacc tgtatgaagt gaaatctaag    3180
aagcaccctc agatcatcaa aaagggcaaa aggccggcgg ccacgaaaaa ggccggccag    3240
gcaaaaaaga aaagggatc ctacccatac gatgttccag attacgctta ccctatacgat    3300 gttccagatt acgcttaccc atacgatgtt ccagattacg cttaa                    3345
```

<210> SEQ ID NO 8
<211> LENGTH: 1114
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: Sau Cas9 amino acid sequence

<400> SEQUENCE: 8

Met Ala Pro Lys Lys Lys Arg Lys Val Gly Ile His Gly Val Pro Ala
1               5                   10                  15

Ala Lys Arg Asn Tyr Ile Leu Gly Leu Asp Ile Gly Ile Thr Ser Val
            20                  25                  30

Gly Tyr Gly Ile Ile Asp Tyr Glu Thr Arg Asp Val Ile Asp Ala Gly
        35                  40                  45

Val Arg Leu Phe Lys Glu Ala Asn Val Glu Asn Asn Glu Gly Arg Arg

-continued

```
                50                  55                  60
Ser Lys Arg Gly Ala Arg Arg Leu Lys Arg Arg Arg His Arg Ile
 65                  70                  75                  80

Gln Arg Val Lys Lys Leu Leu Phe Asp Tyr Asn Leu Leu Thr Asp His
                 85                  90                  95

Ser Glu Leu Ser Gly Ile Asn Pro Tyr Glu Ala Arg Val Lys Gly Leu
                100                 105                 110

Ser Gln Lys Leu Ser Glu Glu Phe Ser Ala Ala Leu Leu His Leu
                115                 120                 125

Ala Lys Arg Arg Gly Val His Asn Val Asn Glu Val Glu Glu Asp Thr
130                 135                 140

Gly Asn Glu Leu Ser Thr Lys Glu Gln Ile Ser Arg Asn Ser Lys Ala
145                 150                 155                 160

Leu Glu Glu Lys Tyr Val Ala Glu Leu Gln Leu Glu Arg Leu Lys Lys
                165                 170                 175

Asp Gly Glu Val Arg Gly Ser Ile Asn Arg Phe Lys Thr Ser Asp Tyr
                180                 185                 190

Val Lys Glu Ala Lys Gln Leu Leu Lys Val Gln Lys Ala Tyr His Gln
                195                 200                 205

Leu Asp Gln Ser Phe Ile Asp Thr Tyr Ile Asp Leu Leu Glu Thr Arg
210                 215                 220

Arg Thr Tyr Tyr Glu Gly Pro Gly Glu Gly Ser Pro Phe Gly Trp Lys
225                 230                 235                 240

Asp Ile Lys Glu Trp Tyr Glu Met Leu Met Gly His Cys Thr Tyr Phe
                245                 250                 255

Pro Glu Glu Leu Arg Ser Val Lys Tyr Ala Tyr Asn Ala Asp Leu Tyr
                260                 265                 270

Asn Ala Leu Asn Asp Leu Asn Asn Leu Val Ile Thr Arg Asp Glu Asn
                275                 280                 285

Glu Lys Leu Glu Tyr Tyr Glu Lys Phe Gln Ile Ile Glu Asn Val Phe
                290                 295                 300

Lys Gln Lys Lys Lys Pro Thr Leu Lys Gln Ile Ala Lys Glu Ile Leu
305                 310                 315                 320

Val Asn Glu Glu Asp Ile Lys Gly Tyr Arg Val Thr Ser Thr Gly Lys
                325                 330                 335

Pro Glu Phe Thr Asn Leu Lys Val Tyr His Asp Ile Lys Asp Ile Thr
                340                 345                 350

Ala Arg Lys Glu Ile Ile Glu Asn Ala Glu Leu Leu Asp Gln Ile Ala
                355                 360                 365

Lys Ile Leu Thr Ile Tyr Gln Ser Ser Glu Asp Ile Gln Glu Glu Leu
                370                 375                 380

Thr Asn Leu Asn Ser Glu Leu Thr Gln Glu Glu Ile Glu Gln Ile Ser
385                 390                 395                 400

Asn Leu Lys Gly Tyr Thr Gly Thr His Asn Leu Ser Leu Lys Ala Ile
                405                 410                 415

Asn Leu Ile Leu Asp Glu Leu Trp His Thr Asn Asp Asn Gln Ile Ala
                420                 425                 430

Ile Phe Asn Arg Leu Lys Leu Val Pro Lys Lys Val Asp Leu Ser Gln
                435                 440                 445

Gln Lys Glu Ile Pro Thr Thr Leu Val Asp Asp Phe Ile Leu Ser Pro
                450                 455                 460

Val Val Lys Arg Ser Phe Ile Gln Ser Ile Lys Val Ile Asn Ala Ile
465                 470                 475                 480
```

-continued

Ile Lys Lys Tyr Gly Leu Pro Asn Asp Ile Ile Glu Leu Ala Arg
            485             490             495

Glu Lys Asn Ser Lys Asp Ala Gln Lys Met Ile Asn Glu Met Gln Lys
                500             505             510

Arg Asn Arg Gln Thr Asn Glu Arg Ile Glu Glu Ile Ile Arg Thr Thr
            515             520             525

Gly Lys Glu Asn Ala Lys Tyr Leu Ile Glu Lys Ile Lys Leu His Asp
        530             535             540

Met Gln Glu Gly Lys Cys Leu Tyr Ser Leu Glu Ala Ile Pro Leu Glu
545             550             555             560

Asp Leu Leu Asn Asn Pro Phe Asn Tyr Glu Val Asp His Ile Ile Pro
                565             570             575

Arg Ser Val Ser Phe Asp Asn Ser Phe Asn Asn Lys Val Leu Val Lys
            580             585             590

Gln Glu Glu Asn Ser Lys Lys Gly Asn Arg Thr Pro Phe Gln Tyr Leu
        595             600             605

Ser Ser Ser Asp Ser Lys Ile Ser Tyr Glu Thr Phe Lys Lys His Ile
    610             615             620

Leu Asn Leu Ala Lys Gly Lys Gly Arg Ile Ser Lys Thr Lys Lys Glu
625             630             635             640

Tyr Leu Leu Glu Glu Arg Asp Ile Asn Arg Phe Ser Val Gln Lys Asp
                645             650             655

Phe Ile Asn Arg Asn Leu Val Asp Thr Arg Tyr Ala Thr Arg Gly Leu
            660             665             670

Met Asn Leu Leu Arg Ser Tyr Phe Arg Val Asn Asn Leu Asp Val Lys
        675             680             685

Val Lys Ser Ile Asn Gly Gly Phe Thr Ser Phe Leu Arg Arg Lys Trp
690             695             700

Lys Phe Lys Lys Glu Arg Asn Lys Gly Tyr Lys His His Ala Glu Asp
705             710             715             720

Ala Leu Ile Ile Ala Asn Ala Asp Phe Ile Phe Lys Glu Trp Lys Lys
            725             730             735

Leu Asp Lys Ala Lys Lys Val Met Glu Asn Gln Met Phe Glu Glu Lys
        740             745             750

Gln Ala Glu Ser Met Pro Glu Ile Glu Thr Glu Gln Glu Tyr Lys Glu
    755             760             765

Ile Phe Ile Thr Pro His Gln Ile Lys His Ile Lys Asp Phe Lys Asp
    770             775             780

Tyr Lys Tyr Ser His Arg Val Asp Lys Lys Pro Asn Arg Glu Leu Ile
785             790             795             800

Asn Asp Thr Leu Tyr Ser Thr Arg Lys Asp Asp Lys Gly Asn Thr Leu
            805             810             815

Ile Val Asn Asn Leu Asn Gly Leu Tyr Asp Lys Asp Asn Asp Lys Leu
        820             825             830

Lys Lys Leu Ile Asn Lys Ser Pro Glu Lys Leu Leu Met Tyr His His
    835             840             845

Asp Pro Gln Thr Tyr Gln Lys Leu Lys Leu Ile Met Glu Gln Tyr Gly
850             855             860

Asp Glu Lys Asn Pro Leu Tyr Lys Tyr Tyr Glu Glu Thr Gly Asn Tyr
865             870             875             880

Leu Thr Lys Tyr Ser Lys Lys Asp Asn Gly Pro Val Ile Lys Lys Ile
            885             890             895

```
Lys Tyr Tyr Gly Asn Lys Leu Asn Ala His Leu Asp Ile Thr Asp Asp
                900                 905                 910

Tyr Pro Asn Ser Arg Asn Lys Val Val Lys Leu Ser Leu Lys Pro Tyr
            915                 920                 925

Arg Phe Asp Val Tyr Leu Asp Asn Gly Val Tyr Lys Phe Val Thr Val
        930                 935                 940

Lys Asn Leu Asp Val Ile Lys Lys Glu Asn Tyr Tyr Glu Val Asn Ser
945                 950                 955                 960

Lys Cys Tyr Glu Glu Ala Lys Lys Leu Lys Lys Ile Ser Asn Gln Ala
                965                 970                 975

Glu Phe Ile Ala Ser Phe Tyr Asn Asn Asp Leu Ile Lys Ile Asn Gly
            980                 985                 990

Glu Leu Tyr Arg Val Ile Gly Val Asn Asn Asp Leu Leu Asn Arg Ile
        995                 1000                1005

Glu Val Asn Met Ile Asp Ile Thr Tyr Arg Glu Tyr Leu Glu Asn
        1010                1015                1020

Met Asn Asp Lys Arg Pro Pro Arg Ile Ile Lys Thr Ile Ala Ser
        1025                1030                1035

Lys Thr Gln Ser Ile Lys Lys Tyr Ser Thr Asp Ile Leu Gly Asn
        1040                1045                1050

Leu Tyr Glu Val Lys Ser Lys Lys His Pro Gln Ile Ile Lys Lys
        1055                1060                1065

Gly Lys Arg Pro Ala Ala Thr Lys Lys Ala Gly Gln Ala Lys Lys
        1070                1075                1080

Lys Lys Gly Ser Tyr Pro Tyr Asp Val Pro Asp Tyr Ala Tyr Pro
        1085                1090                1095

Tyr Asp Val Pro Asp Tyr Ala Tyr Pro Tyr Asp Val Pro Asp Tyr
        1100                1105                1110

Ala

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crRNA

<400> SEQUENCE: 9
taggaagcta atctatcatt                                           20

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caccgtagga agctaatcta tcatt                                     25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 11
aaacaatgat agattagctt cctac                                         25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acacccatct tgcagcctat                                               20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaattccca aagcgcctc                                                19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taagtagctg atctatcagt ggg                                           23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgggaagcat atctgtcatt tgg                                           23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgatagatta gcttcctacc                                               20

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 17
agagctcgca ccttatccag gtaggaagct aatctatcat taggattttg ca               52

<210> SEQ ID NO 18
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agagctcgca ccttatccag gtaggaagct aatctatcat taagattttg ca               52

<210> SEQ ID NO 19
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccttctttct ggatcagaaa aagaaactat gcaaatctt aatgatagat tagcttccta        60
cctggataag g                                                            71

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccttctttct ggatcagaaa aagaaactgc ctggataagg                             40

<210> SEQ ID NO 21
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccttctttct ggatcagaaa aagaaactat gttagcttcc tacctggata agg              53

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccttctttct ggatcagaaa aagaaactac ctggataagg                             40

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 23
ccttcttacc tggataagg                                                  19

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ccttctacct ggataagg                                                   18

<210> SEQ ID NO 25
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atggggactg tcatggatgt cctgaaggga gacaatcgct ttagcatggt aattagttcc     60
atccccgggt gga                                                        73

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggagacaat cgctttagca                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaactaatta ccatgctaaa                                                 20

<210> SEQ ID NO 28
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atggggactg tcatggatgt cctgaaggga gacaatccct ttagcatggt aattagttcc     60
atccccgggt gga                                                        73

<210> SEQ ID NO 29
<211> LENGTH: 37
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 29
aagggagaca atcgctttag catgctggta gctgcca                              37

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agacaatcgc tttagcatgc                                                 20

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aagggagaca atcgctttag catgcgggta gctgcca                              37

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagacaatcg ctttagcatg                                                 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
taaagcgatt gtctcccttc                                                 20

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tgtcctgaag ggagacaatc gctttaggta att                                  33

<210> SEQ ID NO 35
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 35
cccaatgggg actgtcatgg atgtccggaa gg                                    32

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggggactgt catggatgtc                                                  20

<210> SEQ ID NO 37
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caccaccact cagctgtaca cggactgcac ggagaagctg aggcctgaga t               51

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tcagctgtac acggactgca                                                  20

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
agctgtacac ggactgca                                                    18

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caccaccact cagctgtaca cggaccacac ggagaagctg aggcctgaga t               51

<210> SEQ ID NO 41
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 41
tcagctgtac acggaccaca                                                 20

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
agctgtacac ggaccaca                                                   18

<210> SEQ ID NO 43
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caccaccact cagctgtaca cggacctcac ggagaagctg aggcctgaga t              51

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcagctgtac acggacctca                                                 20

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agctgtacac ggacctca                                                   18
```